(12) United States Patent
Herrnstadt et al.

(10) Patent No.: US 6,171,859 B1
(45) Date of Patent: Jan. 9, 2001

(54) METHOD OF TARGETING CONJUGATE MOLECULES TO MITOCHONDRIA

(75) Inventors: Corinna Herrnstadt, San Diego, CA (US); William Davis Parker, Charlottesville, VA (US)

(73) Assignee: Mitokor, San Diego, CA (US)

( * ) Notice: Under 35 U.S.C. 154(b), the term of this patent shall be extended for 0 days.

(21) Appl. No.: 08/413,740

(22) Filed: Mar. 30, 1995

Related U.S. Application Data

(63) Continuation-in-part of application No. 08/219,842, filed on Mar. 30, 1994, now Pat. No. 5,565,323.

(51) Int. Cl.$^7$ .................................................. C12N 15/64

(52) U.S. Cl. .......................... 435/375; 514/44; 514/297

(58) Field of Search .............................. 435/6, 69.7, 174, 435/375; 424/236.1; 514/44, 297

(56) References Cited

U.S. PATENT DOCUMENTS 5,185,244  2/1993  Wallace .

FOREIGN PATENT DOCUMENTS

WO 94/09162  4/1994  (WO) .
WO 91/19815  12/1996  (WO) .

OTHER PUBLICATIONS

Parker, et al. "Cytochrome Oxidase Deficiency in Alzheimer's Disease", *Neurology* 40:1302–1303 (1990).
Anderson, et al., "Sequence and Organization of the Human Mitochondrial Genome", *Nature* 290:457–465 (1981).
Bennett, et al., "Cytochrome Oxidase Inihibition A Novel Animal Model of Alzheimer's Disease", *J. of Geriatric Psychiatry and Neurology* 5:93–101 (1992).
Kish, et al., "Brain Cytochrome Oxidase in Alzheimer's Disease", *J. of Neurochemistry* 59(2):776–779 (1993).
Bowling, et al., "Age–Dependent Impairment of Mitochondrial Function in Primate Brain", *J. of Neurochemistry* 60(5):1964–1967 (1992).
Chandrasekaran, et al., "Localization of Cytochrome Oxidase (COX) Activity and COX mRNA in Perirhinal and Superior Temporal Sulci of The Monkey Brain", *Brain Research* 606:213–219 (1993).
Douglas C. Wallace, "Mitochondrial Genetics: A Paradigm for Aging and Degenerative Diseases" *Science* 256:628–632 (1992).
Wallace, et al., "Mitochondrial DNA Mutations in Epilepsy and Neurological Disease", *Epilepsia* 35(1):S43–S50 (1994).
Shoffner, et al., "Mitochondrial DNA Variants Observed in Alzheimer Disease and Parkinson Disease Patients", *Genomics* 17:171–184 (1993).

Simonian, et al., "Functional Alterations in Alzheimer's Disease: Diminution of Cytochrome Oxidase in the Hippocampal Formation", *J. of Neuropathy and Experimental Neurology* 52(6):580–585 (1993).
Howell, et al., "Leber Hereditary Optic Neuropathy: Identification of The Same Mitochondrial ND1 Mutation in Six Pedigrees", *Am. J. Hum. Genet.* 49:939–950 (1991).
Chandrasekaran, et al., "Differential Expression of Cytochrome Oxidase (COX) Genes in Different Regions of Monkey Brain" *J. of Neuroscience Research* 32:415–423 (1992).
Suggs, et al., "Use of Synthetic Oligonucleotides as Hybridization Probes: Isolation of Cloned cDNA Sequences for Human $\beta_2$–microglobulin", *Proc. Natl. Acad. Sci. USA* 78(11):6613–6617 (1981).
Saiki, et al., "Genetic Analysis of Amplified DNA with Immobilized Sequence–Specific Oligonucleotide Probes", *Proc. Natl. Acad. USA* 86:6230–6234 (1989).
Kuppuswamy, et al., "Single Nucleotide Primer Extension to Detect Genetic Diseases: Experimental Application to Hemophilia B (Factor IX) and Cystic Fibrosis Genes", *Proc. Natl. Acad. Sci. USA* 88:1143–1147 (1991).
Syvanen, et al., "A Primer–guided Nucleotide Incorporation Assay in The Genotyping of Apolipoprotein E" *Genomics* 8:684–692 (1990).
Landegren, et al., "A Ligase–mediated Gene Detection Technique", *Science* 241:1077–1080 (1988).
Conner, et al., "Detection of Sickle Cell $\beta^s$–globin Allele by Hybridization with Synthetic Oligonucleotides", *Proc. Natl. Acad. Sci. USA* 80:278–282 (1983).
Nickerson, et al., "Automated DNA Diagnostics Using An ELISA–based Oligonucleotide Ligation Assay", *Proc. Natl. Acad. Sci. USA* 87:8923–8927 (1990).
Fodor, et al., "Multiplexed Biochemical Assays with Biological Chips", *Nature* 364:555–556.
Fodor, et al., "Light–directed, Spatially Addressable Parallel Chemical Synthesis" *Research Article* 767–773 (1991).
Matthews and Kricka, "Analytical Strategies for The Use of DNA Probes" *Analytical Biochemistry* 169:1–25 (1988).
Francis Barany, "Genetic Disease Detection and DNA Amplification Using Cloned Thermostable Ligase", *Proc. Natl. Acad. Sci. USA* 88:189–193 (1991).
Gibbs, et al., "Detection of Single DNA Base Differences by Competitive Oligonucleotide Priming", *Nucleic Acids Research* 2437–2448 (1989).

(List continued on next page.)

*Primary Examiner*—James Ketter
(74) *Attorney, Agent, or Firm*—Seed & Barry

(57) ABSTRACT

The present invention relates to genetic mutations in mitochondrial cytochrome c oxidase genes that segregate with Alzheimer's disease (AD). The invention provides methods for detecting such mutations, as a diagnostic for Alzheimer's Disease, either before or after the onset of clinical symptoms. The invention further provides treatment of cytochrome c oxidase dysfunction.

29 Claims, 9 Drawing Sheets

OTHER PUBLICATIONS

Ghosh, et al., "Use of Maleimide–thiol Coupling Chemistry for Efficient Syntheses of Oligonucleotide–enzyme Conjugate Hybridization Probes", *Bioconjugate Chem.* 1(1)71–76 (1990).

Ishii and Ghosh, "Bead–based Sandwich Hybridization Characteristics of Oligonucleotide–Alkaline Phosphatase Conjugates and Their Potential for Quantitating Target RNA Sequences", *Bioconjugate Chem.* 4(1):34–41 (1993).

Jablonski, et al., "Preparation of Oligodeoxynucleotide–alkaline Phosphatase Conjugates and Their Use as Hybridization Probes", *Nucleic Acids Research* 14(15):6115–6129 (1986).

Li, et al., "Enzyme–linked Synthetic Oligonucleotide Probes: Non–Radioactive Detection of Enterotoxigenic *Escherichia Coli* in Faecal Specimens", *Nucleic Acids Research* 15(13):5275–5287 (1987).

Newton, et al., "Analysis of Any Point Mutation in DNA. The Amplification Refractory Mutation System (ARMS)", *Nucleic Acids Research* 17(7):2503–2517 (1989).

Gingeras, et al., "Use of Self–sustained Sequence Replication Amplification Reaction to Analyze and Detect Mutations in Zidovudine–resistant Human Immunodeficiency Virus", *J. of Infectious Diseases* 164:1066–1074 (1991).

Erlich, et al., "Specific DNA Amplification", *Nature* 331:461–462 (1988).

Richman, et al., "Human Immunodeficiency Virus Type I Mutants Resistant to Nonnucleotide Inhibitors of Reverse Transcriptase Arise in Tissue Culture", *Proc. Natl. Acad. Sci. USA* 88:11241–11245 (1991).

Wu and Wallace, "The Ligation Amplification Reaction (LAR)–amplification of Specific DNA Sequences Using Sequential Rounds of Template–dependent Ligation", *Genomics* 4:560–569 (1989).

Barany, et al., *PCR Methods and App.* 1:5–16 (1991).

Partridge, et al., *Arch. Biochem. Biophys.* 310:210–217 (1994).

Parker, Davis *Ann. Neurol.* 26:719–723 (1989).

Jenner, P. *Acta Neurol. Scand.* 84:6–15 (1991).

Davis et al., "Mutations in Mitochondrial Cytochrome c Oxidase Genes Segregate with Late–Onset Alzheimer Disease," *Proceedings of the National Academy of Sciences of USA* 94: 4526–4531, 1997.

Luft, "The Development of Mitochondrial Medicine," *Proceedings of the National Academy of Sciences of USA* 91(19): 8731–8738, 1994.

Parker et al., "Cytochrome Oxidase Mutations Aiding Diagnosis of Sporadic Alzheimer's Disease," *Biotechnology Advances* 15(2): 462–463, 1997.

Parker, "Nucleotide Sequence of Human Mitochondrial Cytochrome C Oxidase II cDNA," 640: 59–64, 1991.

Power et al., "Nucleotide Sequence of Human Mitochondrial Cytochrome C Oxidase II cDNA," *Nucleic Acids Research* 17(16): 6734, 1989.

Suzuki et al., "Diabetes With Mitochondrial Gene tRNA Lys Mutation," *Diabetes Care* 17(11): 1428–1432.

COX I 5'-END NON-CODING REGION, CODING REGION:5964-7505 (1542bp), AND
3'-END NON-CODING REGION
(SEQ. ID. NO. 1)

5'-AGAGGCCTAA CCCCTGTCTTTAGATTTTAC AGTCCAATGCTTCACTCAGC
CATTTTACCT CACCCCCACT G

ATG TTC GCC GAC CGT TGA CTA TTC TCT ACA AAC CAC AAA GAC ATT GGA ACA
CTA TAC CTA TTA TTC GGC GCA TGA GCT GGA GTC CTA GGC ACA GCT CTA AGC
CTC CTT ATT CGA GCC GAG CTG GGC CAG CCA GGC AAC CTT CTA GGT AAC GAC
CAC ATC TAC AAC GTT ATC GTC ACA GCC CAT GCA TTT GTA ATA ATC TTC TTC
ATA GTA ATA CCC ATC ATA ATC GGA GGC TTT GGC AAC TGA CTA GTT CCC CTA
ATA ATC GGT GCC CCC GAT ATG GCG TTT CCC CGC ATA AAC AAC ATA AGC TTC
TGA CTC TTA CCT CCC TCT CTC CTA CTC CTG CTC GCA TCT GCT ATA GTG GAG
GCC GGA GCA GGA ACA GGT TGA ACA GTC TAC CCT CCC TTA GCA GGG AAC TAC
TCC CAC CCT GGA GCC TCC GTA GAC CTA ACC ATC TTC TCC TTA CAC CTA GCA
GGT GTC TCC TCT ATC TTA GGG GCC ATC AAT TTC ATC ACA ACA ATT ATC AAT
ATA AAA CCC CCT GCC ATA ACC CAA TAC CAA ACG CCC CTC TTC GTC TGA TCC

*Fig. 1A*

GTC CTA ATC ACA GCA GTC CTA CTT CTC CTA TCT CTC CCA GTC CTA GCT GCT
GGC ATC ACT ATA CTA CTA ACA GAC CGC AAC CTC AAC ACC ACC TTC TTC GAC
CCC GCC GGA GGA GGA GAC CCC ATT CTA TAC CAA CAC CTA TTC TGA TTT TTC
GGT CAC CCT GAA GTT TAT ATT CTT ATC CTA CCA GGC TTC GGA ATA ATC TCC
CAT ATT GTA ACT TAC TAC TCC GGA AAA AAA GAA CCA TTT GGA TAC ATA GGT
ATG GTC TGA GCT ATG ATA TCA ATT GGA TTC CTA GGG TTT ATC GTG TGA GCA
CAC CAT ATA TTT ACA GTA GGA ATA GAC GTA GAC ACA CGA GCA TAT TTC ACC
TCC GCT ACC ATA ATC ATC GCT ATC CCC ACC GGC GTC AAA GTA TTT AGC TGA
CTC GCC ACA CTC CAC GGA AGC AAT ATG AAA TGA TCT GCT GCA GTG CTC TGA
GCC CTA GGA TTC ATC CTT TTC ACC GTA GGT GGC CTG ACT GGC ATT GTA TTA
GCA AAC TCA TCA CTA GAC ATC GTA CTA CAC GAC ACG TAC TAC GTT GTA GCC
CAC TTC CAC TAT GTC CTA TCA ATA GGA GCT GTA TTT GCC ATC ATA GGA GGC
TTC ATT CAC TGA TTT CCC CTA TTC TCA GGC TAC ACC CTA GAC CAA ACC TAC
GCC AAA ATC CAT TTC ACT ATC ATA TTC ATC GGC GTA AAT CTA ACT TTC TTC
CCA CAA CAC TTT CTC GGC CTA TCC GGA ATG CCC CGA CGT TAC TCG GAC TAC
CCC GAT GCA TAC ACC ACA TGA AAC ATC CTA TCA TCT GTA GGC TCA TTC ATT
TCT CTA ACA GCA GTA ATA TTA ATA ATT TTC ATG ATT TGA GAA GCC TTC GCT
TCG AAG CGA AAA GTC CTA ATA GTA GAA GAA CCC TCC ATA AAC CTG GAG TGA
CTA TAT GGA TGC CCC CCA CCC TAC CAC ACA TTC GAA GAA CCC GTA TAC ATA
AAA TCT AGA

CAAAAAAGGA AGGAATCGAA CCCCCCAAAG CTGGTTTCAA GCCAACCCCA TGGCCTCCAT
GACTTTTTCA AAAAGGTATT AGAAAAACCA TTTCATAACT TTGTCAAAGT TAAATTATAG
GCTAA-3'

*Fig. 1B*

COX II 5'-END NON-CODING REGION, CODING REGION: 7646-8329 (684bp), AND
3'-END NON-CODING REGION
(SEQ. ID. NO. 2)

AGGTATTAGA AAAACCATTT CATAACTTTG TCGTCAAAGT TAAATTATAG
GCTAAATCCT ATATATCTTA

ATG GCA CAT GCA GCG CAA GTA GGT CTA CAA GAC GCT ACT TCC CCT ATC ATA
GAA GAG CTT ATC ACC TTT CAT GAT CAC GCC CTC ATA ATC ATT TTC CTT ATC
TGC TTC CTA GTC CTG TAT GCC CTT TTC CTA ACA CTC ACA ACA AAA CTA ACT
AAT ACT AAC ATC TCA GAC GCT CAG GAA ATA GAA ACC GTC TGA ACT ATC CTG
CCC GCC ATC ATC CTA GTC CTC ATC GCC CTC CCA TCC CTA CGC ATC CTT TAC
ATA ACA GAC GAG GTC AAC GAT CCC TCC CTT ACC ATC AAA TCA ATT GGC CAC
CAA TGG TAC TGA ACC TAC GAG TAC ACC GAC TAC GGC GGA CTA ATC TTC AAC
TCC TAC ATA CTT CCC CCA TTA TTC CTA GAA CCA GGC GAC CTG CGA CTC CTT
GAC GTT GAC AAT CGA GTA GTA CTC CCG ATT GAA GCC CCC ATT CGT ATA ATA
ATT ACA TCA CAA GAC GTC TTG CAC TCA TGA GCT GTC CCC ACA TTA GGC TTA
AAA ACA GAT GCA ATT CCC GGA CGT CTA AAC CAA ACC ACT TTC ACC GCT ACA
CGA CCG GGG GTA TAC TAC GGT CAA TGC TCT GAA ATC TGT GGA GCA AAC CAC
AGT TTC ATG CCC ATC GTC CTA GAA TTA ATT CCC CTA AAA ATC TTT GAA ATA
GGG CCC GTA TTT ACC CTA TAG

CACCCCCTCT ACCCCCTCTA GAGCCCACTG TAAAGCTAAC TTAGCATTAA C
CTTTTAAGT TAAAGATTAA GAGAACCAAC ACCTGTTTAC AGTGAAATGC

*Fig. 2*

COS III 5'-END NON-CODING REGION, CODING REGION: 9267-10052 (785 bp), AND 3'-END NON-CODING REGION
(SEQ. ID. NO. 3)

TCGCTGTCGC CTTAATCCAA GCCTACGTTT TCACACTTCT AGTAAGCCTC
TACCTGCACG ACAACACATA

ATG ACC CAC CAA TCA CAT GCC TAT CAT ATA GTA AAA CCC AGC CCA TGA CCC
CTA ACA GGG GCC CTC TCA GCC CTC CTA ATG ACC TCC GGC CTA GCC ATG TGA
TTT CAC TTC CAC TCC ATA ACG CTC CTC ATA CTA GGC CTA CTA ACC AAC ACA
CTA ACC ATA TAC CAA TGA TGG CGC GAT GTA ACA CGA GAA AGC ACA TAC CAA
GGC CAC CAC ACA CCA CCT GTC CAA AAA GGC CTT CGA TAC GGG ATA ATC CTA
TTT ATT ACC TCA GAA GTT TTT TTC TTC GCA GGA TTT TTC TGA GCC TTT TAC
CAC TCC AGC CTA GCC CCT ACC CCC CAA TTA GGA GGG CAC TGG CCC CGA ACA
GGC ATC ACC CCG CTA AAT CCC CTA GAA GTC CCA CTC CTA AAC ACA TCC GTA
TTA CTC GCA TCA GGA GTA TCA ATC ACC TGA GCT CAC CAT AGT CTA ATA GAA
AAC AAC CGA AAC CAA ATA ATT CAA GCA CTG CTT ATT ACA ATT TTA CTG GGT
CTC TAT TTT ACC CTC CTA CAA GCC TCA GAG TAC TTC GAG TCT CCC TTC ACC
ATT TCC GAC GGC ATC TAC GGC TCA ACA TTT TTT GTA GCC ACA GGC TTC CAC
GGA CTT CAC GTC ATT ATT GGC TCA ACT TTC CTC ACT ATC TGC TTC ATC CGC
CAA CTA ATA TTT CAC TTT ACA TCC AAA CAT CAC TTT GGC TTC GAA GCC GCC
GCC TGA TAC TGG CAT TTT GTA GAT GTG GTT TGA CTA TTT CTG TAT GTC TCC
ATC TAT TGA TGA GGG TCT TAC

TCTTTTAGTA TAAATAGTAC CGTTAACTTC CAATT
AACTA GTTTTGACAA CATTCAAAAA AGAGTAATAA ACTTCGCCTT AATTTTAATA
ATCAACACCC

*Fig. 3*

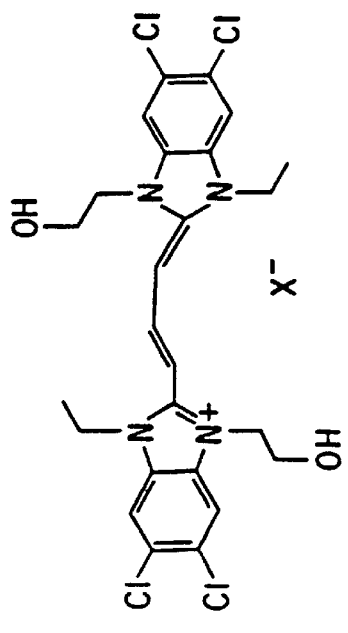
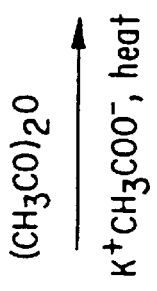
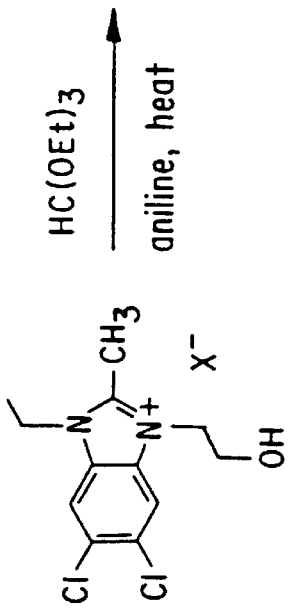
Fig. 7

For each acetal represented, this could also be a ketal where H is replaced by an alkyl group C1 to C10

SEQUENCE LISTING (1) GENERAL INFORMATION:

(iii) NUMBER OF SEQUENCES: 206

(2) INFORMATION FOR SEQ ID NO:1:

(i) SEQUENCE CHARACTERISTICS:
        (A) LENGTH: 1735 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:1:

```
AGAGGCCTAA CCCCTGTCTT TAGATTTTAC AGTCCAATGC TTCACTCAGC CATTTTACCT      60

CACCCCCACT GATGTTCGCC GACCGTTGAC TATTCTCTAC AAACCACAAA GACATTGGAA     120

CACTATACCT ATTATTCGGC GCATGAGCTG GAGTCCTAGG CACAGCTCTA AGCCTCCTTA     180

TTCGAGCCGA GCTGGGCCAG CCAGGCAACC TTCTAGGTAA CGACCACATC TACAACGTTA     240

TCGTCACAGC CCATGCATTT GTAATAATCT TCTTCATAGT AATACCCATC ATAATCGGAG     300

GCTTTGGCAA CTGACTAGTT CCCCTAATAA TCGGTGCCCC CGATATGGCG TTTCCCCGCA     360

TAAACAACAT AAGCTTCTGA CTCTTACCTC CCTCTCTCCT ACTCCTGCTC GCATCTGCTA     420

TAGTGGAGGC CGGAGCAGGA ACAGGTTGAA CAGTCTACCC TCCCTTAGCA GGGAACTACT     480

CCCACCCTGG AGCCTCCGTA GACCTAACCA TCTTCTCCTT ACACCTAGCA GGTGTCTCCT     540

CTATCTTAGG GGCCATCAAT TTCATCACAA CAATTATCAA TATAAAACCC CCTGCCATAA     600

CCCAATACCA AACGCCCCTC TTCGTCTGAT CCGTCCTAAT CACAGCAGTC CTACTTCTCC     660

TATCTCTCCC AGTCCTAGCT GCTGGCATCA CTATACTACT AACAGACCGC AACCTCAACA     720

CCACCTTCTT CGACCCCGCC GGAGGAGGAG ACCCCATTCT ATACCAACAC CTATTCTGAT     780

TTTTCGGTCA CCCTGAAGTT TATATTCTTA TCCTACCAGG CTTCGGAATA ATCTCCCATA     840

TTGTAACTTA CTACTCCGGA AAAAAGAAC CATTTGGATA CATAGGTATG GTCTGAGCTA     900

TGATATCAAT TGGATTCCTA GGGTTTATCG TGTGAGCACA CCATATATTT ACAGTAGGAA     960

TAGACGTAGA CACACGAGCA TATTTCACCT CCGCTACCAT AATCATCGCT ATCCCCACCG    1020

GCGTCAAAGT ATTTAGCTGA CTCGCCACAC TCCACGGAAG CAATATGAAA TGATCTGCTG    1080

CAGTGCTCTG AGCCCTAGGA TTCATCCTTT TCACCGTAGG TGGCCTGACT GGCATTGTAT    1140
```

```
TAGCAAACTC ATCACTAGAC ATCGTACTAC ACGACACGTA CTACGTTGTA GCCCACTTCC      1200

ACTATGTCCT ATCAATAGGA GCTGTATTTG CCATCATAGG AGGCTTCATT CACTGATTTC      1260

CCCTATTCTC AGGCTACACC CTAGACCAAA CCTACGCCAA AATCCATTTC ACTATCATAT      1320

TCATCGGCGT AAATCTAACT TTCTTCCCAC AACACTTTCT CGGCCTATCC GGAATGCCCC      1380

GACGTTACTC GGACTACCCC GATGCATACA CCACATGAAA CATCCTATCA TCTGTAGGCT      1440

CATTCATTTC TCTAACAGCA GTAATATTAA TAATTTTCAT GATTTGAGAA GCCTTCGCTT      1500

CGAAGCGAAA AGTCCTAATA GTAGAAGAAC CCTCCATAAA CCTGGAGTGA CTATATGGAT      1560

GCCCCCCACC CTACCACACA TTCGAAGAAC CCGTATACAT AAAATCTAGA CAAAAAGGA       1620

AGGAATCGAA CCCCCCAAAG CTGGTTTCAA GCCAACCCCA TGGCCTCCAT GACTTTTTCA      1680

AAAAGGTATT AGAAAAACCA TTTCATAACT TTGTCAAAGT TAAATTATAG GCTAA           1735
```

(2) INFORMATION FOR SEQ ID NO:2:

(i) SEQUENCE CHARACTERISTICS:
        (A) LENGTH: 854 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

```
AGGTATTAGA AAAACCATTT CATAACTTTG TCGTCAAAGT TAAATTATAG GCTAAATCCT        60

ATATATCTTA ATGGCACATG CAGCGCAAGT AGGTCTACAA GACGCTACTT CCCCTATCAT       120

AGAAGAGCTT ATCACCTTTC ATGATCACGC CCTCATAATC ATTTTCCTTA TCTGCTTCCT       180

AGTCCTGTAT GCCCTTTTCC TAACACTCAC AACAAAACTA ACTAATACTA ACATCTCAGA       240

CGCTCAGGAA ATAGAAACCG TCTGAACTAT CCTGCCCGCC ATCATCCTAG TCCTCATCGC       300

CCTCCCATCC CTACGCATCC TTTACATAAC AGACGAGGTC AACGATCCCT CCCTTACCAT       360

CAAATCAATT GGCCACCAAT GGTACTGAAC CTACGAGTAC ACCGACTACG GCGGACTAAT       420

CTTCAACTCC TACATACTTC CCCCATTATT CCTAGAACCA GGCGACCTGC GACTCCTTGA       480

CGTTGACAAT CGAGTAGTAC TCCCGATTGA AGCCCCCATT CGTATAATAA TTACATCACA       540

AGACCTCTTG CACTCATGAG CTGTCCCCAC ATTAGGCTTA AAAACAGATG CAATTCCCGG       600

ACGTCTAAAC CAAACCACTT TCACCGCTAC ACGACCGGGG GTATACTACG GTCAATGCTC       660

TGAAATCTGT GGAGCAAACC ACAGTTTCAT GCCCATCGTC CTAGAATTAA TTCCCCTAAA       720

AATCTTTGAA ATAGGGCCCG TATTTACCCT ATAGCACCCC CTCTACCCCC TCTAGAGCCC       780

ACTGTAAAGC TAACTTAGCA TTAACCTTTT AAGTTAAAGA TTAAGAGAAC CAACACCTGT       840

TTACAGTGAA ATGC                                                        854
```

(2) INFORMATION FOR SEQ ID NO:3:

(i) SEQUENCE CHARACTERISTICS:
        (A) LENGTH: 954 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

TCGCTGTCGC CTTAATCCAA GCCTACGTTT TCACACTTCT AGTAAGCCTC TACCTGCACG      60

ACAACACATA ATGACCCACC AATCACATGC CTATCATATA GTAAAACCCA GCCCATGACC     120

CCTAACAGGG GCCCTCTCAG CCCTCCTAAG TACCTCCGGC CTAGCCATGT GATTTCACTT     180

CCACTCCATA ACGCTCCTCA TACTAGGCCT ACTAACCAAC ACACTAACCA TATACCAATG     240

ATGGCGCGAT GTAACACGAG AAAGCACATA CCAAGGCCAC CACACACCAC CTGTCCAAAA     300

AGGCCTTCGA TACGGGATAA TCCTATTTAT TACCTCAGAA GTTTTTTTCT TCGCAGGATT     360

TTTCTGAGCC TTTTACCACT CCAGCCTAGC CCCTACCCCC CAATTAGGAG GGCACTGGCC     420

CCGAACAGGC ATCACCCCGC TAAATCCCCT AGAAGTCCCA CTCCTAAACA CATCCGTATT     480

ACTCGCATCA GGAGTATCAA TCACCTGAGC TCACCATAGT CTAATAGAAA ACAACCGAAA     540

CCAAATAATT CAAGCACTGC TTATTACAAT TTTACTGGGT CTCTATTTTA CCCTCCTACA     600

GCCTCAGAGT ACTTCGAGTC TCCCTTCACC ATTTCCGACG GCATCTACGG CTCAACATTT     660

TTTGTAGCCA CAGGCTTCCA CGGACTTCAC GTCATTATTG GCTCAACTTT CCTCACTATC     720

TGCTTCATCC GCCAACTAAT ATTTCACTTT ACATCCAAAC ATCACTTTGG CTTCGAAGCC     780

GCCGCCTGAT ACTGGCATTT TGTAGATGTG GTTTGACTAT TTCTGTATGT CTCCATCTAT     840

GATGAGGGTC TTACTCTTTT AGTATAAATA GTACCGTTAA CTTCCAATTA ACTAGTTTTG     900

ACAACATTCA AAAAGAGTA ATAAACTTCG CCTTATCAAC ACCCAATTTT AATA            954

(2) INFORMATION FOR SEQ ID NO:4:

(i) SEQUENCE CHARACTERISTICS:
         (A) LENGTH: 23 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

ACCTAGCAGG TGTCTCCTCT ATC                                              23

(2) INFORMATION FOR SEQ ID NO:5:

(i) SEQUENCE CHARACTERISTICS:
         (A) LENGTH: 27 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

CAATTTCATC ACAACAATTA TCAATAT                                          27

(2) INFORMATION FOR SEQ ID NO:6:

(i) SEQUENCE CHARACTERISTICS:

(A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:6:

GCCATAACCC AATACCAAAC G                                              21

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:7:

AATCACAGCA GTCCTACTTC TCC                                            23

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:8:

TCACAGCAGT CCTACTTCTC CTATC                                          25

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:9:

CAAAATCCAT TTCACTATCA TATTCA                                         26

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: double (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:10:

TCATAGAAGA GCTTATCACC TTTCA                                                 25

(2) INFORMATION FOR SEQ ID NO:11:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:11:

AGAGCTTATC ACCTTTCATG ATCA                                                  24

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:12:

TGCCCGCCAT CATCCTAG                                                         18

(2) INFORMATION FOR SEQ ID NO:13:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:13:

TGCCCGCCAT CATCCTAG                                                         18

(2) INFORMATION FOR SEQ ID NO:14:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:14:

ATCATCCTAG TCCTCATCGC C                                              21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:15:

GATCCCTCCC TTACCATCAA A                                              21

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:16:

AACCTACGAG ACACCGACTA CG                                             22

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:17:

AGTACTCCCG ATTGAAGCCC                                                20

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:18:

ACCTAGCAGG TATCTCCTCT ATCT                                                  24

(2) INFORMATION FOR SEQ ID NO:19:

(i) SEQUENCE CHARACTERISTICS:
             (A) LENGTH: 27 base pairs
             (B) TYPE: nucleic acid
             (C) STRANDEDNESS: double
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:19:

CAATTTCATC ACAGCAATTA TCAATAT                                               27

(2) INFORMATION FOR SEQ ID NO:20:

(i) SEQUENCE CHARACTERISTICS:
             (A) LENGTH: 21 base pairs
             (B) TYPE: nucleic acid
             (C) STRANDEDNESS: double
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:20:

GCCATAACCC TATACCAAAC G                                                     21

(2) INFORMATION FOR SEQ ID NO:21:

(i) SEQUENCE CHARACTERISTICS:
             (A) LENGTH: 22 base pairs
             (B) TYPE: nucleic acid
             (C) STRANDEDNESS: double
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:21:

AATCACAGCA GCCTACTTCT CC                                                    22

(2) INFORMATION FOR SEQ ID NO:22:

(i) SEQUENCE CHARACTERISTICS:
             (A) LENGTH: 23 base pairs
             (B) TYPE: nucleic acid
             (C) STRANDEDNESS: double
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:22:

AATCACAGCA ATCCTACTTC TCC                    23

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:23:

TCACAGCAGT CTTACTTCTC CTATC                    25

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:24:

AAAATCCATT TCGCTATCAT ATTCA                    25

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:25:

TCATAGAAGA GCCTATCACC TTTCA                    25

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:26:

AGAGCTTATC ATCTTTCATG ATCA                     24

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:27:

TGAACTATCT TGCCCGCC                                    18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:28:

TGCCCGCCAC CATCCTAG                                    18

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:29:

ATCATCCTAA TCCTCATCGC C                                21

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:30:

GATCCCTCCT TTACCATCAA AT                               22

(2) INFORMATION FOR SEQ ID NO:31:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:31:

GATCCCTCCC CTACCATCAA A                                               21

(2) INFORMATION FOR SEQ ID NO:32:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:32:

AACCTACGAG CACACCGACT AC                                              22

(2) INFORMATION FOR SEQ ID NO:33:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:33:

AACCTACGAG TGCACCGACT AC                                              22

(2) INFORMATION FOR SEQ ID NO:34:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:34:

AGTACCCGGT TGAAGCCC                                                   18

(2) INFORMATION FOR SEQ ID NO:35:

(i) SEQUENCE CHARACTERISTICS:
            (A) LENGTH: 23 base pairs
            (B) TYPE: nucleic acid (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:35:

GATAGAGGAG ACACCTGCTA GGT                                               23

(2) INFORMATION FOR SEQ ID NO:36:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:36:

ATATTGATAA TTGTTGTAGA TGAAATTG                                          28

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:37:

CGTTTGGTAT TGGGTTATGG C                                                 21

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:38:

GGAGAAGTAG GACTGCTGTG ATT                                               23

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:39:

GATAGGAGAA GTAGGACTGC TGTGA                                                  25

(2) INFORMATION FOR SEQ ID NO:40:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:40:

TGAATATGAT AGTGAAATGG ATTTTG                                                 26

(2) INFORMATION FOR SEQ ID NO:41:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:41:

TGAAAGGTGA TAAGCTCTTC TATGA                                                  25

(2) INFORMATION FOR SEQ ID NO:42:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:42:

TGATCATGAA AGGTGATAAG CTCTT                                                  25

(2) INFORMATION FOR SEQ ID NO:43:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:43:

GGCGGGCAGG ATAGTTCA                                                         18

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:44:

CTAGGATGAT GGCGGGCA                                                         18

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:45:

GGCGATGACC ACTAGGATGA T                                                     21

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:46:

TTTGATGGTA AGGGAGGGAT C                                                     21

(2) INFORMATION FOR SEQ ID NO:47:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:47:

CGTAGTCGGT GTACTCGTAG GTT                    23

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:48:

GGGCTTCAAT CGGGAGTACT                        20

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:49:

AGATAGAGGA GATACCTGCT AGGT                   24

(2) INFORMATION FOR SEQ ID NO:50:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:50:

ATATTGATAA TTGCTGTGAT GAAATTG                27

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:51:

CGTTTGGTAT AGGGTTATGG C                      21

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:52:

GGAGAAGTAG GGCTGCTGTG ATT                                           23

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (iii) HYPOTHETICAL: NO (iv) ANTI-SENSE: YES (xi) SEQUENCE DESCRIPTION: SEQ ID NO:53:

GGAGAAGTAG GATTGCTGTG ATT                                           23

(2) INFORMATION FOR SEQ ID NO:54:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:54:

GATAGGAGAA GTAAGACTGC TGTGA                                         25

(2) INFORMATION FOR SEQ ID NO:55:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:55:

TGAATATGAT AGCGAAATGG ATTTT                                         25

(2) INFORMATION FOR SEQ ID NO:56:

(i) SEQUENCE CHARACTERISTICS:

(A) LENGTH: 25 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:56:

TGAAAGGTGA TAGGCTCTTC TATGA                                             25

(2) INFORMATION FOR SEQ ID NO:57:

(i) SEQUENCE CHARACTERISTICS:
          (A) LENGTH: 24 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:57:

TGATCATGAA AGATGATAAG CTCT                                              24

(2) INFORMATION FOR SEQ ID NO:58:

(i) SEQUENCE CHARACTERISTICS:
          (A) LENGTH: 18 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:58:

GGCGGGCAAG ATAGTTCA                                                     18

(2) INFORMATION FOR SEQ ID NO:59:

(i) SEQUENCE CHARACTERISTICS:
          (A) LENGTH: 18 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:59:

GGCGGGCAAG ATAGTTCA                                                     18

(2) INFORMATION FOR SEQ ID NO:60:

(i) SEQUENCE CHARACTERISTICS:
          (A) LENGTH: 21 base pairs
          (B) TYPE: nucleic acid
          (C) STRANDEDNESS: double (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:60:

GGCGATGAGG ATTAGGATGA T                                              21

(2) INFORMATION FOR SEQ ID NO:61:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:61:

ATTTGATGGT AAAGGAGGGA TC                                             22

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:62:

TTTGATGGTA GGGGAGGGAT C                                              21

(2) INFORMATION FOR SEQ ID NO:63:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:63:

GTAGTCGGTC TGCTCGTAGG TT                                             22

(2) INFORMATION FOR SEQ ID NO:64:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:64:

GTAGTCGGTG CACTCGTAGG TT                                    22

(2) INFORMATION FOR SEQ ID NO:65:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:65:

GGGCTCAACC GGGAGTACT                                        19

(2) INFORMATION FOR SEQ ID NO:66:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:66:

AATCACAGCA GCCCTACTTC TC                                    22

(2) INFORMATION FOR SEQ ID NO:67:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:67:

AATCACAGCA GCCCTACTTC T                                     21

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:68:

AATCACAGCA GCCCTACTTC                                        20

(2) INFORMATION FOR SEQ ID NO:69:

(i) SEQUENCE CHARACTERISTICS:
      (A) LENGTH: 19 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:69:

AATCACAGCA GCCCTACTT                                         19

(2) INFORMATION FOR SEQ ID NO:70:

(i) SEQUENCE CHARACTERISTICS:
      (A) LENGTH: 18 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:70:

AATCACAGCA GCCCTACT                                          18

(2) INFORMATION FOR SEQ ID NO:71:

(i) SEQUENCE CHARACTERISTICS:
      (A) LENGTH: 17 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:71:

AATCACAGCA GCCCTAC                                           17

(2) INFORMATION FOR SEQ ID NO:72:

(i) SEQUENCE CHARACTERISTICS:
      (A) LENGTH: 16 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:72:

AATCACAGCA GCCCTA                                                        16

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:73:

ATCACAGCAG CCCTACTTCT CC                                                 22

(2) INFORMATION FOR SEQ ID NO:74:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:74:

TCACAGCAGC CCTACTTCTC C                                                  21

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:75:

CACAGCAGCC CTACTTCTCC                                                    20

(2) INFORMATION FOR SEQ ID NO:76:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:76:

ACAGCAGCCC TACTTCTCC                                                     19

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:77:

CAGCAGCCCT ACTTCTCC                                                18

(2) INFORMATION FOR SEQ ID NO:78:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:78:

AGCAGCCCTA CTTCTCC                                                 17

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:79:

ATCACAGCAG CCCTACTTCT C                                            21

(2) INFORMATION FOR SEQ ID NO:80:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:80:

TCACAGCAGC CCTACTTCT                                               19

(2) INFORMATION FOR SEQ ID NO:81:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:81:

CACAGCAGCC CTACTTC                                                        17

(2) INFORMATION FOR SEQ ID NO:82:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:82:

ACAGCAGCCC TACTT                                                          15

(2) INFORMATION FOR SEQ ID NO:83:

(i) SEQUENCE CHARACTERISTICS:
            (A) LENGTH: 37 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:83:

CCGTCCTAAT CACAGCAGCC CTACTTCTCC TATCTCT                                  37

(2) INFORMATION FOR SEQ ID NO:84:

(i) SEQUENCE CHARACTERISTICS:
            (A) LENGTH: 36 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:84:

CGTCCTAATC ACAGCAGCCC TACTTCTCCT ATCTCT                                   36

(2) INFORMATION FOR SEQ ID NO:85:

(i) SEQUENCE CHARACTERISTICS:
            (A) LENGTH: 35 base pairs
            (B) TYPE: nucleic acid

```
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:85:

GTCCTAATCA CAGCAGCCCT ACTTCTCCTA TCTCT                                  35

(2) INFORMATION FOR SEQ ID NO:86:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:86:

TCCTAATCAC AGCAGCCCTA CTTCTCCTAT CTCT                                   34

(2) INFORMATION FOR SEQ ID NO:87:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:87:

CCTAATCACA GCAGCCCTAC TTCTCCTATC TCT                                    33

(2) INFORMATION FOR SEQ ID NO:88:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:88:

CTAATCACAG CAGCCCTACT TCTCCTATCT CT                                     32

(2) INFORMATION FOR SEQ ID NO:89:

(i) SEQUENCE CHARACTERISTICS:
        (A) LENGTH: 31 base pairs
        (B) TYPE: nucleic acid
        (C) STRANDEDNESS: double
        (D) TOPOLOGY: linear
```

(ii) MOLECULE TYPE: other nucleic acid (iii) HYPOTHETICAL: NO (iv) ANTI-SENSE: YES (xi) SEQUENCE DESCRIPTION: SEQ ID NO:89:

TAATCACAGC AGCCCTACTT CTCCTATCTC T                                    31

(2) INFORMATION FOR SEQ ID NO:90:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:90:

CCGTCCTAAT CACAGCAGCC CTACTTCTCC                                      30

(2) INFORMATION FOR SEQ ID NO:91:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:91:

CGTCCTAATC ACAGCAGCCC TACTTCTCCT                                      30

(2) INFORMATION FOR SEQ ID NO:92:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:92:

GTCCTAATCA CAGCAGCCCT ACTTCTCCTA                                      30

(2) INFORMATION FOR SEQ ID NO:93:

(i) SEQUENCE CHARACTERISTICS:
            (A) LENGTH: 30 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:93:

TCCTAATCAC AGCAGCCCTA CTTCTCCTAT                                              30

(2) INFORMATION FOR SEQ ID NO:94:

(i) SEQUENCE CHARACTERISTICS:
         (A) LENGTH: 30 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:94:

CCTAATCACA GCAGCCCTAC TTCTCCTATC                                              30

(2) INFORMATION FOR SEQ ID NO:95:

(i) SEQUENCE CHARACTERISTICS:
         (A) LENGTH: 30 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:95:

CTAATCACAG CAGCCCTACT TCTCCTATCT                                              30

(2) INFORMATION FOR SEQ ID NO:96:

(i) SEQUENCE CHARACTERISTICS:
         (A) LENGTH: 30 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:96:

TAATCACAGC AGCCCTACTT CTCCTATCTC                                              30

(2) INFORMATION FOR SEQ ID NO:97:

(i) SEQUENCE CHARACTERISTICS:
         (A) LENGTH: 30 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:97:

AATCACAGCA GCCCTACTTC TCCTATCTCT                                30

(2) INFORMATION FOR SEQ ID NO:98:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:98:

TTAGTGTCGT CAGGATGAAG AGG                                       23

(2) INFORMATION FOR SEQ ID NO:99:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:99:

TTAGTGTCGT CCGGATGAAG AGG                                       23

(2) INFORMATION FOR SEQ ID NO:100:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:100:

TTAGTGTCGT CCGGATGAAG AG                                        22

(2) INFORMATION FOR SEQ ID NO:101:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:101:

TTAGTGTCGT CCGGATGAAG A                                         21

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:102:

TTAGTGTCGT CCGGATGAAG                                            20

(2) INFORMATION FOR SEQ ID NO:103:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:103:

TTAGTGTCGT CCGGATGAA                                             19

(2) INFORMATION FOR SEQ ID NO:104:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:104:

TTAGTGTCGT CCGGATGA                                              18

(2) INFORMATION FOR SEQ ID NO:105:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:105:

TTAGTGTCGT CCGGATG                                               17

(2) INFORMATION FOR SEQ ID NO:106:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:106:

TTAGTGTCGT CCGGAT                                                     16

(2) INFORMATION FOR SEQ ID NO:107:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:107:

TAGTGTCGTC CGGATGAAGA GG                                              22

(2) INFORMATION FOR SEQ ID NO:108:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:108:

AGTGTCGTCC GGATGAAGAG G                                               21

(2) INFORMATION FOR SEQ ID NO:109:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:109:

GTGTCGTCCG GATGAAGAGG                                                 20

(2) INFORMATION FOR SEQ ID NO:110:

(i) SEQUENCE CHARACTERISTICS:
        (A) LENGTH: 19 base pairs (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:110:

TGTCGTCCGG ATGAAGAGG                                                  19

(2) INFORMATION FOR SEQ ID NO:111:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:111:

GTCGTCCGGA TGAAGAGG                                                   18

(2) INFORMATION FOR SEQ ID NO:112:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:112:

TCGTCCGGAT GAAGAGG                                                    17

(2) INFORMATION FOR SEQ ID NO:113:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:113:

TAGTGTCGTC CGGATGAAGA G                                               21

(2) INFORMATION FOR SEQ ID NO:114:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:114:

AGTGTCGTCC GGATGAAGA                                                    19

(2) INFORMATION FOR SEQ ID NO:115:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:115:

GTGTCGTCCG GATGAAG                                                      17

(2) INFORMATION FOR SEQ ID NO:116:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:116:

TGTCGTCCGG ATGAA                                                        15

(2) INFORMATION FOR SEQ ID NO:117:

(i) SEQUENCE CHARACTERISTICS:
            (A) LENGTH: 37 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:117:

GGCAGGATTA GTGTCGTCCG GATGAAGAGG ATAGAGA                                37

(2) INFORMATION FOR SEQ ID NO:118:

(i) SEQUENCE CHARACTERISTICS:
            (A) LENGTH: 36 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:118:

GCAGGATTAG TGTCGTCCGG ATGAAGAGGA TAGAGA                                 36

(2) INFORMATION FOR SEQ ID NO:119:

(i) SEQUENCE CHARACTERISTICS:
            (A) LENGTH: 35 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:119:

CAGGATTAGT GTCGTCCGGA TGAAGAGGAT AGAGA                                  35

(2) INFORMATION FOR SEQ ID NO:120:

(i) SEQUENCE CHARACTERISTICS:
            (A) LENGTH: 35 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:120:

AGGATTAGTG TCCGTCCGGA TGAAGAGGAT AGAGA                                  35

(2) INFORMATION FOR SEQ ID NO:121:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:121:

GGATTAGTGT CGTCCGGATG AAGAGGATAG AGA                                    33

(2) INFORMATION FOR SEQ ID NO:122:

(i) SEQUENCE CHARACTERISTICS:
            (A) LENGTH: 32 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:122:

GATTAGTGTC GTCCGGATGA AGAGGATAGA GA                                              32

(2) INFORMATION FOR SEQ ID NO:123:

(i) SEQUENCE CHARACTERISTICS:
        (A) LENGTH: 31 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:123:

ATTAGTGTCG TCCGGATGAA GAGGATAGAG A                                               31

(2) INFORMATION FOR SEQ ID NO:124:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:124:

GGCAGGATTA GTGTCGTCCG GATGAAGAGG                                                 30

(2) INFORMATION FOR SEQ ID NO:125:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:125:

GCAGGATTAG TGTCGTCCGG ATGAAGAGGA                                                 30

(2) INFORMATION FOR SEQ ID NO:126:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:126:

CAGGATTAGT GTCGTCCGGA TGAAGAGGAT                                              30

(2) INFORMATION FOR SEQ ID NO:127:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:127:

AGGATTAGTG TCGTCCGGAT GAAGAGGATA                                              30

(2) INFORMATION FOR SEQ ID NO:128:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:128:

GGATTAGTGT CGTCCGGATG AAGAGGATAG                                              30

(2) INFORMATION FOR SEQ ID NO:129:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:129:

GATTAGTGTC GTCCGGATGA AGAGGATAGA                                              30

(2) INFORMATION FOR SEQ ID NO:130:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:130:

ATTAGTGTCG TCCGGATGAA GAGGATAGAG                                              30

(2) INFORMATION FOR SEQ ID NO:131:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:131:

TTAGTGTCGT CCGGATGAAG AGGATAGAGA                         30

(2) INFORMATION FOR SEQ ID NO:132:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:132:

CAATATGAAA ATCACCTCGG AGC                                 23

(2) INFORMATION FOR SEQ ID NO:133:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:133:

TTAGCCTATA ATTTAACTTT GAC                                 23

(2) INFORMATION FOR SEQ ID NO:134:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:134:

CAAGCCAACC CCATGGCCTC C                                     21

(2) INFORMATION FOR SEQ ID NO:135:

(i) SEQUENCE CHARACTERISTICS:

-continued

```
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:135:

AGTATTTAGT TGGGGCATTT CAC                                                23

(2) INFORMATION FOR SEQ ID NO:136:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:136:

ACAATTCTAA TTCTACTGAC TATCC                                              25

(2) INFORMATION FOR SEQ ID NO:137:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:137:

TTAGTAGTAA GGCTAGGAGG GTG                                                23

(2) INFORMATION FOR SEQ ID NO:138:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:138:

AGGCCTAACC CCTGTC                                                        16

(2) INFORMATION FOR SEQ ID NO:139:

(i) SEQUENCE CHARACTERISTICS:
        (A) LENGTH: 15 base pairs
        (B) TYPE: nucleic acid
        (C) STRANDEDNESS: double
```

(D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:139:

GGCCATGGGG TTGGC                                                        15

(2) INFORMATION FOR SEQ ID NO:140:

(i) SEQUENCE CHARACTERISTICS:
          (A) LENGTH: 17 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:140:

AGGTATTAGA AAAACCA                                                      17

(2) INFORMATION FOR SEQ ID NO:141:

(i) SEQUENCE CHARACTERISTICS:
          (A) LENGTH: 17 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:141:

ATCTTTAACT TAAAAGG                                                      17

(2) INFORMATION FOR SEQ ID NO:142:

(i) SEQUENCE CHARACTERISTICS:
          (A) LENGTH: 15 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:142:

GCCTTAATCC AAGCC                                                        15

(2) INFORMATION FOR SEQ ID NO:143:

(i) SEQUENCE CHARACTERISTICS:
          (A) LENGTH: 18 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:143:

GAATGTTGTC AAAACTAG                                                         18

(2) INFORMATION FOR SEQ ID NO:144:

(i) SEQUENCE CHARACTERISTICS:
             (A) LENGTH: 16 base pairs
             (B) TYPE: nucleic acid
             (C) STRANDEDNESS: double
             (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:144:

AGGCCTAACC CCTGTC                                                           16

(2) INFORMATION FOR SEQ ID NO:145:

(i) SEQUENCE CHARACTERISTICS:
             (A) LENGTH: 13 base pairs
             (B) TYPE: nucleic acid
             (C) STRANDEDNESS: double
             (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:145:

GTCACAGCCC ATG                                                              13

(2) INFORMATION FOR SEQ ID NO:146:

(i) SEQUENCE CHARACTERISTICS:
             (A) LENGTH: 16 base pairs
             (B) TYPE: nucleic acid
             (C) STRANDEDNESS: double
             (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:146:

CCTGGAGCCT CCGTAG                                                           16

(2) INFORMATION FOR SEQ ID NO:147:

(i) SEQUENCE CHARACTERISTICS:
             (A) LENGTH: 14 base pairs
             (B) TYPE: nucleic acid
             (C) STRANDEDNESS: double
             (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:147:

CTTCTTCGAC CCCG                                                        14

(2) INFORMATION FOR SEQ ID NO:148:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:148:

CATATTTCAC CTCCG                                                       15

(2) INFORMATION FOR SEQ ID NO:149:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:149:

CCTATCAATA GGAGC                                                       15

(2) INFORMATION FOR SEQ ID NO:150:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:150:

CATCCTATCA TCTGTAGG                                                    18

(2) INFORMATION FOR SEQ ID NO:151:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:151:

AGGTATTAGA AAAACCA                              17

(2) INFORMATION FOR SEQ ID NO:152:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:152:

TAACTAATAC TAACATCT                             18

(2) INFORMATION FOR SEQ ID NO:153:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:153:

TGCGACTCCT TGAC                                 14

(2) INFORMATION FOR SEQ ID NO:154:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:154:

GCCTTAATCC AAGCC                                15

(2) INFORMATION FOR SEQ ID NO:155:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:155:

CAATGATGGC GCGATG                               16

(2) INFORMATION FOR SEQ ID NO:156:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:156:

CCGTATTACT CGCATCAGG                                                19

(2) INFORMATION FOR SEQ ID NO:157:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:157:

CCGACGGCAT CTACGGC                                                  17

(2) INFORMATION FOR SEQ ID NO:158:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:158:

TGCTTCACTC AGCC                                                        14

(2) INFORMATION FOR SEQ ID NO:159:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:159:

AGGCCTAACC CCTGTA                                                   16

(2) INFORMATION FOR SEQ ID NO:160:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:160:

AGTCCAATGC TTCACTCA                                            18

(2) INFORMATION FOR SEQ ID NO:161:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:161:

GCTATAGTGG AGGC                                                14

(2) INFORMATION FOR SEQ ID NO:162:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:162:

CTCCTACTCC TGCTCGCA                                            18

(2) INFORMATION FOR SEQ ID NO:163:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:163:

TCCTGCTCGC ATCTGCTA                                            18

(2) INFORMATION FOR SEQ ID NO:164:

(i) SEQUENCE CHARACTERISTICS:
        (A) LENGTH: 18 base pairs
        (B) TYPE: nucleic acid

```
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:164:

CTCCTACTCC TGCTCGCA                                                    18

(2) INFORMATION FOR SEQ ID NO:165:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:165:

CCTACCAGGA TTCG                                                        14

(2) INFORMATION FOR SEQ ID NO:166:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:166:

CCTACCAGGC TTCGGAA                                                     17

(2) INFORMATION FOR SEQ ID NO:167:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:167:

TCCTACCAGG CTTCGGAA                                                    18

(2) INFORMATION FOR SEQ ID NO:168:

(i) SEQUENCE CHARACTERISTICS:
        (A) LENGTH: 15 base pairs
        (B) TYPE: nucleic acid
        (C) STRANDEDNESS: double
        (D) TOPOLOGY: linear
```

(ii) MOLECULE TYPE: other nucleic acid (iii) HYPOTHETICAL: NO (iv) ANTI-SENSE: NO (xi) SEQUENCE DESCRIPTION: SEQ ID NO:168:

CCTATCAATA GGAGC                                                          15

(2) INFORMATION FOR SEQ ID NO:169:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:169:

GTCCTATCAA TAGGAGCTGT A                                                   21

(2) INFORMATION FOR SEQ ID NO:170:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:170:

GTAGAGTGTG CAACC                                                          15

(2) INFORMATION FOR SEQ ID NO:171:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:171:

GTCTACGGAG GCTCC                                                          15

(2) INFORMATION FOR SEQ ID NO:172:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:172:

AGGTCTACGG AGGCTCCA                                             18

(2) INFORMATION FOR SEQ ID NO:173:

(i) SEQUENCE CHARACTERISTICS:
       (A) LENGTH: 21 base pairs
       (B) TYPE: nucleic acid
       (C) STRANDEDNESS: double
       (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:173:

AGGAGACACC TGCTAGGTGT A                                         21

(2) INFORMATION FOR SEQ ID NO:174:

(i) SEQUENCE CHARACTERISTICS:
       (A) LENGTH: 16 base pairs
       (B) TYPE: nucleic acid
       (C) STRANDEDNESS: double
       (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:174:

CCATACCTAT GTATCC                                               16

(2) INFORMATION FOR SEQ ID NO:175:

(i) SEQUENCE CHARACTERISTICS:
       (A) LENGTH: 21 base pairs
       (B) TYPE: nucleic acid
       (C) STRANDEDNESS: double
       (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:175:

TCACACGATA AACCCTAGGA A                                         21

(2) INFORMATION FOR SEQ ID NO:176:

(i) SEQUENCE CHARACTERISTICS:
       (A) LENGTH: 20 base pairs
       (B) TYPE: nucleic acid
       (C) STRANDEDNESS: double
       (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:176:

GACCATACCT ATGTATCCAA                                           20

(2) INFORMATION FOR SEQ ID NO:177:

(i) SEQUENCE CHARACTERISTICS:
         (A) LENGTH: 14 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:177:

CCTCCTATGA TGGC                                                 14

(2) INFORMATION FOR SEQ ID NO:178:

(i) SEQUENCE CHARACTERISTICS:
         (A) LENGTH: 18 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:178:

GTGTAGCCTG AGAATAGG                                             18

(2) INFORMATION FOR SEQ ID NO:179:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:179:

GTCTAGGGTG TAGCCTGAGA A                                         21

(2) INFORMATION FOR SEQ ID NO:180:

(i) SEQUENCE CHARACTERISTICS:
         (A) LENGTH: 16 base pairs
         (B) TYPE: nucleic acid
         (C) STRANDEDNESS: double
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:180:

GGGTTCGATT CCTTCC                                               16

(2) INFORMATION FOR SEQ ID NO:181:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:181:

TGGATTGAAA CCAGC                                                15

(2) INFORMATION FOR SEQ ID NO:182:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:182:

GTTGGCTTGA AACCAGCTT                                      19

(2) INFORMATION FOR SEQ ID NO:183:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:183:

TCATAACTTT GTCGTC                                          16

(2) INFORMATION FOR SEQ ID NO:184:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:184:

CATTTCATAA CTTTGTCGTC                                    20

(2) INFORMATION FOR SEQ ID NO:185:

(i) SEQUENCE CHARACTERISTICS:
    (A) LENGTH: 17 base pairs
    (B) TYPE: nucleic acid
    (C) STRANDEDNESS: double
    (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:185:

AGGTATTAGA AAAACCA                                                17

(2) INFORMATION FOR SEQ ID NO:186:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:186:

AAGGTATTAG AAAAACC                                                17

(2) INFORMATION FOR SEQ ID NO:187:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:187:

TTCATAACTT TGTCGTCAA                                              19

(2) INFORMATION FOR SEQ ID NO:188:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:188:

AAGGTATTAG AAAAACC                                                17

(2) INFORMATION FOR SEQ ID NO:189:

(i) SEQUENCE CHARACTERISTICS:
        (A) LENGTH: 18 base pairs (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:189:

CCATGGCCTC CATGACTT                                                    18

(2) INFORMATION FOR SEQ ID NO:190:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:190:

TGGTACTGAA CCTACG                                                      16

(2) INFORMATION FOR SEQ ID NO:191:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:191:

ACAGACGAGG TCAACGAT                                                    18

(2) INFORMATION FOR SEQ ID NO:192:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:192:

CATAACAGAC GAGGTCCA                                                    18

(2) INFORMATION FOR SEQ ID NO:193:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:193:

AGTTGAAGAT TAGTCC                                                                    16

(2) INFORMATION FOR SEQ ID NO:194:

(i) SEQUENCE CHARACTERISTICS:
              (A) LENGTH: 20 base pairs
              (B) TYPE: nucleic acid
              (C) STRANDEDNESS: double
              (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:194:

TAGGAGTTGA AGATTAGTCC                                                                20

(2) INFORMATION FOR SEQ ID NO:195:

(i) SEQUENCE CHARACTERISTICS:
              (A) LENGTH: 19 base pairs
              (B) TYPE: nucleic acid
              (C) STRANDEDNESS: double
              (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:195:

TGAAGATAAG TCCGCCGTA                                                                 19

(2) INFORMATION FOR SEQ ID NO:196:

(i) SEQUENCE CHARACTERISTICS:
              (A) LENGTH: 17 base pairs
              (B) TYPE: nucleic acid
              (C) STRANDEDNESS: double
              (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:196:

GTTAATGCTA AGTTAGC                                                                   17

(2) INFORMATION FOR SEQ ID NO:197:

(i) SEQUENCE CHARACTERISTICS:
              (A) LENGTH: 22 base pairs
              (B) TYPE: nucleic acid
              (C) STRANDEDNESS: double
              (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:197:

AAGGTTAATG CTAAGTTAGC TT                                              22

(2) INFORMATION FOR SEQ ID NO:198:

(i) SEQUENCE CHARACTERISTICS:
            (A) LENGTH: 14 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:198:

AAGCCTCTAC CTGC                                                       14

(2) INFORMATION FOR SEQ ID NO:199:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:199:

CTTAATCCAA GCCTACG                                                    17

(2) INFORMATION FOR SEQ ID NO:200:

(i) SEQUENCE CHARACTERISTICS:
            (A) LENGTH: 14 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:200:

AACAGGCATC ACCC                                                       14

(2) INFORMATION FOR SEQ ID NO:201:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:201:

CATCCGTATT ACTCGCATCA                                          20

(2) INFORMATION FOR SEQ ID NO:202:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:202:

GATGCGAGTA ATACG                                               15

(2) INFORMATION FOR SEQ ID NO:203:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:203:

GATGCGAGTA ATACGGAT                                            18

(2) INFORMATION FOR SEQ ID NO:204:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:204:

AATTGGAAGT TAACGG                                              16

(2) INFORMATION FOR SEQ ID NO:205:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:205:

-continued

```
AATTGGAAGT TAACGGTA                                                     18

(2) INFORMATION FOR SEQ ID NO:206:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:206:

GTCAAAACTA GTTAATTGGA A                                                 21
```

METHOD OF TARGETING CONJUGATE MOLECULES TO MITOCHONDRIA

This application is a continuation-in-part of application Ser. No. 08/219,842 now U.S. Pat. No. 5,565,323 filed Mar. 30, 1994, the disclosure of which is herein incorporated by reference in its entirety.

FIELD OF THE INVENTION

The present invention relates generally to the diagnosis and treatment of Alzheimer's disease. More specifically, the invention relates to detecting genetic mutations in mitochondrial cytochrome c oxidase genes as a means for diagnosing Alzheimer's disease and suppressing these same mutations or the effects of these mutations in the treatment of Alzheimer's disease.

BACKGROUND OF THE INVENTION

Alzheimer's disease (AD) is a progressive neurodegenerative disorder characterized by loss and/or a trophy of neurons in discrete regions of the brain, accompanied by extracellular deposits of β-amyloid and the intracellular accumulation of neurofibrillary tangles. It is a uniquely human disease, affecting over 13 million people worldwide. It is also a uniquely tragic disease. Many individuals who have lived normal, productive lives are slowly stricken with AD as they grow older, and the disease gradually robs them of their memory and other mental faculties. Eventually, they even cease to recognize family and loved ones, and they often require continuous care until their eventual death.

Alzheimer's disease is incurable and untreatable, except symptomatically. Persons suffering from Alzheimer's disease may have one of two forms of this disease: "familial" AD or "sporadic" AD.

Familial Alzheimer's disease accounts for only about 5 to 10% of all Alzheimer's cases and has an unusually early-onset, generally before the age of fifty. Familial AD is inherited and follows conventional patterns of mendelian inheritance. This form of AD has been linked to nuclear chromosomal abnormalities.

In contrast, the second form of Alzheimer's disease, sporadic AD, is a late-onset disease which is neither inherited nor caused by nuclear chromosomal abnormalities. This late onset form of the disease is the more common type of Alzheimer's disease and is believed to account for approximately 90 to 95% of all Alzheimer's cases.

It has been recognized that some degenerative diseases such as Leber's hereditary optic neuropathy, myoclonus, epilepsy, lactic acidosis and stroke (MELAS), and myoclonic epilepsy ragged red fiber syndrome, are transmitted through mitochondrial DNA mutations. Mitochondrial DNA mutations have also been implicated in explaining the apparently "sporadic" (nonmendelian) occurrence of some degenerative neurologic disorders, such as Parkinson's and Alzheimer's disease. Proteins encoded by the mitochondrial genome are components of the electron transport chain, and deficits in electron transport function have been reported in Parkinson's and Alzheimer's disease. In particular, it has been reported that defects in cytochrome c oxidase, an important terminal component of the electron transport chain located in the mitochondria of eukaryotic cells, may be involved in Alzheimer's disease.

One report suggesting a relation between AD and cytochrome c oxidase is Parker et al., Neurology 40: 1302–1303 (1990), which finds that patients with Alzheimer's disease have reduced cytochrome c oxidase activity. It has also been shown by Bennett et al., J. Geriatric Psychiatry and Neurology 5:93–101 (1992), that when sodium azide, a specific inhibitor of cytochrome c oxidase (COX) was infused into rats, the rats suffered impaired memory and learning (a form of dementia). The rats mimicked the effect of Alzheimer's disease in humans. In addition, the sodium azide-tested rats failed to display long term potentiation, demonstrating loss of neuronal plasticity. It has been hypothesized that the reduced cytochrome c oxidase activity leads to increased intracellular levels of oxygen free radicals, and that the cumulative effects of free radical-mediated lipid oxidation ultimately cause the degenerative neurological changes that are characteristic of AD. Wallace, D. C., Science, 256:628–632 (1992).

Despite these findings, prior to the present invention, the exact mechanism producing the electron transport dysfunctions was not known for Alzheimer's disease, nor had a genetic or structural basis for these dysfunctions been identified. Without knowing what causes these electron transport dysfunctions and in particular the genetic or structural basis, it is difficult to diagnose or treat Alzheimer's disease, especially the predominant form, sporadic AD.

To date, the diagnosis of probable Alzheimer's disease is only by clinical observation and is a diagnosis of exclusion. Unfortunately, definitive diagnosis can be accomplished only by pathological examination at autopsy. While attempts have been made to diagnose Alzheimer's disease by identifying differences in certain biological markers, including protease nexin II and apolipoprotein E alleles, this approach has not been successful. Incomplete penetrance in AD patients or crossover into normal or other disease populations makes identification of biological markers an unreliable method of diagnosis. Clearly, a reliable diagnosis of Alzheimer's at its earliest stages is critical for efficient and effective intercession and treatment of this debilitating disease. Thus, there exists a definite need for an effective diagnostic of Alzheimer's disease, and especially for the more prevalent form, sporadic AD. There also exists a need for a non-invasive diagnostic that is reliable at or before the earliest manifestations of AD symptoms.

Not only does the Alzheimer's field currently lack a reliable, early means of detections there is at present no effective therapy for AD, other than certain palliative treatments. Current therapies in clinical evaluation are designed to treat the symptoms of the disease and not impact the underlying pathology of AD. These therapies include Cognex, E2020, and other similar agents known in the field. However, since the primary etiologic events in AD are not yet known in the art, rational therapies have not been designed. As a result, there exists a need for effective therapies, particularly those that address the primary cause of AD.

The present invention satisfies these needs for a useful diagnostic and effective treatment of Alzheimer's disease and provides related advantages as well.

SUMMARY OF THE INVENTION

The present invention relates to the identification of genetic mutations in mitochondrial cytochrome c oxidase genes which segregate with Alzheimer's disease. The invention provides methods for detecting such mutations as a diagnostic for Alzheimer's disease, either before or after the onset of clinical symptoms.

According to an embodiment of the present invention for detecting the presence of Alzheimer's disease, a biological sample containing mitochondria from a subject is obtained and one or more mutations in the sequence of a mitochondrial cytochrome c oxidase gene which correlates with the presence of Alzheimer's disease is interrogated. Such interrogated mutations are preferably positioned between codon 155 and codon 415 of the cytochrome c oxidase I gene and/or between codon 20 and codon 150 of the cytochrome c oxidase II gene. More preferably, the mutations are interrogated at one or more of the following positions: codon 155, codon 167, codon 178, codon 193, codon 194, and codon 415 of the cytochrome c oxidase I gene; and codon 20, codon 22, codon 68, codon 71, codon 74, codon 95, codon 110, and codon 146 of the cytochrome c oxidase II gene. If desired, the codon of interest can be amplified prior to interrogation.

Preferred methods for interrogating the above mutations include: (a) hybridization with oligonucleotide probes, (b) methods based on the ligation of oligonucleotide sequences that anneal adjacent to one another on target nucleic acids, such as the ligase chain reaction, (c) the polymerase chain reaction or variants thereof which depend on using sets of primers, and (d) single nucleotide primer-guided extension assays.

The present invention also encompasses nucleic acid sequences which are useful in the above mentioned diagnostics, namely those which correspond, or are complementary, to portions of mitochondrial cytochrome c oxidase gene that contain gene mutations which correlate with the presence of Alzheimer's disease. According to one embodiment, the nucleic acid sequences are labelled with detectable agents. Preferred detectable agents include radioisotopes (such as $^{32}P$) haptens (such as digoxigenin), biotin, enzymes (such as alkaline phosphatase or horseradish peroxidase), fluorophores (such as fluorescein or Texas Red), or chemilumiphores (such as acridine).

According to another embodiment for detecting the presence of Alzheimer's disease, a biological sample is interrogated for the presence of protein products. In particular, protein products of mitochondria with one or more cytochrome c oxidase mutations that correlate with the presence of Alzheimer's disease are interrogated Preferred agents for the interrogation of such proteins include monoclonal antibodies.

According to another embodiment of the present invention, genetic mutations which cause Alzheimer's disease are detected by determining the sequence of mitochondrial cytochrome c oxidase genes from subjects known to have Alzheimer's disease, and comparing the sequence to that of known wild-type mitochondrial cytochrome c oxidase genes.

Other embodiments of the present invention pertain to suppression of the undesired biological activity of the mutations. This affords a therapeutic treatment for Alzheimer's disease. More specifically, one embodiment of the invention pertains to methods of inhibiting the transcription or translation of mutant cytochrome c oxidase encoding genes by contacting the genes with antisense sequences which are specific for mutant sequences and which hybridize to a target mutant cytochrome c oxidase gene or messenger RNA transcribed therefrom.

Another embodiment of the invention concerns the selective introduction of a conjugate molecule into mitochondria with defective cytochrome c oxidase genes. The conjugate comprises a targeting molecule conjugated to a toxin or to an imaging ligand using a linker. The targeting molecule can be, for example, a lipophilic cation such as an acridine orange derivative, a rhodamine 123 derivative, or a JC-1 (5,5',6,6'-tetrachloro-1,1',3,3'-tetraethylbenzimidiazolocarbocyanine iodide) derivative, The linker can include, for example, an ester, ether, thioether, phosphorodiester, thiophosphorodiester, carbonate, carbamate, hydrazone, oxime, amino or amide functionality. The imaging ligand can be, for example, a radioisotope, hapten, biotin, enzyme, fluorophore or chemilumiphore. And the toxin can be, for example, phosphate, thiophosphate, dinitrophenol, maleimide and antisense oligonucleic acids.

The appended claims are hereby incorporated by reference as a further enumeration of preferred embodiments.

It is an object of the present invention to identify the structural and genetic basis for the electron transport dysfunctions that are known to accompany Alzheimer's disease.

It is another object of the present invention to provide reliable and efficient means for the diagnosis of Alzheimer's disease.

It is another object of the present invention to provide effective therapies for the treatment of Alzheimer's disease.

One advantage of the present invention is that it provides an effective diagnostic of Alzheimer's disease, particularly for the more prevalent form, sporadic AD.

Another advantage of the present invention is that it affords a non-invasive diagnostic that is reliable at or before the earliest manifestations of AD symptoms.

Still another object of the present invention is that it provides an effective therapy that addresses the primary cause of AD, by suppressing the undesired biological activity of mutations that segregate with Alzheimer's disease or by selectively destroying defective mitochondria.

Other objects and advantages of the invention and alternative embodiments will readily become apparent to those skilled in the art, particularly after reading the detailed description, and examples set forth below.

BRIEF DESCRIPTION OF THE FIGURES

FIGS. 1a and 1b list the 5' end upstream non-coding region, the complete nucleic acid sequence encoding mitochondrial cytochrome c oxidase subunit I and the 3' end downstream non-coding region. (SEQ. ID. NO. 1).

FIG. 2 lists the 5' end non-coding region, the complete nucleic acid sequence of the mitochondrial cytochrome c oxidase subunit II coding region and the 3' end downstream non-coding region. (SEQ. ID. NO. 2).

FIG. 3 lists the 5' end non-coding region, the complete nucleic acid sequence of the mitochondrial cytochrome c oxidase subunit III coding region and the 3' end downstream non-coding region. (SEQ. ID. NO. 3).

FIGS. 5–8 illustrate reaction schemes for the preparation of several JC-1 derivatives useful for the detection and selective destruction of defective mitochondria.

DETAILED DESCRIPTION OF THE INVENTION

Figure 4:
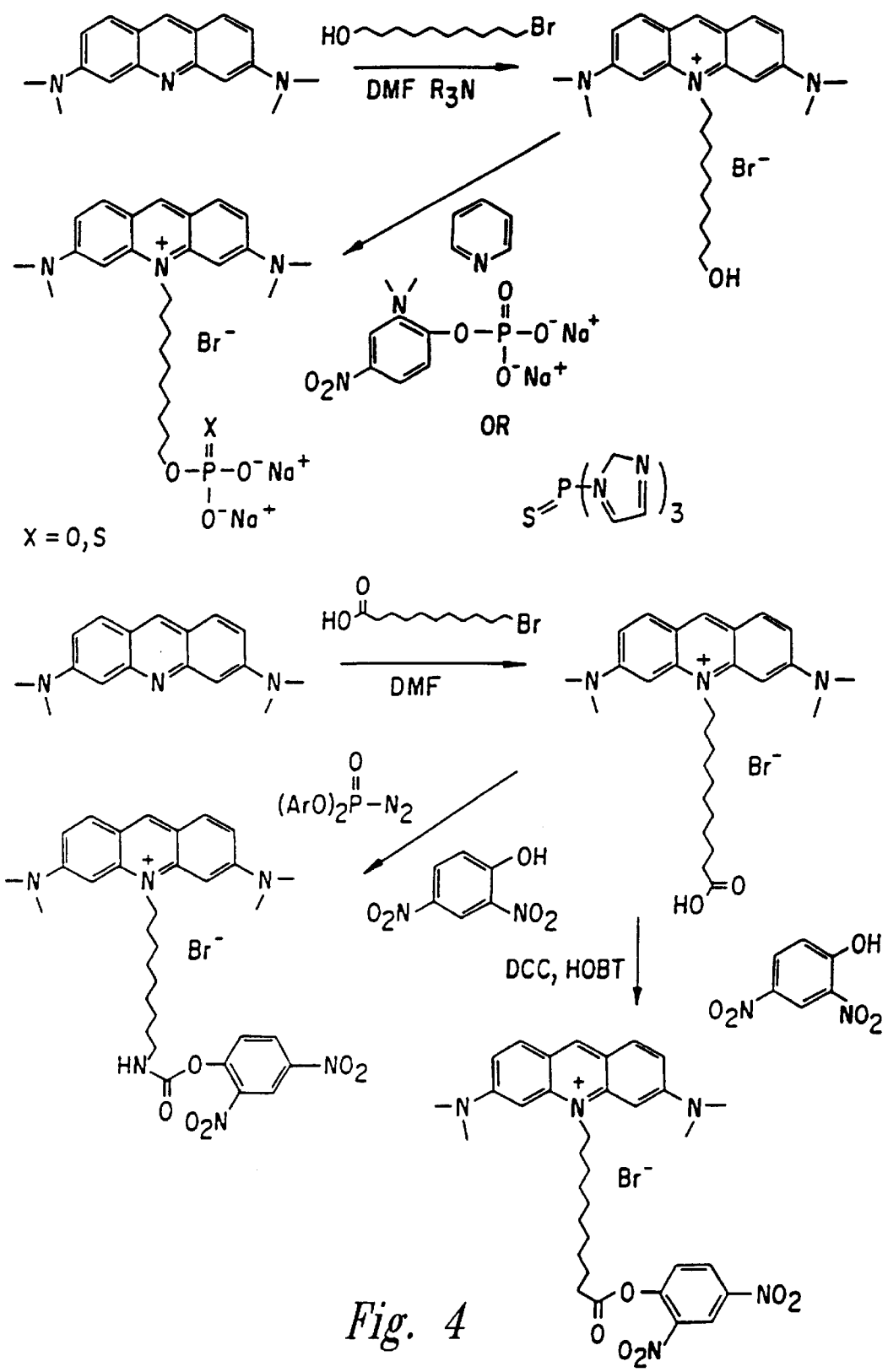
FIG. 4 illustrates a reaction scheme for the preparation of several acridine orange derivatives useful for the detection and selective destruction of defective mitochondria.

The present invention relates to genetic mutations in mitochondrial cytochrome c oxidase genes which segregate with Alzheimer's disease. The invention provides methods for detecting such mutations, as a diagnostic for Alzheimer's disease, either before or after the onset of clinical symptoms. Moreover, the invention also pertains to suppression of the undesired biological activity of the mutations and thus affords a therapeutic treatment for Alzheimer's disease. Not only does this invention provide the first effective diagnostic of Alzheimer's disease which is reliable at or before the earliest manifestations of AD symptoms, it also provides the first effective therapy for this debilitating disease.

In order to facilitate a full and complete understanding of the present invention, it is important to note that all terms used herein are intended to have the same meaning as generally ascribed to those terms by those skilled in the art of molecular genetics, unless defined to the contrary. The references cited herein are incorporated by reference in their entireties.

In using the terms "nucleic acid", RNA, DNA, etc., we do not mean to limit the chemical structures that can be used in particular steps. For example, it is well known to those skilled in the art that RNA can generally be substituted for DNA, and as such, the use of the term "DNA" should be read by those skilled in the art to include this substitution. In addition, it is known that a variety of nucleic acid analogues and derivatives can be made and will hybridize to one another and to DNA and RNA, and the use of such analogues and derivatives is also within the scope of the present invention.

Segregation of Cytochrome C Oxidase Mutations with Alzheimer's Disease

Cytochrome c oxidase (COX) is an important terminal component of the electron transport chain located in the mitochondria of eukaryotic cells. Cytochrome c oxidase, also known as complex IV of the electron transport chain, is composed of at least thirteen subunits. At least ten of these subunits are encoded by nuclear genes; the remaining three subunits (I, II, and III) are encoded by mitochondrial genes. Mitochondrial DNA (mtDNA) is a small circular DNA molecule that is approximately 17 kB long in humans. The mtDNA encodes for two ribosomal RNAs (rRNA), a complete set of transfer RNAs (tRNA) and thirteen proteins, including three cytochrome c oxidase subunits COX I, COX II, and COX III.

Most of the mtDNA present in an individual is derived from the mtDNA contained within the ovum at the time of the individual's conception. Mutations in mtDNA sequence which affect all copies of mtDNA in an individual are known as homoplasmic. Mutations which affect only some copies of mtDNA are known as heteroplasmic and will vary between different mitochondria in the same individual. It should also be noted that most mitochondrially encoded proteins and all mitochondrially encoded COX proteins are transcribed from the heavy strand of mtDNA. The other strand is called the "light strand," because mtDNA can be separated into heavy and light single strands on the basis of their density.

In the present invention, mtDNA from both normal individuals and known Alzheimer's patients are isolated, cloned and sequenced. As expected, a few nondeleterious and apparently random mutations in each gene including some normal genes, are observed. However, in the AD patients, a small number of homoplasmic or heteroplasmic mutations at common sites are noted. For the three mitochondrial COX subunits, the mutations occurred in one or more of the subunit clones for each individual. Such mutations are especially observed in the expressed regions of COX subunits I and II of the mtDNA.

According to the present invention, such mutations in COX genes segregate with, and are apparently sufficient for, Alzheimer's disease. Sporadic AD, which accounts for at least 90% of all AD patients, is segregated with heteroplasmic mutation(s) in the mtDNA-encoded COX subunits. Detection of these mutations, therefore, is both predictive and diagnostic of Alzheimer's disease.

Blood and brain samples are harvested and DNA isolated from a number of clinically-classified or autopsy confirmed AD patients, from a number of documented age-matched 'normals' (elderly individuals with no history of AD or any sign of clinical symptoms of AD) and from age-matched neurodegenerative disease controls (patients with Huntington's disease, parasupranuclear palsy, and so forth). After cloning of cytochrome c oxidase (COX) gene fragments, the sequences of multiple clones from each patient are obtained. Compilation of the sequences are made, aligned, and compared with published Cambridge and Genbank sequences (Anderson et al., *Nature* 290:457–465 (1981)) for known normal human COX genes The published Cambridge coding sequences are numbered as follows: COX I is nucleotides 5964 to 7505, COX II is nucleotides 7646 to 8329, and COX III is nucleotides 9267 to 10052. The corresponding sequences are numbered as follows according to Anderson's scheme: COX I is nucleotides 5904 to 7445, COX II is nucleotides 7586 to 8269, and COX III is nucleotides 9207 to 9992. Id. All reference hereinbelow is made only to the published Cambridge sequences, though it will be appreciated by those of skill in the art that the corresponding sequences, following a different numbering scheme, including Anderson's, could be used in the invention.

Any variation (mutation, insertion, or deletion) from published sequences is verified by replication and by complementary strand sequencing. Analysis of the variations in known AD patients indicated a significant number of mutations. Some of the mutations observed are 'silent' mutations resulting in no amino acid changes in the expressed protein. However, a number of mutations present result in amino acid changes in the corresponding protein. In many instances the corresponding amino acid change may also lead to conformational changes to the COX enzyme.

In cytochrome c oxidase subunit II, for example, the sequence in AD patients varies from the normal sequence in at least one base per gene. The data is summarized in Table 2 hereinbelow. Several of the recurrent mutations observed are believed to result in conformational alterations of the COX enzyme. For example, mutation of the normal ACC observed at codon 22 to ATC results in a change from the normal hydrophilic threonine (Thr) to a hydrophobic isoleucine (Ile). Changes of this type in nucleic acid structure, particularly when occurring in highly conserved areas, are known to disrupt or modify enzymatic activity.

As described more fully hereinbelow, each of the COX genes sequenced shows significant variation from the normal sequence at a number of specific sites, or mutational "hot spots." Moreover, these hot spots generally fall within particular regions of the COX genes. In the first 1,530 bases (510 codons) of COX I, and in particular between codons 155 and 415, codons 155, 167, 178, 193, 194 and 415 have a high degree of mutational similarity in the AD sequences (see Table 1). In COX II, hot spots occur especially in the region between codon 20 and codon 150 and in particular at codons 20, 22, 68, 71, 74, 90, 95, 110 and 146 (see Table 2). In COX III, codons 64, 76, 92, 121, 131, 148, 241 and 247 appear to be highly variable hot spots.

Mutations observed in COX I gene of Alzheimer's patients

Table 1 below is an example of several mutations and the number of times a given mutation is observed in ten clones of mitochondrial cytochrome c oxidase subunit I (COX I) gene for each of 44 Alzheimer's patients. The mutations listed for the AD patients are relative to the published Cambridge sequences for normal human COX I. The codon number indicated is determined in a conventional manner from the open reading frame at the 5'-end of the gene.

TABLE 1

| Codon # | | 26 | 52 | 52 | 66 | 66 | 84 | 88 | 103 | 109 | 111 | 136 | 155 |
|---|---|---|---|---|---|---|---|---|---|---|---|---|---|
| Normal AA | | Ala | His | His | Ile | Ile | Pro | Gly | Trp | Leu | Leu | Tyr | Val |
| Normal DNA | | GCT | CAC | CAC | ATC | ATC | CCC | GGT | TGA | CTC | CTC | TAC | GTC |
| Observed | | Thr | Tyr | Leu | Val | Thr | Leu | Asp | Arg | Pro | Pro | His | Ile |
| Mutation | | ACT | CCC | CTC | GTC | ACC | CTC | GAT | CGA | CCC | CCC | CAC | ATC |
| AD Patient | | | | | | | | | | | | | |
| #1 | 3A6_KE | | | | | | | 1 | | | | | 2 |
| #2 | 3B1_RI | | | | | | | | | | | | 5 |
| #3 | 3B2_DA | | | | | | | | | | | | |
| #4 | 3B3_WO | | | | | | | | | | | | |
| #5 | 3B4_PI | | | | | | | | | | | | |
| #6 | 3B5_TR | | | | | | | | | | | | |
| #7 | 3B6_CR | | | | | | | | | | | | |
| #8 | 3B7_LF | | | | | | | | | | | | |
| #9 | 3B8_OB | | | | | | | | | | | | |
| #10 | 3C1_GU | | | | | | | | | | | 1 | |
| #11 | 3E3_GE | | | | 1 | | | | | | | | |
| #12 | 3E4_MI | | | | | | | | | | | | |
| #13 | 3E5_BE | | | | | | 1 | | | | | | |
| #14 | 3E6_RE | | | | 1 | | | | | | | | |
| #15 | 3F6_BJ | | | | | | | | | | | | |
| #16 | 3G6_BL | | | | | | | | | | | | |
| #17 | 3G7_SD | | | 1 | | | | | | | | 1 | |
| #18 | 3H1_JY | 1 | | | | | | | | | | | |
| #19 | 3H2_ML | | | | | | | | | | | | |
| #20 | 3H3_HA | | | | | | | | | | | | |
| #21 | 3H5_AS | 1 | | | | | | | | 1 | | | |
| #22 | 3H6_AI | | | | | | | | | | | | |
| #23 | 3I1_AA | | | | | 1 | | | | | | | |
| #24 | 3I2_NU | | | | | | | | | | | | |
| #25 | 3I6_BC | | | | | | | | | | | | |
| #26 | 3I7_DN | | | | | | | | | | 1 | | |
| #27 | 3I8_CO | | | | | | | | | | | | |
| #29 | 3J1_GR | | | | | | | | | | | | |
| #30 | 3J3_HW | | | | | | | | | | 1 | | |
| #31 | 3K2_DM | | | | | | | | | | | | |
| #32 | 3K8_ZI | | | | | | | 1 | | | | | |
| #33 | 3D3_LW | | | | | | | | | | | | |
| #34 | 3D4_AL | | | | | | | | | | | | |
| #35 | 8A5_YA | | | 2 | | | 1 | | | | 1 | | |
| #36 | 8A6_BR | | | | | | | | | 1 | | | |
| #37 | 8A7_SA | | | | | | | | | | | | |
| #38 | 8A8_BA | | | | | | | | | | | | |
| #39 | 8B2_SP | | | | | | | | | | | | |
| #40 | 8D2_MD | | | | | | | 1 | | | | | |
| #41 | 8D3_LC | | | | | | | | | | | | |
| #42 | 8D4_WI | | | | | | | | | | | | |
| #43 | 8D5_JE | | | | | | | | | | | 1 | |
| #44 | 8D6_DE | | | | | | | | | | | | |

| Codon # | | 155 | 167 | 170 | 178 | 193 | 193 | 194 | 200 | 200 | 216 | 221 | 261 |
|---|---|---|---|---|---|---|---|---|---|---|---|---|---|
| Normal AA | | Val | Thr | Asn | Gln | Val | Val | Leu | Pro | Pro | Asn | Asp | Tyr |
| Normal DNA | | GTC | ACA | AAT | CAA | GTC | GTC | CTA | CCA | CCA | AAC | GAC | TAC |
| Observed | | Ala | Ala | Ser | Leu | Ala | Ile | Phe | Pro | Leu | Ser | Asn | Cys |
| Mutation | | GCC | GCA | AGT | CTA | GCC | ATC | TTA | CTA | TCA | GAC | AAC | TGC |
| AD Patient | | | | | | | | | | | | | |
| #1 | 3A6_KE | | | | | | | 1 | | | | | |
| #2 | 3B1_RI | | | | | | | 4 | | | | 1 | |
| #3 | 3B2_DA | | | 1 | 1 | | | | | | | | |
| #4 | 3B3_WO | | | | | | | 1 | | | | | |
| #5 | 3B4_PI | | | 1 | | | | | | | | | |
| #6 | 3B5_TR | | | | | 1 | | | | | | | |
| #7 | 3B6_CR | | | | | | | | | | | | |
| #8 | 3B7_LF | | | | 1 | | | | | 1 | | | |
| #9 | 3B8_OB | | | | | | | | | | | | |
| #10 | 3C1_GU | | | | | | | | | | | | |
| #11 | 3E3_GE | | 1 | | | | | | | | | 1 | |
| #12 | 3E4_MI | | | 1 | | | | | | | | | |
| #13 | 3E5_BE | | | | | | | | | | | | |
| #14 | 3E6_RE | | 1 | | | | | | | | | | |
| #15 | 3F6_BJ | | | | | | | | | | | | |
| #16 | 3G6_BL | | | | | | | | | | | | |
| #17 | 3G7_SD | | | | | | | | | | | | |

TABLE 1-continued

| # | ID | 276 | 330 | 357 | 369 | 415 | 415 | 416 | 456 | 456 | 466 | 468 | 474 | 504 |
|---|---|---|---|---|---|---|---|---|---|---|---|---|---|---|
| #18 | 3H1_JY | | | | | | | | | | | | | |
| #19 | 3H2_ML | | | | | | | | | | | | | |
| #20 | 3H3_HA | | | | | | | | | | | | | |
| #21 | 3H5_AS | | 1 | | | | | | | | | | | |
| #22 | 3H6_AI | | | | | | | | | | | | | 1 |
| #23 | 3I1_AA | | | | | | | | | | | | | |
| #24 | 3I2_NU | | | | | | | | | | | | | |
| #25 | 3I6_BC | | | | | | | | | | | | | |
| #26 | 3I7_DN | | | | | | | | | | | | | |
| #27 | 3I8_CO | | | | | | 1 | | | | | | | |
| #29 | 3J1_GR | | | | | | | | | | | | | |
| #30 | 3J3_HW | | | | | | | | | | | | | |
| #31 | 3K2_DM | | | | | | | | | | | | | |
| #32 | 3K8_ZI | | | | | | | | | | | | | |
| #33 | 3D3_LW | | | | | | | | | | | | | |
| #34 | 3D4_AL | | | | | | | | | | | | | |
| #35 | 8A5_YA | | | | | 1 | | | | | | | | |
| #36 | 8A6_BR | | | | | | | 7 | | | | 1 | | |
| #37 | 8A7_SA | 1 | | | | | | | | | | | | |
| #38 | 8A8_BA | | | 1 | | | | | | | | | | |
| #39 | 8B2_SP | | | | | | 1 | | | | | | | |
| #40 | 8D2_MD | | | | | | | | | | | | | |
| #41 | 8D3_LC | | | | | | | | | | | | | |
| #42 | 8D4_WI | | | | | | | | | | | 1 | | |
| #43 | 8D5_JE | | | | | | | | | | | | | 2 |
| #44 | 8D6_DE | | | | | | | | | | | | 1 | |

| | 276 | 330 | 357 | 369 | 415 | 415 | 416 | 456 | 456 | 466 | 468 | 474 | 504 |
|---|---|---|---|---|---|---|---|---|---|---|---|---|---|
| Codon # | 276 | 330 | 357 | 369 | 415 | 415 | 416 | 456 | 456 | 466 | 468 | 474 | 504 |
| Normal AA | Ala | Ser | Val | Asp | Thr | Thr | Ile | Val | Val | Met | Met | Glu | Thr |
| Normal DNA | GCT | AGC | GTA | GAC | ACT | ACT | ATC | GTA | GTA | ATA | ATA | GAA | ACA |
| Observed | Thr | Gly | Ala | Gly | Ala | Ile | Thr | Ala | Met | Thr | Val | Gly | Ala |
| Mutation | ACT | GGC | GCA | GGC | GCT | ATT | ACC | GCA | ATA | ACA | GTA | GGA | GCA |

AD Patient

| # | ID | 276 | 330 | 357 | 369 | 415 | 415 | 416 | 456 | 456 | 466 | 468 | 474 | 504 |
|---|---|---|---|---|---|---|---|---|---|---|---|---|---|---|
| #1 | 3A6_KE | | | | | 2 | | | | | | | | |
| #2 | 3B1_RI | | | | | 5 | | | | | | | | |
| #3 | 3B2_DA | | | | 1 | | | | | | | | | |
| #4 | 3B3_WO | | | | | 2 | | | | | | | | |
| #5 | 3B4_PI | | | | | | | | | | | | | |
| #6 | 3B5_TR | | | | | | | | | | | | | |
| #7 | 3B6_CR | | | | | | | | 1 | | | | | |
| #8 | 3B7_LF | | | | | | | | | | | | | |
| #9 | 3B8_OB | | 1 | | | | | | | | | | | |
| #10 | 3C1_GU | | | | | | | | | | | | | |
| #11 | 3E3_GE | | | | | | | | 1 | | | | | |
| #12 | 3E4_MI | | | | | | | | | | | | | |
| #13 | 3E5_BE | | | | | | | | | | | | | |
| #14 | 3E6_RE | | | | | | | | | | | | | |
| #15 | 3F6_BJ | | | | | | | | | | 1 | | | |
| #16 | 3G6_BL | | | | | 10 | | | | | | | | |
| #17 | 3G7_SD | | | | | 10 | | | | | | 1 | | |
| #18 | 3H1_JY | | | | | | 1 | | | | | 1 | | |
| #19 | 3H2_ML | | | | | | | 1 | | | | | | |
| #20 | 3H3_HA | | | | | | | | | | | | | |
| #21 | 3H5_AS | | | | | | | | | | | | | |
| #22 | 3H6_AI | | 1 | | | | | | | | 1 | 1 | | |
| #23 | 3I1_AA | | | 1 | | | | | | | 1 | | | 1 |
| #24 | 3I2_NU | | | | | | | | | | | | | |
| #25 | 3I6_BC | | | | | | | | | | | | | |
| #26 | 3I7_DN | | | | 1 | | | | | | | | 1 | |
| #27 | 3I8_CO | | | | | | | | | | 1 | | | 1 |
| #29 | 3J1_GR | | | | | | | | | | | | | |
| #30 | 3J3_HW | | | | | | | | | | | | | |
| #31 | 3K2_DM | | | | | | | | | | | | | |
| #32 | 3K8_ZI | | | | | | | | | | | | | |
| #33 | 3D3_LW | 1 | | | | | | | | | | | | |
| #34 | 3D4_AL | | | | | | | | | | | | | |
| #35 | 8A5_YA | | | | | | | | | | | | | |
| #36 | 8A6_BR | | | | | | | | | | | | | |
| #37 | 8A7_SA | | | | | | | | | | | | | |
| #38 | 8A8_BA | 1 | | | | | | | | | | | | |
| #39 | 8B2_SP | | | | | | | | | | | 1 | | |
| #40 | 8D2_MD | | | | | | | | | | | | | |
| #41 | 8D3_LC | | | | | | | | | | | | | |
| #42 | 8D4_WI | | | | | | | | | | | | | |
| #43 | 8D5_JE | | | | 2 | 1 | | | | | | | | |
| #44 | 8D6_DE | | | | | | | | | | | | | |

As evidenced by Table 1, mutational hot spots of COX I in AD patients are codons 155, 167, 178, 193, 194 and 415. Mutations observed in COX II gene of Alzheimer's patients Table 2 below is an example of several mutations and the number of times a given mutation is observed in ten clones of mitochondrial cytochrome c oxidase subunit II (COX II) gene for each of the 44 Alzheimer's patients. The mutations listed for the AD patients are relative to the published Cambridge sequences for normal human COX II. The codon number indicated is determined in a conventional manner from the open reading frame at the 5'-end of the gene.

TABLE 2

| Codon # | | 20 | 21 | 22 | 25 | 26 | 26 | 61 | 68 | 68 | 70 | 71 | 74 | 74 | 76 | 89 |
|---|---|---|---|---|---|---|---|---|---|---|---|---|---|---|---|---|
| Normal AA | | Leu | Ile | Thr | Asp | His | His | Met | Leu | Leu | Ala | Ile | Val | Val | Ile | Glu |
| Normal DNA | | CTT | ATC | ACC | GAT | CAC | CAC | ATA | CTG | CTG | GCC | ATC | GTC | GTC | ATC | GAG |
| Observed | | Pro | Thr | Ile | Asn | Tyr | Arg | Val | Pro | Phe | Thr | Thr | Ala | Ile | Val | Gly |
| Mutation | | CCT | ACC | ATC | AAT | TAC | CGC | GTA | CCG | TTG | ACC | ACC | GCC | ATC | GTC | GGG |
| AD Patient | | | | | | | | | | | | | | | | |
| #1 | 3A6_KE | | | 2 | | | | | | | | 1 | | | | |
| #2 | 3B1_RI | | | 3 | | | | | | | | | | | | |
| #3 | 3B2_DA | 1 | | 1 | | | | | | | | | | | | |
| #4 | 3B3_WO | | | | | | | | | | | | | | | |
| #5 | 3B4_PI | | 1 | | | | | | | | | 1 | | | | |
| #6 | 3B5_TR | | | | | | | | | | | | | | | |
| #7 | 3B6_CR | | | | | 1 | | | | | | 1 | | | | |
| #8 | 3B7_LF | | | | | | | | | | | | | | | |
| #9 | 3B8_OB | | | | | | | | | | | | | | 1 | |
| #10 | 3C1_GU | | | | | | | | | | | | | | | |
| #11 | 3E3_GE | | | | | | | | | | | | | | | |
| #12 | 3E4_MI | | | | | | | | 1 | | | | | | 1 | |
| #13 | 3E5_BE | | | | | | | | | | | | | | | 1 |
| #14 | 3E6_RE | | | | | | | | | | | | | | | |
| #15 | 3F6_BJ | | | | | | | | | | | | | | | |
| #16 | 3G6_BL | | | | | | | | | | | | | | | |
| #17 | 3G7_SD | | | | | | | | 1 | | | | | | | |
| #18 | 3H1_JY | | 1 | | 1 | | | | | | | | | | | |
| #19 | 3H2_ML | | 1 | | | | | | | | | | | | | |
| #20 | 3H3_HA | | | | | | | | | | | | | | 1 | |
| #21 | 3H5_AS | | | | | | | | | | | | | | | |
| #22 | 3H6_AI | | | | | | | | 1 | | | | | | | |
| #23 | 3I1_AA | | | | | | | | | | | | | | | |
| #24 | 3I2_NU | | | | | | | | | | | | | | | |
| #25 | 3I6_BC | | | | | | | | | | | | | | | |
| #26 | 3I7_DN | | | | 1 | | 1 | | | | | 1 | | | | |
| #27 | 3I8_CO | | | | | | | | | | | | | | | 1 |
| #29 | 3J1_GR | | | | | | | | | | | 1 | | 1 | | |
| #30 | 3J3_HW | | | | | | | | | | | | | | | |
| #31 | 3K2_DM | 1 | | | | | | | | | | | | | | |
| #32 | 3K8_ZI | | | | | | | | | | | | | | | |
| #33 | 3D3_LW | | | | | | | | | | | | | | | |
| #34 | 3D4_AL | | | | | | | | | | | | | | 10 | |
| #35 | 8A5_YA | | | | | | | | | | | | | | | |
| #36 | 8A6_BR | | | | | | | | | | | | | | | |
| #37 | 8A7_SA | 1 | | | | | | | | 10 | | | | | | |
| #38 | 8A8_BA | | | | | 1 | | | | | | | | | | |
| #39 | 8B2_SP | | | | | | | | | | | | | | | |
| #40 | 8D2_MD | | | | | | | | | | | | | | 10 | |
| #41 | 8D3_LC | | | | | | | | | | | | | | | |
| #42 | 8D4_WI | | | | | | | | | | | 1 | | | | |
| #43 | 8D5_JE | | | | | | | | | | | | | | | |
| #44 | 8D6_DE | | | | | | | | | | | | | | | |
| Codon # | | 90 | 95 | 95 | 95 | 110 | 110 | 126 | 146 | 146 | 152 | 157 | 205 | 207 | 224 | 228 |
| Normal AA | | Val | Leu | Lue | Leu | Tyr | Tyr | Phe | Ile | Ile | Met | Gln | Ser | Met | Val | Ter |
| Normal DNA | | GTC | CTT | CTT | CTT | TAC | TAC | TTA | ATT | ATT | ATA | CAA | AGT | ATG | GTA | TAG |
| Observed | | Ile | Phe | Pro | Ile | Cys | His | Leu | Val | Thr | Val | Ter | Gly | Val | Met | Trp |
| Mutation | | ATC | TTT | CCT | ATT | TGC | CAC | CTA | GTT | ACT | GTA | TAA | GGT | GTG | ATA | TGG |
| #1 | 3A6_KE | 8 | 3 | | | | | | 2 | | | | | | | |
| #2 | 3B1_RI | | 2 | | | | | | 2 | | | | | | | |
| #3 | 3B2_DA | | | | | | | | | | | | | | | |
| #4 | 3B3_WO | | | | | | | | | | | | | | | |
| #5 | 3B4_PI | | | | | | | | | | | | | | | |
| #6 | 3B5_TR | | | | | 1 | | | | | | | | | | |
| #7 | 3B6_CR | | | | | | 1 | | | | | | | | | |
| #8 | 3B7_LF | | | | | | | | | | | | | | | |
| #9 | 3B8_OB | | | | | | | | | | | | | | | |
| #10 | 3C1_GU | | | | | | | | | | | | | | | |
| #11 | 3E3_GE | | | | | | | | | | | | | | 10 | |
| #12 | 3E4_MI | | | | | | | | | | | | | | 1 | |

TABLE 2-continued

| # | ID | | | | | | | | | | | |
|---|---|---|---|---|---|---|---|---|---|---|---|---|
| #13 | 3E5_BE | | | | | 1 | | | | | | |
| #14 | 3E6_RE | | | | | | | | | | | |
| #15 | 3F6_BJ | | 1 | | | | | | 1 | 1 | | |
| #16 | 3G6_BL | | | | | | | | | | | |
| #17 | 3G7_SD | | | | | | | 1 | | | | |
| #18 | 3H1_JY | | | | 1 | | | | | | | |
| #19 | 3H2_ML | | | | | | | | | | | |
| #20 | 3H3_HA | | | | | | 1 | | | | | |
| #21 | 3H5_AS | | | | | | | | | | | |
| #22 | 3H6_AI | | | | | | | | | | | |
| #23 | 3I1_AA | | | | | | | | | | | |
| #24 | 3I2_NU | | | | | | 1 | | | | | |
| #25 | 3I6_BC | | | | | | | | | | | |
| #26 | 3I7_DN | | | | | | | | | | | |
| #27 | 3I8_CO | | | | | | | | | | | |
| #29 | 3J1_GR | | | | | | | | | | | |
| #30 | 3J3_HW | | | | | | | | | | | |
| #31 | 3K2_DM | | | | | | | | | | | |
| #32 | 3K8_ZI | | | | | | | | | | | |
| #33 | 3D3_LW | | | | | | | | | | | |
| #34 | 3D4_AL | | | | | | 1 | | | | 1 | |
| #35 | 8A5_YA | | | | | | | | | | 1 | |
| #36 | 8A6_BR | 1 | | 1 | | | | | | | | |
| #37 | 8A7_SA | | | | | | | | | | | |
| #38 | 8A8_BA | | | | | | | | | | | |
| #39 | 8B2_SP | | | | | | | | | | | |
| #40 | 8D2_MD | | | | | | 1 | 1 | | | | |
| #41 | 8D3_LC | | 1 | | | | | | | | | |
| #42 | 8D4_WI | | | | | | | | | | | |
| #43 | 8D5_JE | | | | | | | | | | 1 | |
| #44 | 8D6_DE | 10 | | | | | | | | | | |

As evidenced by Table 2, the mutational hot spots of COX II in AD patients are codons 20, 22, 68, 71, 74, 90, 95, 110 and 146.

At each mutational hot spot, the specific variations noted in AD patients appear universally. For example, at codon 415 in COX I, the normal codon is threonine; each of nine AD mutations observed in codon 415 in COX I codes for alanine. At position 194 in COX I, the aromatic phenylalanine codon replaces the normally hydrophobic leucine. These specific mutations do not occur randomly and are not observed in normal or neurological patients which do not have Alzheimer's disease.

Table 3 below demonstrates the use of the above mutational hot spots in the diagnosis of Alzheimer's disease. For each patient in Table 3, the presence of a mutation at each of codons 155, 167, 178, 193, 194 and 415 of COX I, and each of codons 20, 22, 68, 71, 74, 95, 110 and 146 of COX II is indicated by a shaded box.

Blood samples are obtained and DNA isolated from a number of living subjects that are either clinically-classified AD patients ("Blood/AD") or documented age-matched 'normals' (elderly individuals with no family history of AD or any sign of clinical symptoms of AD) ("Blood/Control"). Of the clinically-classified AD patients ("Blood/AD"), 61% (22 out of 36) have mutations at one or more of the above hot spots. 36% (13 out of 36) contain no mutations. However, as noted above, the diagnosis of probable Alzheimer's disease is presently limited to clinical observation, with definitive analysis accomplished only by pathological examination at autopsy. Moreover, of living patients presently diagnosed as having AD by clinical observation only about 70 to 80% are confirmed to have AD upon autopsy. Tierney, M. C. et al., Neurology 38:359–364 (1988). The remaining 20 to 30% are incorrectly diagnosed as having AD, while they actually have another condition such as senile dementia of the Lewy body variety, Pick's Disease, parasupranuclear palsy, and so forth. Thus, it is expected that a significant percentage of the blood samples taken from living clinically-classified AD patients will not test positive for AD. Indeed, a contrary result is cause for concern.

Of the living documented age-matched normals (Blood/Control) only 1 out of 14 (7%) had a single hot spot mutation. Moreover, it is noted that this individual is 65 years old and may yet develop symptoms of AD.

Brain samples are also harvested and DNA isolated from a number of deceased patients that are confirmed to have AD upon pathological examination at autopsy ("Brain/AD") or deceased documented age matched 'normals' (elderly individuals with no family history of AD, no sign of clinical symptoms of AD during life, and no sign of AD upon pathological examination at autopsy) ("Brain/Control"). Brain samples are also harvested and DNA isolated from a number of deceased patients that are diagnosed upon autopsy to have other degenerative neurologic disorders selected from Huntington's disease ("Brain/HD"), non-specific degenerative disease ("Brain/NSD"), parasupranuclear palsy ("Brain/PSP"), Pick's disease (Brain/Picks"), Hallervorden Spatz ("Brain/HSP"), diffuse Lewy body disease ("Brain/DLBD"), atypical tangles ("Brain/AT"), argyrophyllic grains ("Brain/AG"), senile dementia of the Lewy body variety ("Brain/LBV").

Results from the DNA isolated from brain samples clearly illustrate the specificity of the diagnostic technique of the present invention. Of the brain samples taken from individuals with pathologically confirmed AD, 83% (10 or 12) contained one or more hot spot mutations. Of the two remaining individuals (BA and DE), BA demonstrated mutations at COX I codons 170 and 276 and COX II codon 26, while DE demonstrated mutations at COX I codon 221 and COX II codon 90. Accordingly, it may be desirable to extend to above list of hot spots. In contrast, none of the age matched 'normals' are found to contain such mutations.

In addition, of the individuals having other neurologic disorders, only 2 of 18 (11%) contained a single mutation. This illustrates that the diagnosis of the present invention is specific to AD. Moreover, pathologists involved with the autopsy of one of the two individuals (SC) are unable to definitively clearly differentiate the dementia with argyrophyllic grains from AD. Finally, one cannot rule out the possibility that the other individual (KI) would have manifested symptoms of AD if the individual had not succumbed to Para-Supranuclear Palsy.

TABLE 3

| Codon | 155 | 167 | 178 | 193 | 194 | 415 | 415 | 20 | 22 | 68 | 71 | 74 | 95 | 110 | 110 | 146 | 146 |
|---|---|---|---|---|---|---|---|---|---|---|---|---|---|---|---|---|---|
| Wild-type Amino Acid | Val | Thr | Gln | Val | Leu | Thr | Thr | Leu | Thr | Leu | Ile | Val | Leu | Tyr | Tyr | Ile | Ile |
| Wild-type DNA | GTT | ACA | CAA | GTC | CTA | ACT | ACT | CTT | ACC | CTG | ATC | GTC | CTT | TAC | TAC | ATT | ATT |
| Observed Amino Acid | Ile | Ala | Leu | Ala | Phe | Ala | Ile | Pro | Ile | Pro | Thr | Ile | Phe | Cys | His | Thr | Val |
| Observed DNA | ATC | GCA | CTA | GCC | TTA | GCT | ATT | CCT | ATC | CCG | ACC | ATC | TTT | TGC | CAC | ACT | GTT |

| Patient # | Source | 155 | 167 | 178 | 193 | 194 | 415 | 415 | 20 | 22 | 68 | 71 | 74 | 95 | 110 | 110 | 146 | 146 |
|---|---|---|---|---|---|---|---|---|---|---|---|---|---|---|---|---|---|---|
| 1KE | Blood/AD | ■ | | | | ■ | ■ | | | ■ | | | | ■ | | | | ■ |
| 2RI | Blood/AD | ■ | | | | ■ | ■ | | | ■ | | | | ■ | | | | ■ |
| 3DA | Blood/AD | | | ■ | | | | | | | | | | | | | | |
| 4WO | Blood/AD | | | | | ■ | ■ | | | | | | | | | | | |
| 5PI | Blood/AD | | | | | | | | | | | | | ■ | | | | |
| 6TR | Blood/AD | | | | ■ | | | | | | | | | | | ■ | | |
| 7LF | Blood/AD | | | ■ | | | | | | | | | | | | | | |
| 8OB | Blood/AD | | | | | | | | | | | | ■ | | | | | |
| 9GE | Blood/AD | ■ | | | | | | | | | | | | | | | | |
| 10RE | Blood/AD | ■ | | | | | | | | | | | | | | | | |
| 11BJ | Blood/AD | | | | | | | | | | | | | | ■ | | | |
| 12ML | Blood/AD | | | | | | | | | | | | | | | | | |
| 13HA | Blood/AD | | | | | | | | | | | | ■ | | | | | |
| 15AS | Blood/AD | ■ | | | | | | | | | | | | | | | | |
| 16CR | Blood/AD | | | | | | | | | | | | ■ | | | ■ | | |
| 17CO | Blood/AD | | | | ■ | | | | | | | | | | | | | |
| 18DM | Blood/AD | | | | | | | | | ■ | | | | | | | | |
| 19JY | Blood/AD | | | | | | | | | | ■ | | | | | | | ■ |
| 20MI | Blood/AD | | | | | | | | | | | | | | | | | |
| 21BE | Blood/AD | | | | | | | | | | | | | | | | | |
| 22SJ | Blood/AD | | | | | | | | | | | | | ■ | | | | |
| 23WY | Blood/AD | | | | ■ | | | | | | | | | ■ | ■ | | | |
| 24KP | Blood/AD | | | | ■ | | | | | | | | | | ■ | | | |
| 25BL | Blood/AD | | | | | ■ | | | | | | | | | | | | |
| 26SD | Blood/AD | | | | | | | | | | ■ | | | | | | | |
| 27HU | Blood/Control | | | | | | | | | | | | | | | | | |
| 28UT | Blood/Control | ■ | | | | | | | | | | | | | | | | |
| 29OD | Blood/Control | | | | | | | | | | | | | | | | | |
| 30SO | Blood/Control | | | | | | | | | | | | | | | | | |
| 31KA | Blood/Control | | | | | | | | | | | | | | | | | |
| 32SH | Blood/Control | | | | | | | | | | | | | | | | | |
| 33GA | Blood/Control | | | | | | | | | | | | | | | | | |
| 34GK | Blood/Control | | | | | | | | | | | | | | | | | |
| 35GT | Blood/Control | | | | | | | | | | | | | | | | | |
| 36GL | Blood/Control | | | | | | | | | | | | | | | | | |
| 37GM | Blood/Control | | | | | | | | | | | | | | | | | |
| 38EA | Blood/Control | | | | | | | | | | | | | | | | | |
| 39BK | Blood/Control | | | | | | | | | | | | | | | | | |
| 40JV | Blood/Control | | | | | | | | | | | | | | | | | |
| 41DR | Blood/Control | | | | | | | | | | | | | | | | | |
| 42AI | Blood/AD | | | | | | | | | | | | | | | | | |
| 45AA | Blood/AD | | | | | | | | | | | | | | | | | |
| 46NU | Blood/AD | | | | | | | | | | | | | | | | | |
| 47CN | Blood/AD | | | | | | | | | | | | | | | | | |
| 48BC | Blood/AD | | | | | | | | | | | | | | | | | |
| 49DN | Blood/AD | | | | | | | | | | | | | | | | | |
| 50GR | Blood/AD | | | | | | | | | | | | | | | | | |
| 51HW | Blood/AD | | | | | | | | | | | | | | | | | |
| 52HB | Blood/AD | | | | | | | | | | | | | | | | | |
| 54Z1 | Blood/AD | | | | | | | | | | | | | | | | | |
| 55GU | Blood/AD | | | | | | | | | | | | | | | | | |

| Codon | 155 | 167 | 178 | 193 | 193 | 194 | 415 | 20 | 22 | 68 | 71 | 74 | 90 | 95 | 95 | 110 | 146 |
|---|---|---|---|---|---|---|---|---|---|---|---|---|---|---|---|---|---|
| Wild-type Amino Acid | Val | Thr | Gln | Val | Val | Leu | Thr | Leu | Thr | Leu | Ile | Val | Val | Leu | Leu | Tyr | Ile |
| Wild-type DNA | GTT | ACA | CAA | GTC | GTC | CTA | ACT | CTT | ACC | CTG | ATC | GTC | GTC | CTT | CTT | TAC | ATT |
| Observed Amino Acid | Ala | Ala | Leu | Ile | Ala | Phe | Ala | Pro | Ile | Phe | Thr | Ile | Ile | Ile | Pro | Cys | Val |
| Observed DNA | GCC | GCA | CTA | ATC | GCC | TTA | GCT | CCT | ATC | TTG | ACC | ATC | ATC | ATT | CCT | CAC | GTT |

| Patient # | Source | 155 | 167 | 178 | 193 | 193 | 194 | 415 | 20 | 22 | 68 | 71 | 74 | 90 | 95 | 95 | 110 | 146 |
|---|---|---|---|---|---|---|---|---|---|---|---|---|---|---|---|---|---|---|
| 55AL | Brain/AD | | | | | | | | | | | | ■ | | | | | |
| 56LW | Brain/AD | | | | | | | | | | | | | | | | | |

TABLE 3-continued

| Sample | Type |
|---|---|
| 57YA | Brain/AD |
| 58Br | Brain/AD |
| 59SA | Brain/AD |
| 60BA | Brain/AD |
| 61SP | Brain/AD |
| 62MD | Brain/AD |
| 63LC | Brain/AD |
| 65WI | Brain/AD |
| 66JE | Brain/AD |
| 67DE | Brain/AD |
| 68LO | Brain/Control |
| 69LA | Brain/Control |
| 70UN | Brain/HD |
| 71GO | Brain/NSD |
| 72KO | Brain/PSP |
| 73QU | Brain/Picks |
| 74OO | Brain/HSP |
| 75PU | Brain/DLBD |
| 76WE | Brain/Control |
| 771KI | Brain/PSP |
| 78SI | Brain/DLBD |
| 79DX | Brain/AT |
| 80SN | Brain/Control |
| 81LL | Brain/DLBD |
| 82KK | Brain/DLBD |
| 83IA | Brain/DIBD |
| 84SC | Brain/AG/AD |
| 85MC | Brain/LBV |
| 86NI | Brain/LBV |
| 87MO | Brain/LBV |
| 88RS | Brain/LBV |
| 89BS | Brain/LBV |

The invention also includes the isolated nucleotide sequences which correspond to or are complementary to portions of mitochondrial cytochrome c oxidase genes which contain gene mutations that correlate with the presence of Alzheimer's disease. The isolated nucleotide sequences which contain gene mutations include COX I nucleotides 5964 to 7505, COX II nucleotides 7646 to 8329 and COX III nucleotides 9267 to 10052.

Diagnostic Detection of Alzheimer's Disease-Associated Mutations:

According to the present invention, base changes in the mitochondrial COX genes can be detected and used as a diagnostic for Alzheimer's disease. A variety of techniques are available for isolating DNA and RNA and for detecting mutations in the isolated mitochondrial COX genes.

A number of sample preparation methods are available for isolating DNA and RNA from patient blood samples. For example, the DNA from a blood sample is obtained by cell lysis following alkali treatment. Often, there are multiple copies of RNA message per DNA. Accordingly, it is useful from the standpoint of detection sensitivity to have a sample preparation protocol which isolates both forms of nucleic acid. Total nucleic acid may be isolated by guanidium isothiocyanate/phenol-chloroform extraction, or by proteinase K/phenol-chloroform treatment. Commercially available sample preparation methods such as those from Qiagen Inc. (Chatsworth, Calif.) can also be utilized.

As discussed more fully hereinbelow, hybridization with one or more labelled probes containing complements of the variant sequences enables detection of the AD mutations. Since each AD patient can be heteroplasmic (possessing both the AD mutation and the normal sequence) a quantitative or semi-quantitative measure (depending on the detection method) of such heteroplasmy can be obtained by comparing the amount of signal from the AD probe to the amount from the AD⁻ (normal or wild-type) probe.

A variety of techniques, as discussed more fully hereinbelow, are available for detecting the specific mutations in the mitochondrial COX genes. The detection methods include, for example, cloning and sequencing, ligation of oligonucleotides, use of the polymerase chain reaction and variations thereof, use of single nucleotide primer-guided extension assays, hybridization techniques using target-specific oligonucleotides and sandwich hybridization methods.

Cloning and sequencing of the COX genes can serve to detect AD mutations in patient samples. Sequencing can be carried out with commercially available automated sequencers utilizing fluorescently labelled primers. An alternate sequencing strategy is the "sequencing by hybridization" method using high density oligonucleotide arrays on silicon chips (Fodor et al., *Nature* 364:555–556 (1993); Pease et al., *Proc. Natl. Acad. Sci. USA*, 91:5022–5026 (1994). For example, fluorescently-labelled target nucleic acid generated, for example from PCR amplification of the target genes using fluorescently labelled primers, are hybridized with a chip containing a set of short oligonucleotides which probe regions of complementarily with the target sequence. The resulting hybridization patterns are useful for reassembling the original target DNA sequence.

Mutational analysis can also be carried out by methods based on ligation of oligonucleotide sequences which anneal immediately adjacent to each other on a target DNA or RNA molecule (Wu and Wallace, *Genomics* 4:560–569 (1989); Landren et al., *Science* 241:1077–1080 (1988); Nickerson et al., *Proc. Natl. Acad. Sci.* 87:8923–8927 (1990); Barany, F., *Proc. Natl. Acad. Sci.* 88:189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating AD mutation loci. The elevated reaction temperatures permits the ligation reaction to be conducted with high stringency (Barany, F., *PCR Methods and Applications* 1: 15–16 (1991)).

Analysis of point mutations in DNA can also be carried out by using the polymerase chain reaction (PCR) and variations thereof. Mismatches can be detected by competitive oligonucleotide priming under hybridization conditions where binding of the perfectly matched primer is favored (Gibbs et al., *Nucl. Acids. Res.* 17:2437–2448 (1989)). In the amplification refractory mutation system technique (ARMS), primers are designed to have perfect matches or mismatches with target sequences either internal or at the 3' residue (Newton et al., *Nucl. Acids. Res.* 17:2503–2516 (1989)). Under appropriate conditions, only the perfectly annealed oligonucleotide functions as a primer for the PCR reaction, thus providing a method of discrimination between normal and mutant (AD) sequences.

Genotyping analysis of the COX genes can also be carried out using single nucleotide primer-guided extension assays, where the specific incorporation of the correct base is provided by the high fidelity of the DNA polymerase (Syvanen et al., *Genomics* 8:684–692 (1990); Kuppuswamy et al., *Proc. Natl. Acad. Sci. U.S.A.* 88:1143–1147 (1991)). Another primer extension assay, which allows for the quantification of heteroplasmy by simultaneously interrogating both wild-type and mutant nucleotides, is disclosed in a co-pending U.S. patent application entitled, "Multiplexed Primer Extension Methods", naming Eoin Fahy and Soumitra Ghosh as inventors, filed on Mar. 24, 1995; serial number to be assigned, the disclosure of which is incorporated by reference.

Detection of single base mutations in target nucleic acids can be conveniently accomplished by differential hybridization techniques using target-specific oligonucleotides (Suggs et al., *Proc. Natl. Acad. Sci.* 78:6613–6617 (1981); Conner et al., *Proc. Natl. Acad. Sci.* 80:278–282 (1983); Saiki et al., *Proc. Natl. Acad. Sci.* 86:6230–6234 (1989)). For example, mutations are diagnosed on the basis of the higher thermal stability of the perfectly matched probes as compared to the mismatched probes. The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

An alternative strategy involves detection of the COX genes by sandwich hybridization methods. In this strategy, the mutant and wild-type (normal) target nucleic acids are separated from non-homologous DNA/RNA using a common capture oligonucleotide immobilized on a solid support and detected by specific oligonucleotide probes tagged with reporter labels. The capture oligonucleotides can be immobilized on microtitre plate wells or on beads (Gingeras et al., *J. Infect. Dis.* 164:1066–1074 (1991); Richman et al., *Proc. Natl. Acad. Sci.* 88:11241–11245 (1991)).

While radio-isotopic labeled detection oligonucleotide probes are highly sensitive, non-isotopic labels are preferred due to concerns about handling and disposal of radioactivity. A number of strategies are available for detecting target nucleic acids by non-isotopic means (Matthews et al., *Anal. Biochem.*, 169:1–25 (1988)). The non-isotopic detection method may be direct or indirect.

The indirect detection process is generally where the oligonucleotide probe is covalently labelled with a hapten or ligand such as digoxigenin (DIG) or biotin. Following the hybridization step, the target-probe duplex is detected by an antibody- or streptavidin-enzyme complex. Enzymes commonly used in DNA diagnostics are horseradish peroxidase and alkaline phosphatase. One particular indirect method, the Genius™ detection system (Boehringer Mannheim) is especially useful for mutational analysis of the mitochondrial COX genes. This indirect method uses digoxigenin as the tag for the oligonucleotide probe and is detected by an anti-digoxigenin-antibody-alkaline phosphatase conjugate.

Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes. Examples of lanthanide chelates include complexes of $Eu^{3+}$ and $Tb^{3+}$. Directly labeled oligonucleotide-enzyme conjugates are preferred for detecting point mutations when using target-specific oligonucleotides as they provide very high sensitivities of detection.

Oligonucleotide-enzyme conjugates can be prepared by a number of methods (Jablonski et al., *Nucl. Acids Res.,* 14:6115–6128 (1986); Li et al., *Nucl. Acids Res.* 15:5275–5287 (1987); Ghosh et al., *Bioconjugate Chem.* 1: 71–76 (1990)), and alkaline phosphatase is the enzyme of choice for obtaining high sensitivities of detection. The detection of target nucleic acids using these conjugates can be carried out by filter hybridization methods or by bead-based sandwich hybridization (Ishii et al., *Bioconjugate Chemistry* 4:34–41 (1993)).

Detection of the probe label may be accomplished by the following approaches. For radioisotopes, detection is by autoradiography, scintillation counting or phosphor imaging. For hapten or biotin labels, detection is with antibody or streptavidin bound to a reporter enzyme such as horseradish peroxidase or alkaline phosphatase, which is then detected by enzymatic means. For fluorophor or lanthanide-chelate labels, fluorescent signals may be measured with spectrofluorimeters with or without time-resolved mode or using automated microtitre plate readers. With enzyme labels, detection is by color or dye deposition (p-nitrophenyl phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g. 4-methyl umbelliferyl phosphate for alkaline phosphatase) or chemiluminescence (the alkaline phosphatase dioxetane substrates LumiPhos 530 from Lumigen Inc., Detroit Mich. or AMPPD and CSPD from Tropix, Inc.). Chemiluminescent detection may be carried out with X-ray or polaroid film or by using single photon counting luminometers. This is the preferred detection format for alkaline phosphatase labelled probes.

The oligonucleotide probes for detection preferably range in size between 10 and 100 bases, more preferably between 15 and 30 bases in length. Examples of such nucleotide probes are found below in Tables 4 and 5. Tables 4 and 5 provide representative sequences of probes for detecting mutations in COX genes and representative antisense sequences. In order to obtain the required target discrimination using the detection oligonucleotide probes, the hybridization reactions are preferably run between 20° C. and 60° C., and more preferably between 30° C. and 55° C. As known to those skilled in the art, optimal discrimination between perfect and mismatched duplexes can be obtained by manipulating the temperature and/or salt concentrations or inclusion of formamide in the stringency washes.

TABLE 4

Sense Probes -- DNA detection of antisense strand

| GENE | AA NO. | LENGTH (WT) | % GC | WILD-TYPE | SEQ. ID. NO. | MUTANT | SEQ. ID. NO. |
|---|---|---|---|---|---|---|---|
| COXI | 155 | 23 | 52.2 | 5'-ACCTAGCAGGTGTCTCCTCTATC-3' | 4 | 5'-ACCTAGCAGGTATCTCCTCTATCT-3' | 18 |
| COXI | 167 | 27 | 22.2 | 5'-CAATTTCATCACAACAATTATCAATAT-3' | 5 | 5'-CAATTTCATCACAGCAATTATCAATAT-3' | 19 |
| COXI | 178 | 21 | 47.6 | 5'-GCCATAACCCAATACCAAACG-3' | 6 | 5'-GCCATAACCCTATACCAAACG-3' | 20 |
| COXI | 193 | 23 | 47.8 | 5'-AATCACAGCAGTCCTACTTCTCC-3' | 7 | 5'-AATCACAGCAGCCTACTTCTCC-3' | 21 |
|  |  |  |  |  |  | 5'-AATCACAGCAATCCTACTTCTCC-3' | 22 |
| COXI | 194 | 25 | 50.0 | 5'-TCACAGCAGTCCTACTTCTCCTATC-3' | 8 | 5'-TCACAGCAGTCTTACTTCTCCTATC-3' | 23 |
| COXI | 415 | 26 | 26.9 | 5'-CAAAATCCATTTCACTATCATATTCA-3' | 9 | 5'-AAAATCCATTTCGCTATCATATTCA-3' | 24 |
| COXII | 20 | 25 | 37.5 | 5'-TCATAGAAGAGCTTATCACCTTTCA-3' | 10 | 5'-TCATAGAAGAGCCTATCACCTTTCA-3' | 25 |
| COXII | 22 | 25 | 37.5 | 5'-AGAGCTTATCACCCTTTCATGATCA-3' | 11 | 5'-AGAGCTTATCATCTTTCATGATCA-3' | 26 |
| COXII | 68 | 18 | 61.1 | 5'-TGCCCGCCATCATCCTAG-3' | 12 | 5'-TGAACTATCTTGCCCGCC-3' | 27 |
| COXII | 71 | 18 | 61.1 | 5'-TGCCCGCCATCATCCTAG-3 | 13 | 5'-TGCCCGCCACCATCCTAG-3' | 28 |
| COXII | 74 | 21 | 52.4 | 5'-ATCATCCTAGTCCTCATCGCC-3' | 14 | 5'-ATCATCCTAATCCTCATCGCC-3' | 29 |
| COXII | 95 | 21 | 47.6 | 5'-GATCCCTCCCTTACCATCAAA-3' | 15 | 5'-GATCCCTCCTTTACCATCAAAT-3' | 30 |
|  |  |  |  |  |  | 5'-GATCCCTCCCCIACCATCAAA-3' | 31 |
| COXII | 110 | 23 | 52.2 | 5'-AACCTACGAGACACCGACTACG-3' | 16 | 5'-AACCTACGAGCACACCGACTAC-3' | 32 |
|  |  |  |  |  |  | 5'-AACCTACGAGTGCACCGACTAC-3' | 33 |
| COXII | 146 | 20 | 55.0 | 5'-AGTACTCCCGATTGAAGCCC-3' | 17 | 5'-AGTACCCGGTTGAAGCCC-3' | 34 |

TABLE 5

Antisense Probes -- DNA and RNA detection of sense sequence

| GENE | AA NO. | LENGTH (WT) | % GC | WILD-TYPE | SEQ. ID. NO. | MUTANT | SEQ. ID. NO. |
|---|---|---|---|---|---|---|---|
| COXI | 155 | 23 | 52.2 | 5'-GATAGAGGAGACACCTGCTAGGT-3' | 35 | 5'-AGATAGAGGAGATACCTGCTAGGT-3' | 49 |
| COXI | 167 | 27 | 22.2 | 5'-ATATTGATAATTGTTGTAGATGAAATTG-3' | 36 | 5'-ATATTGATAATTGCTGTGATGAAATTG-3' | 50 |
| COXI | 178 | 21 | 47.6 | 5'-CGTTTGGTATTGGGTTATGGC-3' | 37 | 5'-CGTTTGGTATAGGGTTATGGC-3' | 51 |
| COXI | 193 | 23 | 47.8 | 5'-GGAGAAGTAGGACTGCTGTGATT-3' | 38 | 5'-GGAGAAGTAGGGCTGCTGTGATT-3' | 52 |
|  |  |  |  |  |  | 5'-GGAGAAGTAGGATTGCTGTGATT-3' | 53 |
| COXI | 194 | 25 | 50.0 | 5'-GATAGGAGAAGTAGGACTGCTGTGA-3' | 39 | 5'-GATAGGAGAAGTAAGACTGCTGTGA-3' | 54 |
| COXI | 415 | 26 | 26.9 | 5'-TGAATATGATAGTGAAATGGATTTTG-3' | 40 | 5'-TGAATATGATAGCGAAATGGATTTT-3' | 55 |
| COXII | 20 | 25 | 37.5 | 5'-TGAAAGGTGATAAGCTCTTCTATGA-3' | 41 | 5'-TGAAAGGTGATAGGCTCTTCTATGA-3' | 56 |
| COXII | 22 | 24 | 37.5 | 5'-TGATCATGAAAGGTGATAAGCTCTT-3' | 42 | 5'-TGATCATGAAAGATGATAAGCTCT-3' | 57 |
| COXII | 68 | 18 | 61.1 | 5'-GGCGGGCAGGATAGTTCA-3' | 43 | 5'-GGCGGGCAAGATAGTTCA-3' | 58 |
| COXII | 71 | 18 | 61.1 | 5'-CTAGGATGATGGCGGGCA-3' | 44 | 5'-GGCGGGCAAGATAGTTCA-3' | 59 |
| COXII | 74 | 21 | 52.4 | 5'-GGCGATGACCACTAGGATGAT-3' | 45 | 5'-GGCGATGAGGATTAGGATGAT-3' | 60 |
| COXII | 95 | 21 | 47.6 | 5'-TTTGATGGTAAGGGAGGGATC-3' | 46 | 5'-ATTTGATGGTAAAGGAGGGATC-3' | 61 |
|  |  |  |  |  |  | 5'-TTTGATGGTAGGGGAGGGATC-3' | 62 |

TABLE 5-continued

Antisense Probes -- DNA and RNA detection of sense sequence

| GENE | AA NO. | LENGTH (WT) | % GC | WILD-TYPE | SEQ. ID. NO. | MUTANT | SEQ. ID. NO. |
|---|---|---|---|---|---|---|---|
| COXII | 110 | 23 | 52.2 | 5'-CGTAGTCGGTGTACTCGTAGGTT-3' | 47 | 5'-GTAGTCGGTCTGCTCGTAGGTT-3' | 63 |
| COXII | 110 | 23 | 52.2 | | | 5'-GTAGTCGGTGCACTCGTAGGTT-3' | 64 |
| COXII | 146 | 20 | 55.0 | 5'-GGGCTTCAATCGGGAGTACT-3' | 48 | 5'-GGGCTCAACCGGGAGTACT-3' | 65 |

As an alternative to detection of mutations in the nucleic acids associated with the COX genes, it is also possible to analyze the protein products of the COX genes. In particular, point mutations in cytochrome c oxidase subunits 1 and 2 are expected to alter the structure of the proteins for which these gene encode. These altered proteins (variant polypeptides) can be isolated and used to prepare antisera and monoclonal antibodies that specifically detect the products of the mutated genes and not those of non-mutated or wild-type genes. Mutated gene products also can be used to immunize animals for the production of polyclonal antibodies. Recombinantly produced peptides can also be used to generate polyclonal antibodies. These peptides may represent small fragments of gene products produced by expressing regions of the mitochondrial genome containing point mutations.

More particularly, as discussed, for example, in PCT/US93/10072, variant polypeptides from point mutations in cytochrome c oxidase subunits 1 and 2 can be used to immunize an animal for the production of polyclonal antiserum. For example, a recombinantly produced fragment of a variant polypeptide can be injected into a mouse along with an adjuvant so as to generate an immune response. Murine immunoglobulins which bind the recombinant fragment with a binding affinity of at least $1 \times 10^7$ M$^{-1}$ can be harvested from the immunized mouse as an antiserum, and may be further purified by affinity chromatography or other means. Additionally, spleen cells are harvested from the mouse and fused to myeloma cells to produce a bank of antibody-secreting hybridoma cells. The bank of hybridomas can be screened for clones that secrete immunoglobulins which bind the recombinantly produced fragment with an affinity of at least $1 \times 10^6$ M$^{-1}$. More specifically, immunoglobulins that selectively bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides can be formed from a variety of different polynucleotides (genomic or cDNA, RNA, synthetic oligonucleotides, etc.) as well as by a variety of different techniques.

The DNA sequences can be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors can contain selection markers (e.g., markers based on tetracyclinic resistance or hygromycin resistance) to permit detection and/or selection of those cells transformed with the desired DNA sequences. Further details can be found in U.S. Pat. No. 4,704,362.

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

E. coli is one prokaryotic host useful particularly for cloning DNA sequences of the present invention. Other microbial hosts suitable for use include bacilli, such as Bacillus subtilus, and other enterobacteriaceae, such as Salmonella, Serratia, and various Pseudomonas species. In these prokaryotic hosts one can also make expression vectors, which will typically contain expression control sequences compatible with the host cell (e.g. an origin of replication). In addition, any number of a variety of well-known promoters will be present, such as the lactose promoter system a tryptophan (Trp) promoter system, a beta-lactamase promoter system, or a promoter system from phage lambda. The promoters will typically control expression, optionally with an operator sequence, and have ribosome binding site sequences, for example, for initiating and completing transcription and translation.

Other microbes, such as yeast, may also be used for expression. Saccharomyces can be a suitable host, with suitable vectors having expression control sequences, such as promoters, including 3-phosphoglycerate kinase or other glycolytic enzymes, and an origin of replication, termination sequences, etc. as desired.

In addition to microorganisms, mammalian tissue cell culture may also be used to express and produce the polypeptides of the present invention. Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, and so forth. The vectors containing the DNA segments of interest (e.g., polypeptides encoding a variant polypeptide) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

The method lends itself readily to the formulation of test kits which can be utilized in diagnosis. Such a kit would comprise a carrier compartmentalized to receive in close confinement one or more containers wherein a first container may contain suitably labeled DNA probes. Other containers may contain reagents useful in the localization of the labeled probes, such as enzyme substrates Still other containers may contain restriction enzymes, buffers etc., together with instructions for use.

Therapeutic treatment of Alzheimer's Disease:

Suppressing the effects of the mutations through antisense technology provides an effective therapy for AD. Much is known about 'antisense' therapies targeting messenger RNA (mRNA) or nuclear DNA. Helene et al., *Biochem. Biophys. Acta* 1049:99–125 (1990). The diagnostic test of the present invention is useful for determining which of the specific AD mutations exist in a particular AD patient; this allows for "custom" treatment of the patient with antisense oligonucleotides only for the detected mutations. This patient-specific antisense therapy is also novel, and minimizes the exposure of the patient to any unnecessary antisense therapeutic treatment. As used herein, an "antisense" oligonucleotide is one that base pairs with single stranded DNA or RNA by Watson-Crick base pairing and with duplex target DNA via Hoogsteen hydrogen bonds.

Without wishing to be held to any particular theory, it has been postulated that the destructive effects of mutations in the cytochrome c oxidase gene arise from the production of the radicals due to faults in the election transport chain. The effects of such free radicals is expected to be cumulative, especially in view of the lack of mechanisms for suppressing V mutations in mitochondria.

The destructive effect of the AD mutations in cytochrome c oxidase genes is preferably reduced or eliminated using antisense oligonucleotide agents. Such antisense agents target mitochondrial DNA, by triplex formation with double-stranded DNA, by duplex formation with single-stranded DNA during transcription, or both. In a preferred embodiment, antisense agents target messenger RNA coding for the mutated cytochrome c oxidase gene(s). Since the sequences of both the DNA and the mRNA are the same, it is not necessary to determine accurately the precise target to account for the desired effect. Procedures for inhibiting gene expression in cell culture and in vivo can be found, for example, in C. F. Bennett, et al. *J. Liposome Res.*, 3:85 (1993) and C. Wahlestedt, et al. *Nature,* 363:260 (1993).

Antisense oligonucleotide therapeutic agents demonstrate a high degree of pharmaceutical specificity. This allows the combination of two or more antisense therapeutics at the same time, without increased cytotoxic effects. Thus, when a patient is diagnosed as having two or more AD mutations in COX genes, the therapy is preferably tailored to treat the multiple mutations simultaneously. When combined with the present diagnostic test, this approach to "patient-specific therapy" results in treatment restricted to the specific mutations detected in a patient. This patient-specific therapy circumvents the need for 'broad spectrum' antisense treatment using all possible mutations. The end result is less costly treatment, with less chance for toxic side effects.

One method to inhibit the synthesis of proteins is through the use of antisense or triplex oligonucleotides, analogues or expression constructs. These methods entail introducing into the cell a nucleic acid sufficiently complementary in sequence so as to specifically hybridize to the target gene or to mRNA. In the event that the gene is targeted, these methods can be extremely efficient since only a few copies per cell are required to achieve complete inhibition. Antisense methodology inhibits the normal processing, translation or half-life of the target message. Such methods are well known to one skilled in the art.

Antisense and triplex methods generally involve the treatment of cells or tissues with a relatively short oligonucleotide, although longer sequences can be used to achieve inhibition. The oligonucleotide can be either deoxyribo- or ribonucleic acid and must be of sufficient length to form a stable duplex or triplex with the target RNA or DNA at physiological temperatures and salt concentrations. It should also be sufficiently complementary or sequence specific to specifically hybridize to the target nucleic acid. Oligonucleotide lengths sufficient to achieve this specificity are preferably about 10 to 60 nucleotides long, more preferably about 10 to 20 nucleotides long. However, hybridization specificity is not only influenced by length and physiological conditions but may also be influenced by such factors as GC content and the primary sequence of the oligonucleotide. Such principles are well known in the art and can be routinely determined by one who is skilled in the art.

As an example, many of the oligonucleotide sequences used in connection with probes in Tables 4 and 5 can also be used as antisense agents, directed to either the mitochondrial DNA or resultant messenger RNA.

A great range of antisense sequences can be designed for a given mutation. For example, oligonucleotide sequences can be selected from the following list to function as RNA and DNA antisense sequences for the mutant mitochondrial gene COX1, Codon 193.

As can be seen, permutations can be generated for a selected mutant antigene by truncating the 5' end, truncating the '3 end, extending the 5' end, or extending the 3' end. Both light chain and heavy chain mtDNA can be targeted. Other variations such as truncating the 5' end and truncating the 3' end, extending the 5' end and extending the 3' end, and truncating the 5' end and extending the 3' end, extending the 5' end and truncating the 3' end, and so forth are possible.

```
Antigene to heavy chain mtDNA, wild-type sequence:

SEQ ID NO: 7       5'-AAT CAC AGC AGT CCT ACT TCT CC

Antigene to heavy chain mtDNA, mutant sequence:

SEQ ID NO: 21      5'-AAT CAC AGC AGC CCT ACT TCT CC

3' truncation:

SEQ ID NO: 66      5'-AAT CAC AGC AGC CCT ACT TCT C

SEQ ID NO: 67      5'-AAT CAC AGC AGC CCT ACT TCT
```

-continued

```
SEQ ID NO: 68      5'-AAT CAC AGC AGC CCT ACT TC
SEQ ID NO: 69      5'-AAT CAC AGC AGC CCT ACT T
SEQ ID NO: 70      5'-AAT CAC AGC AGC CCT ACT
SEQ ID NO: 71      5'-AAT CAC AGC AGC CCT AC
SEQ ID NO: 72      5'-AAT CAC AGC AGC CCT A
       5' truncation:
SEQ ID NO: 73      5'-AT CAC AGC AGC CCT ACT TCT CC
SEQ ID NO: 74      5'-T CAC AGC AGC CCT ACT TCT CC
SEQ ID NO: 75      5'-CAC AGC AGC CCT ACT TCT CC
SEQ ID NO: 76      5'-AC AGC AGC CCT ACT TCT CC
SEQ ID NO: 77      5'-C AGC AGC CCT ACT TCT CC
SEQ ID NO: 78      5'-AGC AGC CCT ACT TCT CC
       3' and 5' truncation:
SEQ ID NO: 79      5'-AT CAC AGC AGC CCT ACT TCT C
SEQ ID NO: 80      5'-T CAC AGC AGC CCT ACT TCT
SEQ ID NO: 81      5'-CAC AGC AGC CCT ACT TC
SEQ ID NO: 82      5'-AC AGC AGC CCT ACT T
       5' and 3' extension
SEQ ID NO: 83      5'-C CGT CCT AAT CAC AGC AGC CCT ACT TCT CCT ATC TCT
SEQ ID NO: 84      5'-CGT CCT AAT CAC AGC AGC CCT ACT TCT CCT ATC TCT
SEQ ID NO: 85      5'-GT CCT AAT CAC AGC AGC CCT ACT TCT CCT ATC TCT
SEQ ID NO: 86      5'-T CCT AAT CAC AGC AGC CCT ACT TCT CCT ATC TCT
SEQ ID NO: 87      5'-CCT AAT CAC AGC AGC CCT ACT TCT CCT ATC TCT
SEQ ID NO: 88      5'-CT AAT CAC AGC AGC CCT ACT TCT CCT ATC TCT
SEQ ID NO: 89      5'-T AAT CAC AGC AGC CCT ACT TCT CCT ATC TCT
       5' extension, 3' extension, or both, keeping length constant:
SEQ ID NO: 90      5'-C CGT CCT AAT CAC AGC AGC CCT ACT TCT CC
SEQ ID NO: 91      5'-CGT CCT AAT CAC AGC AGC CCT ACT TCT CCT
SEQ ID NO: 92      5'-GT CCT AAT CAC AGC AGC CCT ACT TCT CCT A
SEQ ID NO: 93      5'-T CCT AAT CAC AGC AGC CCT ACT TCT CCT AT
SEQ ID NO: 94      5'-CCT AAT CAC AGC AGC CCT ACT TCT CCT ATC
SEQ ID NO: 95      5'-CT AAT CAC AGC AGC CCT ACT TCT CCT ATC T
SEQ ID NO: 96      5'-T AAT CAC AGC AGC CCT ACT TCT CCT ATC TC
SEQ ID NO: 97      5'-AAT CAC AGC AGC CCT ACT TCT CCT ATC TCT
Antigene to light chain mtDNA, wild-type sequence:
SEQ ID NO: 98      3'-TTA GTG TCG TCA GGA TGA AGA GG
Antigene to light chain mtDNA, mutant sequence:
SEQ ID NO: 99      3'-TTA GTG TCG TCC GGA TGA AGA GG
       5' truncation:
SEQ ID NO: 100     3'-TTA GTG TCG TCC GGA TGA AGA G
```

-continued

```
SEQ ID NO: 101    3'-TTA GTG TCG TCC GGA TGA AGA
SEQ ID NO: 102    3'-TTA GTG TCG TCC GGA TGA AG
SEQ ID NO: 103    3'-TTA GTG TCG TCC GGA TGA A
SEQ ID NO: 104    3'-TTA GTG TCG TCC GGA TGA
SEQ ID NO: 105    3'-TTA GTG TCG TCC GGA TG
SEQ ID NO: 106    3'-TTA GTG TCG TCC GGA T

3' truncation:

SEQ ID NO: 107    3'-TA GTG TCG TCC GGA TGA AGA GG
SEQ ID NO: 108    3'-A GTG TCG TCC GGA TGA AGA GG
SEQ ID NO: 109    3'-GTG TCG TCC GGA TGA AGA GG
SEQ ID NO: 110    3'-TG TCG TCC GGA TGA AGA GG
SEQ ID NO: 111    3'-G TCG TCC GGA TGA AGA GG
SEQ ID NO: 112    3'-TCG TCC GGA TGA AGA GG

3' and 5' truncation:

SEQ ID NO: 113    3'-TA GTG TCG TCC GGA TGA AGA G
SEQ ID NO: 114    3'-A GTG TCG TCC GGA TGA AGA
SEQ ID NO: 115    3'-GTG TCG TCC GGA TGA AG
SEQ ID NO: 116    3'-TG TCG TCC GGA TGA A

3' and 5' extension:

SEQ ID NO: 117    3'-G GCA GGA TTA GTG TCG TCC GGA TGA AGA GGA TAG AGA
SEQ ID NO: 118    3'-GCA GGA TTA GTG TCG TCC GGA TGA AGA GGA TAG AGA
SEQ ID NO: 119    3'-CA GGA TTA GTG TCG TCC GGA TGA AGA GGA TAG AGA
SEQ ID NO: 120    3'-A GGA TTA GTG TCG TCC GGA TGA AGA GGA TAG AGA
SEQ ID NO: 121    3'-GGA TTA GTG TCG TCC GGA TGA AGA GGA TAG AGA
SEQ ID NO: 122    3'-GA TTA GTG TCG TCC GGA TGA AGA GGA TAG AGA
SEQ ID NO: 123    3'-A TTA GTG TCG TCC GGA TGA AGA GGA TAG AGA

3' extension, 5' extension, or both, keeping length constant:

SEQ ID NO: 124    3'-G GCA GGA TTA GTG TCG TCC GGA TGA AGA GG
SEQ ID NO: 125    3'-GCA GGA TTA GTG TCG TCC GGA TGA AGA GGA
SEQ ID NO: 126    3'-CA GGA TTA GTG TCG TCC GGA TGA AGA GGA T
SEQ ID NO: 127    3'-A GGA TTA GTG TCG TCC GGA TGA AGA GGA TA
SEQ ID NO: 128    3'-GGA TTA GTG TCG TCC GGA TGA AGA GGA TAG
SEQ ID NO: 129    3'-GA TTA GTG TCG TCC GGA TGA AGA GGA TAG A
SEQ ID NO: 130    3'-A TTA GTG TCG TCC GGA TGA AGA GGA TAG AG
SEQ ID NO: 131    3'-TTA GTG TCG TCC GGA TGA AGA GGA TAG AGA
```

The composition of the antisense or triplex oligonucleotides can also influence the efficiency of inhibition. For example, it is preferable to use oligonucleotides that are resistant to degradation by the action of endogenous nucleases. Nuclease resistance will confer a longer in vivo half-life to the oligonucleotide thus increasing its efficacy and reducing the required dose. Greater efficacy may also be obtained by modifying the oligonucleotide so that it is more permeable to cell membranes. Such modifications are well known in the art and include the alteration of the negatively charged phosphate backbone bases, or modification of the sequences at the 5' or 3' terminus with agents such as intercalators and crosslinking molecules. Specific examples of such modifications include oligonucleotide analogs that contain methylphosphonate (Miller, P. S., *Biotechnology*, 2:358–362 (1991)), phosphorothioate (Stein, *Science* 261:1004–1011 (1993)) and phosphorodithioate linkages (Brill, W. K -D., *J. Am. Chem. Soc.*, 111:2322 (1989)). Other types of linkages and modifications exist as well, such as a polyamide backbone in peptide nucleic acids (Nielson et al., *Science* 254:1497 (1991)), formacetal (Matteucci, M., *Tetrahedron Lett.* 31:2385–2388 (1990)) carbamate and morpholine linkages as well as others known to those skilled in the art. In addition to the specificity afforded by the antisense agents, the target RNA or genes can be irreversibly modified by incorporating reactive functional groups in these molecules which covalently link the target sequences e.g. by alkylation.

Recombinant methods known in the art can also be used to achieve the antisense or triplex inhibition of a target nucleic acid. For example, vectors containing antisense nucleic acids can be employed to express protein or antisense message to reduce the expression of the target nucleic acid and therefore its activity. Such vectors are known or can be constructed by those skilled in the art and should contain all expression elements necessary to achieve the desired transcription of the antisense or triplex sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses, such as bacteriophages, baculoviruses and retroviruses, cosmids, plasmids, liposomes and other recombination vectors. The vectors can also contain elements for use in either procaryotic or eukaryotic host systems. One of ordinary skill in the art will know which host systems are compatible with a particular vector.

The vectors can be introduced into cells or tissues by any one of a variety of known methods within the art. Such methods are described for example in Sambrook et al., *Molecular Cloning: A Laboratory Manual,* Cold Spring Harbor Laboratory, New York (1992), which is hereby incorporated by reference, and in Ausubel et al., *Current Protocols in Molecular Biology,* John Wiley and Sons, Baltimore, Md. (1989), which is also hereby incorporated by reference. The methods include, for example, stable or transient transfection, lipofection, electroporation and infection with recombinant viral vectors. Introduction of nucleic acids by infection offers several advantages over the other listed methods which includes their use in both in vitro and in vivo settings. Higher efficiency can also be obtained due to their infectious nature. Moreover, viruses are very specialized and typically infect and propagate in specific cell types. Thus, their natural specificity can be used to target the antisense vectors to specific cell types in vivo or within a tissue or mixed culture of cells. Viral vectors can also be modified with specific receptors or ligands to alter target specificity through receptor mediated events.

A specific example of a viral vector for introducing and expressing antisense nucleic acids is the adenovirus derived vector Adenop53TX. This vector expresses a herpes virus thymidine kinase (TX) gene for either positive or negative selection and an expression cassette for desired recombinant sequences such as antisense sequences. This vector can be used to infect cells including most cancers of epithelial origin, glial cells and other cell types. This vector as well as others that exhibit similar desired functions can be used to treat a mixed population of cells to selectively express the antisense sequence of interest. A mixed population of cells can include, for example, in vitro or ex vivo culture of cells, a tissue or a human subject.

Additional features may be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefor a means by which infection can be controlled because it provides inducible suicide through the addition of antibiotics. Such protection ensures that if, for example, mutations arise that produce mutant forms of the viral vector or antisense sequence, cellular transformation will not occur. Moreover, features that limit expression to particular cell types can also be included. Such features include, for example, promoter and expression elements that are specific for the desired cell type.

The present invention also provides methods for the selective destruction of defective mitochondria. Since the mitochondrial genome is heteroplasmic (i.e. it contains mutated and normal DNA), this will leave intact mitochondria carrying normal or wild-type DNA and these normal mitochondria will repopulate the targeted tissue, normalizing mitochondrial function. This can be accomplished by identifying unique characteristics of mitochondria carrying mutated DNA, designing a small molecule that is directed at one or more of these unique characteristics, and conjugating a mitochondrial toxin to this small molecule. Thus, a "targeting molecule" is any molecule that selectively accumulates in mitochondria having defective cytochrome c oxidase activity, and includes acridine orange derivatives and JC-1 derivatives as discussed hereinbelow. "Mitochondrial toxins" are molecules that destroy or disable the selected mitochondria, and include phosphate, thiophosphate, dinitrophenol, maleimide and antisense oligonucleotides such as those discussed above. The toxin will be concentrated within the defective mitochondria by the targeting molecule and will disable or destroy selectively the defective mitochondria. The molecule may be an active mitochondrial toxin in its conjugated form. However, it is preferred to design the molecule such that it is inactive in its conjugated form. The chemical linkage between the targeting molecule and the toxin may be a substrate for a mitochondria-specific enzyme or sensitive to redox cleavage. Choice of the linkage depends upon the chemical nature of the targeting molecule and toxin and the requirements of the cleavage process. Once the conjugate is concentrated in the defective mitochondria, the toxin is cleaved from the targeting molecule, activating the toxin.

Mitochondria with defective cytochrome c oxidase activity exhibit impaired electron transport, leading to decreased synthesis of adenosine triphosphate and general bioenergetic failure. As a consequence, mitochondria carrying mutated DNA will become enlarged and the intramitochondrial membrane potential increases.

Enlarged mitochondria have increased levels of cardiolipin and other negatively charged phospholipids. The acridine orange derivative 10N-nonylacridine orange (NAO) binds relatively specifically to cardiolipin and accumulates in dysfunctional mitochondria. The accumulation of NAO and other chemical derivatives of acridine orange, including but not limited to those with aliphatic chains of variable length attached to the ring nitrogen of acridine orange ([3,6-bis (dimethyl-amino) acridine]), such as 10N-pentylacridine orange, 10N-octylacridine orange, and dodecylacridine orange, is independent of the mitochondrial transmembrane potential. Maftah et al., *Biochemical and Biophysical Research Communications* 164 (1):185–190 (1989)). At concentrations up to 1 $\mu$M, NAO and its derivatives can be used to target other molecules to the inner mitochondrial matrix. If the NAO is chemically linked to a mitochondrial toxin such as phosphate, thiophosphate, dinitrophenol, maleimide and antisense oligonucleotides, then mitochondria accumulating the NAO-mitochondrial toxin conjugate can be selectively disabled or destroyed. Alternately, at high concentrations (3–10 $\mu$M) NAO and its derivatives inhibit electron transport, ATP hydrolysis and $P_i$-transport and disrupt respiration (Maftah et al., *FEBS Letters* 260(2):236–240 (1990). At these concentrations, NAO is mitochondrial toxin.

According to an embodiment of the present invention, the terminus of any aliphatic or other type of chain (such as polyethylene glycol) attached to the ring nitrogen of acridine orange is chemically derivatized with carboxylic acid, hydroxyl, sulfhydryl, amino or similar groups to accept any mitochondrial toxin. In other embodiments, additional sites of attachment of the mitochondrial toxin to acridine orange and acridine orange derivatives are selected. For example, the 10-N-(10-hydroxy-1-decyl)-3,6-bis(dimethylamino) acridine bromide salt may be prepared and further derivatized to 10-N-(10-phosphoryl-1-decyl)-3,6-bis (dimethylamino) acridine chloride salt or 10-N-(10-thiophosphoryl-i-decyl)-3,6-bis(dimethylamino)acridine chloride salt. Alternately, 10-N-(11-undecanoic acid)-3,6-bis (dimethylamino)acridine bromide salt may be prepared and further derivatized to 10-N-(11-undecan-1-oic acid 2,4-dinitrophenyl ester)-3,6-bis(dimethylamino) acridine bromide salt. Upon cleavage, the phosphate, thiphospate or dinitrophenol levels selectively increase within defective mitochondria and destroy them. The functionalization and covalent attachment of the toxin does not need to depend on subsequent release of the toxin by cleavage of the NAO from the toxin, if the attachment point on the toxin is non-interfering with the function of the toxin within the mitochondria.

Several examples of the preparation of acridine orange derivatives are summarized in FIG. 4 and in Examples IX(a)–IX(f) hereinbelow. Other modifications are permitted as known to those skilled in the art.

Still other embodiments of the present invention target changes in the intramitochondrial membrane potential due to defective cytochrome c oxidase activity. Delocalized lipophilic cations have been used to monitor mitochondrial membrane potential. The uptake of these cations is related to the presence of the negative sink inside the mitochondria created by the proton pump. As mitochondria increase in size due to cytochrome c oxidase defects, the transmembrane potential will increase and these defective mitochondria will accumulate lipophilic cations. According to an embodiment of the present invention, these lipophilic cations are conjugated to mitochondrial toxins and used to destroy defective mitochondria that possess increased transmembrane potentials. Rhodamine-123 the hydrated form of which is as follows Rhodamine 123 hydrate has been used extensively to monitor mitochondrial membrane potential and can conjugate to mitochondrial toxins to concentrate toxins within the mitochondria. The compound 5,5',6, 6'-tetrachloro-1,1',3,3'-tetraethylbenzimidiazolo-carbocyanine iodide (JC-1) also a ccumulates in mitochondria dependent upon the transmembrane potential. When JC-1 exceeds a critical concentration, 'J-aggregates form in the mitochondrial matrix, and their size causes these JC-1 J-aggregates to diffuse slowly out of the mitochondria (Reers et al., *Biochemistry*, 30(18):4480–4486 (1991)). JC-1 may be chemically conjugated to a mitochondrial toxin, producing a long-lived toxic compound to mitochondria displaying increased transmembrane potential relative to normal mitochondria.

As with NAO, by adding a functional group to the JC-1 structure one can covalently attach another chemical entity to the JC-1 subunit. Delivery to the cells then causes the dual agent to be preferentially transported into the mitochondria, where the dual agent may be cleaved at the covalent attachment to release a toxin within the mitochondria where it exerts the desired effect. Alternatively, the functionalization and covalent attachment of the toxin does not need to depend on subsequent release of the toxin by cleavage of the JC-1 from the active agent, if the attachment point on the active species is non-interfering with the function of the toxin within the mitochondria.

Figure 5:
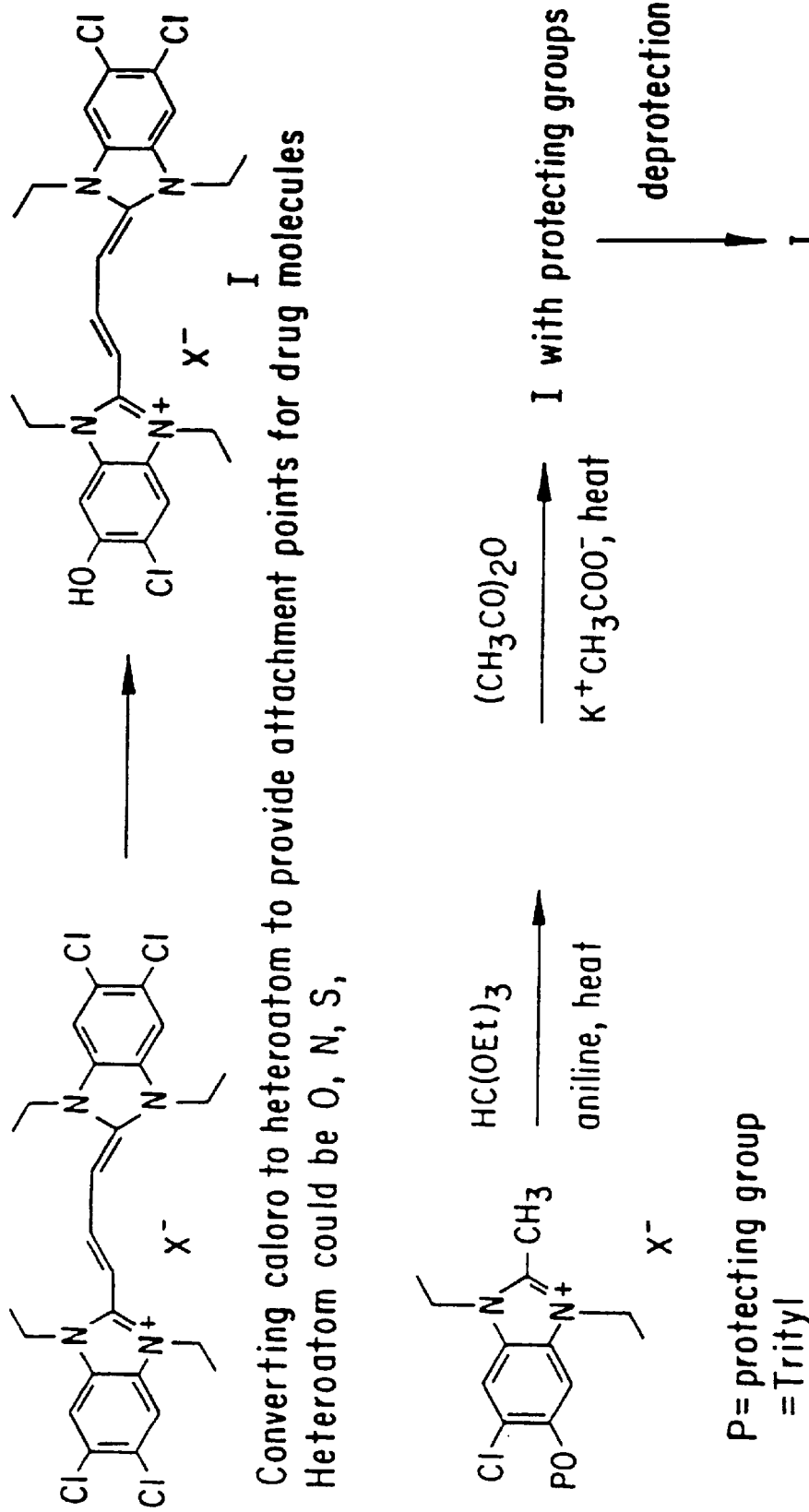
Figure 6:
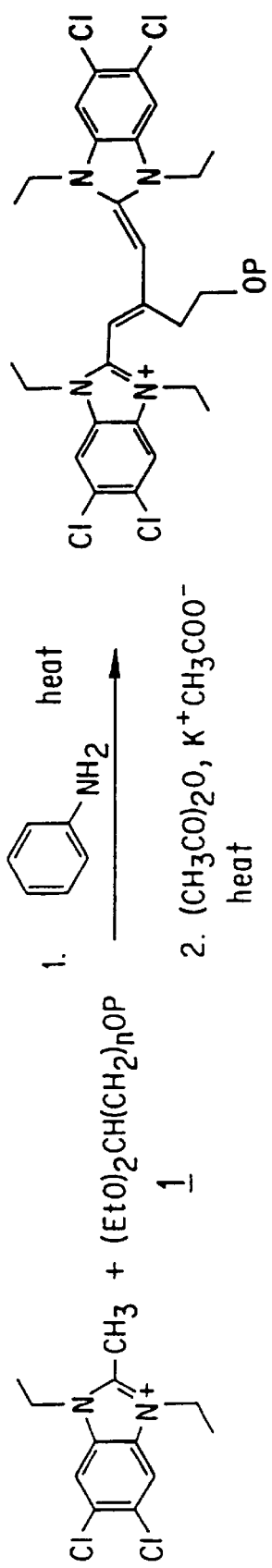

FIGS. 5, 6 and 7 outline the functionalization of JC-1 by several different methods. Examples IX(g)–IX(f) hereinbelow illustrate an oxygen functionality, but the same can be accomplished with a nitrogen, sulfur or carboxylic acid functionality.

By utilizing the quasi-symmetrical nature of JC-1, a new chemical entity may be synthesized that is "half" JC-1 and contains a functional group capable of being used as a point for covalent attachment of another chemical entity to the JC-1 subunit. The existence of the JC-1 subunit facilitates selective transport of the whole molecule to the mitochondria where, if desired, enzymes effect cleavage of the JC-1 subunit from the toxin, allowing it to exert the desired effect. Alternatively, the functionalization and covalent attachment of the toxin does not need to depend on subsequent release of the toxin by cleavage of the JC-1 subunit from the toxin, if the attachment point on the toxin is non-interfering with the function of the active agent within the mitochondria.

Figure 8:
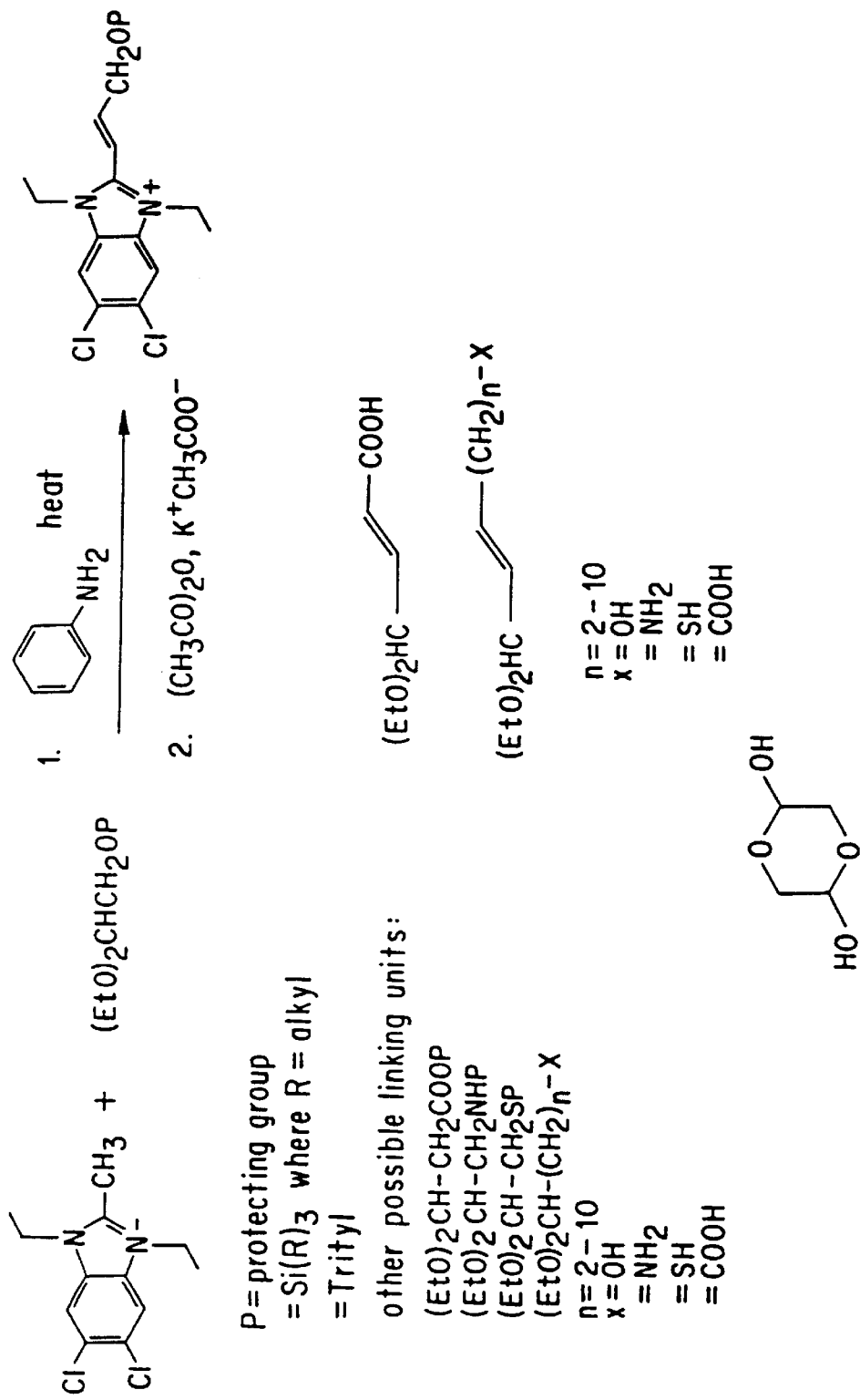

FIG. 8 outlines the synthesis of a functionalized "half" JC-1 subunit by several different methods. The attachment of the active chemical species is via the heteroatom incorporated in the JC-1 or "half" JC-1 structure. This attachment may be accomplished by any number of linking strategies such as by taking advantage of a functionality on the active molecule (such as a carboxylic acid to form an ester with the oxygen of the altered JC-1) or by using a linker to space between the JC-1 and the toxin. These strategies are well known to those skilled in the chemistry of preparing diagnostic or labelling molecules with reporter functions for biological studies and include ester, amide, urethane, urea, sulfonamide, and sulfonate ester (SET. Smiley et al., *Proc. Nat'l, Acad. Sci. USA*, 88:3671–3675 (1991)).

As noted hereinabove, mitochondria carrying mutated cytochrome c oxidase genes have increased levels of cardiolipin and other negatively charged phospholipids as well as increased mitochondrial membrane potential. As a result, the mitochondria selectively accumulate targeting molecules, including acridine orange derivatives and lipophilic cations such as rhodamine-123 and JC-1 derivatives. In addition to selectively introducing toxins into the mitochondria, such targeting molecules can also selectively introduce imaging ligands, which can form the basis of effective in vivo and in vitro diagnostic strategies. Such strategies include magnetic resonance imaging (MRI), single photon emission computed topography (SPECT), and positron emission tomography (PET). Preferred imaging ligands for the practice of the present invention include radioisotopes (such as $^{123}I$, $^{125}I$, $^{18}F$, $^{13}N$, $^{15}O$, $^{11}C$, $^{99m}Tc$, $^{67}Ga$ and so forth), haptens (such as digoxigenin), biotin, enzymes (such as alkaline phosphatase or horseradish peroxidase), fluorophores (such as fluorescein lanthanide chelates, or Texas Red®), and gadolinium chelates for MRI applications. Saha et al., *Seminars in Nuclear Medicine*, 4:324–349 (1994).

As an example of an in vitro diagnosis, a targeting molecule, such as an acridine orange or JC-1 derivative, is labelled with fluorescein as an imaging ligand. The labelled targeting molecule is introduced into a human tissue cell culture such as a primary fibroblast culture. After a period of several hours, cells having mitochondria with defective cytochrome c oxidase genes selectively absorb the labelled targeting molecule in amounts greater than cells without such mitochondria. The cells are then washed and sorted in a fluorescence activated cell sorter (FACS) such as that sold by Becton Dickinson. Threshold limits can be established for the FACS using cells with wild-type mitochondria. Similarly, in an in vivo diagnosis, a targeting molecule such as an acridine orange or JC-1 derivative is labelled with $^{99m}Tc$, $^{18}F$ or $^{123}I$ as an imaging ligand. This labelled targeting molecule is introduced into the bloodstream of a patient. After a period of several hours, the labelled targeting molecule accumulates in those tissues having mitochondria with cytochrome-oxidase-defective genes. Such tissues can be directly imaged using positron-sensitive imaging equipment.

Selective destruction of defective mitochondria is also achieved by using ribozymes. Ribozymes are a class of RNA molecules that catalyze strand scission of RNA molecules independent of cellular proteins. Specifically, ribozymes may be directed to hybridize and cleave target mitochondrial mRNA molecules. The cleaved target RNA cannot be translated, thereby preventing synthesis of essential proteins which are critical for mitochondrial function. The therapeutic application thus involves designing a ribozyme which incorporates the catalytic center nucleotides necessary for function and targeting it to mRNA molecules which encode for dysfunctional COX subunits. The ribozymes may be chemically synthesized and delivered to cells or they can be expressed from an expression vector following either permanent or transient transfection. Therapy is thus provided by the selective removal of mutant mRNAs in defective mitochondria.

The foregoing and following description of the invention and the various embodiments is not intended to be limiting of the invention but rather is illustrative thereof. Those skilled in the art of molecular genetics can formulate further embodiments encompassed within the scope of the present invention

EXAMPLES

Definitions of Abbreviations:

1× SSC=150 mM sodium chloride, 15 mM sodium citrate, pH 6.5–8

SDS=sodium dodecyl sulfate

BSA=bovine serum albumin, fraction IV probe=a labelled nucleic acid, generally a single-stranded oligonucleotide, which is complementary to the DNA target immobilized on the membrane. The probe may be labelled with radioisotopes (such as $^{32}P$), haptens (such as digoxigenin), biotin, enzymes (such as alkaline phosphatase or horseradish peroxidase), fluorophores (such as fluorescein or Texas Red), or chemilumiphores (such as acridine), PCR=polymerase chain reaction, as described by Erlich et al., *Nature* 331:461–462 (1988) hereby incorporated by reference.

Example I

Isolation and Cloning of Cytochrome c Oxidase Genes

DNA is obtained from AD patients and from non-Alzheimer's (normal) individuals. Age-matched normal individuals and AD patients classified as probable AD by NINCDS criteria (McKann et al., *Neurology* 34:939–944 (1984)) are used.

For blood samples, 6 ml samples are drawn, added to 18 ml of dextrane solution (3% dextrane, average MW=250,000 kiloDaltons (kDa), 0.9% sodium chloride, 1 mM ethylenedinitrilo tetraacetate, mixed and maintained at room temperature for 40 minutes without agitation to allow erythrocytes to sediment.

The plasma and leukocyte fraction is transferred to a centrifuge tube and leukocytes are collected by centrifugation at 14,000× g for 5 minutes. The leukocyte pellet is resuspended in 3.8 ml of water and vortexed for 10 seconds to lyse remaining erythrocytes. 1.2 ml of 0.6 M sodium chloride is added and the sample is again centrifuged at 14,000× g for 5 minutes to collect the leukocytes. The leukocyte pellet is resuspended in 0.4 ml of a solution containing 0.9% sodium chloride/1 mM ethylenedinitrilo tetraacetate and stored at −80° C.

Total cellular DNA is isolated from 0.2 ml of the frozen leukocyte sample. The frozen leukocytes are thawed, then collected by centrifugation at 14,000× g in a microcentrifuge for 5 minutes. The cell pellet is washed three times with 0.8 ml of Dulbecco's Phosphate Buffered Saline (PBS; Gibco Laboratories, Life Technologies, Inc., Grand Island, N.Y.; catalog # 310-4040AJ) and resuspended in 0.3 ml water. The leukocytes are lysed by adding 0.06 ml of 10% sodium dodecyl sulfate to the cell suspension, then incubating the samples for 10 minutes in a boiling water bath. After the samples come to room temperature, cellular debris is pelleted by centrifugation at 14,000× g for 5 minutes. The supernatant is transferred to a clean microcentrifuge tube and extracted twice with 0.5 ml of phenol:chloroform (1:1) and twice with chloroform. DNA is precipitated by addition of 0.03 ml of 5M sodium chloride and 0.7 ml of 100% ethanol to the sample. Following incubation at −80° C., the precipitated DNA is collected by centrifugation at 14,000× g for 15 minutes. The DNA pellet is washed with 0.8 ml of 80% ethanol, briefly dried, then resuspended in 0.2–0.4 ml of TE buffer (10 mM Tris-HCl, pH 7.5, 1 mM EDTA), The DNA concentration is determined by UVT absorption at 260 nm.

As an alternative method for isolation of DNA from blood, 5 ml blood samples are drawn and added to Accuspin™ Tubes (12 ml or 50 ml capacity, Sigma Diagnostics, St. Louis, Mo.), prepared according to the manufacturer's instructions and containing Histopaque™ separation medium. The tubes are centrifuged at 1,000× g for 10 minutes. The plasma and leukocyte fraction is transferred to a centrifuge tube containing 1 ml of TE buffer, and leukocytes are collected by centrifugation at 2,500 rpm for 10 minutes. The leukocyte pellet is resuspended in 5 ml TE buffer and 0.2 ml of 200 SDS and 0.1 ml of Proteinase K at 20 mg/ml are added. After incubation at 37° C. for four hours while shaking the lysate is extracted twice with phenol and twice with chloroform:isoamyl alcohol (24:1). DNA is precipitated by addition of ⅒ volume 3.0 M sodium acetate (pH 5.0) and 2 volumes of ethanol. Following incubation at −20° C. overnight, the precipitated DNA is collected by centrifugation, washed with 70% ethanol, briefly dried, and resuspended in 0.1–0.2 ml of TE buffer. The DNA concentration is determined by UV absorption at 260 nm.

For brain samples, total cellular DNA is isolated from 0.1–0.2 grams of frozen brain tissue. The frozen brain tissue is placed into a glass dounce homogenizer (Pyrex, VWR catalog #7726-S) containing 3 ml of lysis buffer (50 mM Tris-HCl, pH 7.9, 100 mM EDTA, 0.1 M NaCl, 0.03 M dithiothreitol, 1% sodium dodecyl sulfate, 1 mg/ml proteinase K) and homogenized with a few strokes of the glass rod. The brain homogenate is transferred to an incubation tube and placed at 45–50° C. for 30–60 minutes. After the addition of 5 ml of sterile water, the homogenate is extracted with phenol/chloroform two to three times, then twice with chloroform. DNA is precipitated by mixing the extracted sample with ½₀× volume of 5 M NaCl and 2.5× volumes of 200 proof ethanol and placed at −20° C. DNA is pelleted by centrifugation at 6,000× g for 15 minutes. The DNA pellet is washed with 10 ml of 80% ethanol, briefly dried, and resuspended in 200–400 µl of TE buffer. The DNA concentration is determined by UV absorption at 260 nm.

The target cytochrome c oxidase gene sequences are amplified by Polymerase Chain Reaction (PCR) (Erlich et al., *Nature* 331:461–462 (1988)). Primers are designed using the published Cambridge sequences for normal human COX genes. Primers are specific for COX gene sequences located approximately 100 nucleotides upstream and downstream of the mitochondrial COX genes encoding subunits I, II, and III. Primers have the following sequences: COX I-forward primer (5'-CAATATGAAAATCACCTCGGAGC-3') (SEQ. ID. NO. 132), COX I-reverse primer (5'-TTAGCCTATAATTTAACTTTGAC-3') (SEQ. ID. NO. 133), COX II-forward primer (5'-CAAGCCAACCCCATGGCCTCC-3') (SEQ. ID. NO. 134), COX II-reverse primer (5'-AGTATTTAGTTGGGGCATTTCAC-3') (SEQ. ID. NO. 135), COX III-forward primer (5'-ACAATTCTAATTCTACTGACTATCC-3') (SEQ. ID. NO. 136), COX III-reverse primer (5'-TTAGTAGTAAGGCTAGGAGGGTG-3') (SEQ. ID. NO. 137).

Primers are chemically synthesized using a Cyclone Plus DNA Synthesizer (Millipore Corporation, Marlborough, Mass.) or a Gene assembler DNA Synthesizer (Pharmacia) utilizing beta-cyanoethylphosphoramidite chemistry. Newly synthesized primers are deprotected using ammonium hydroxide, lyophilized and purified by NAP-10 column chromatography (Pharmacia LKB Biotechnology Inc., Piscataway, N.J.; catalog # 17-0854-01). DNA concentration is determined by UV absorption at 260 nm.

Alternatively, primers are chemically synthesized using an ABl 394 DNA/RNA Synthesizer (Applied Biosystems, Inc., Foster City, Calif.) using standard beta-cyanoethylphosphoramidite chemistry. Without cleavage of the trityl group, the primers are deprotected with ammonium hydroxide and purified using Oligonucleotide Purification Cartridges (Applied Biosystems, Inc., Foster City, Calif.). The DNA concentration is determined by UV absorption at 260 nm.

Amplifcation is performed using 0.5–1.0 µg DNA in a reaction volume of 50–100 µl containing 10 mM Tris-HCl pH 8.3–9.5, 50 mM potassium chloride, 1–4 mM magnesium chloride, 200 µM each of DATP, dCTP, dGTP, and dTTP ("amplification cocktail"), 200 ng each of the appropriate COX forward and reverse primers and 5 units of AmpliTaq Polymerase (Perkin-Elmer Corporation; catalog # N801-0060).

Amplification using the GeneAmp PCR System 9600 (Perkin Elmer Corporation) is allowed to proceed for one cycle at 95° C. for 10 seconds, 25 cycles at 95° C. for 1 minute, 60° C. for 1 minute, 72° C. for 1 minute, one cycle at 72° C. for 4 minutes, after which the samples are cooled to 4° C. Five separate amplification reactions are performed for each patient and each cytochrome c oxidase subunit. After the reactions are complete, the samples for each patient and subunit are combined and the amplified product is precipitated at −80° C. by the addition ⅒ volume of 5 M sodium chloride and 2 volumes of 100% ethanol.

The PCR amplification product is pelleted by centrifugation, dried briefly, resuspended in 40 µl of TE buffer and purified by agarose gel electrophoresis (Sambrook et al., "Molecular Cloning: A Laboratory Manual," Cold Spring Harbor Laboratory, 1988). DNA is stained with ethidium bromide and visualized under long wavelength UV light. Bands of the expected lengths (approximately 1,700 bp for COX I, 900 bp for COX II and 1,000 bp for COX III) are excised from the gel. The gel containing the DNA is minced into small pieces and placed into a microcentrifuge tube. 0.3 ml of 1 M sodium chloride is added to the gel fragments and the sample is frozen at −80° C., then thawed and incubated at 50° C. for 15–20 minutes. Agarose is sedimented by centrifugation at 14,000× g for 5 minutes, the supernatant containing the DNA is transferred to a new vial and the DNA fragments are collected by ethanol precipitation.

The amplified DNA fragments are cloned into the plasmid pCRII (Invitrogen Corp., San Diego, Calif.) using the TA-Cloning Kit (Invitrogen Corps, San Diego, Calif.; catalog # K2000-01). Ligations are performed in a reaction volume of 11 µl containing 1–5 µl of PCR amplification product, 2 µl of plasmid (50 ng), 1 µl of 10× ligation buffer and 1 µl of T4 DNA Ligase (4 units). Ligation reactions are incubated at 10–12° C. for 15–16 hours.

Vector-ligated PCR fragments are transformed into competent *E. coli* cells of the strains XL1-Blue MRF', XL2-Blue MRF' and SURE (Stratagene, San Diego, Calif.). Transformed cells are spread onto LB-agar plates containing ampicillin (50 µg/ml), kanamycin (50 µg/ml), IPTG (isopropyl-3-D-thiogalactopyranoside, 20 µg/ml) and X-Gal (100 µg/ml). The blue/white color selection mechanism provided by the cloning vector in combination with the *E. coli* cells allows for easy detection of recombinant clones, which are white.

Multiple white colonies are selected for each patient and COX subunit and screened by PCR for the presence of a correct insert using nested primers derived from the published Cambridge sequences. The primers are specific for sequences located approximately 40–60 nucleotides upstream and downstream of COX genes encoding subunits I, II and III. The sequences of the primers are as follows: COX I-forward primer (5'-AGGCCTAACCCCTGTC-3') (SEQ. ID. NO. 138), COX I-reverse primer (5'-GGCCATGGGGTTGGC-3') (SEQ. ID. NO. 139), COX II-forward primer (5'-AGGTATTAGAAAAACCA-3') (SEQ. ID. NO. 140), COX II-reverse primer (5'ATCTTTAACTTAAAAGG) (SEQ. IDe NO. 141), COX III-forward primer (5'-GCCTTAATCCAAGCC-3') (SEQ. ID. NO. 142), COX IIIreverse primer (5'-GAATGTTGTCAAAACTAG-3') (SEQ. ID. NO. 143).

DNA samples from lysed cell supernatants are used as templates for PCR amplification. Individual colonies are selected and incubated overnight at 37° C. with shaking (225 rpm) in LB-broth containing ampicillin and kanamycin. 100–200 μl of each culture is centrifuged at 14,000× g for 2 minutes. The cell pellet is resuspended in 5–10 μl of water, then lysed by incubation in a boiling water bath for 5 minutes. Cellular debris is removed by centrifugation at 14,000× g for 2 minutes.

Amplification of the cloned DNA samples is performed in a reaction volume of 10 μl containing amplification cocktail, 40 ng each of the appropriate COX-S forward and reverse primers and 0.25 units of AmpliTaq Polymerase. Amplification is performed for one cycle at 95° C. for 10 seconds, 25 cycles at 95° C. for 1 minute, 44° C. for 1 minute, 72° C. for 1 minute, and cooled to 4° C., using the GeneAmP PCR System 9600. PCR products are analyzed by horizontal agarose gel electrophoresis.

Example II

Sequencing of Cytochrome c Oxidase (COX) Genes

Plasmid DNA containing the COX gene inserts is obtained as described in Example I is isolated using the Plasmid Quik™ Plasmid Purification Kit (Stratagene, San Diego, Calif.) or the Plasmid Kit (Qiagen, Chatsworth, Calif., Catalog # 12145). Plasmid DNA is purified from 50 ml bacterial cultures. For the Stratagene protocol "Procedure for Midi Columns," steps 10–12 of the kit protocol are replaced with a precipitation step using 2 volumes of 100% ethanol at −20° C., centrifugation at 6,000× g for 15 minutes, a wash step using 80% ethanol and resuspension of the DNA sample in 100 μl TE buffer. DNA concentration is determined by horizontal agarose gel electrophoresis, or by UV absorption at 260 nm.

Sequencing reactions using double-stranded plasmid DNA are performed using the Sequenase Kit (United States Biochemical Corps, Cleveland, Ohio; catalog # 70770), the BaseStation T7 Kit (Millipore Corp.; catalog # MBBLSEQ01); the Vent Sequencing Kit (Millipore Corp; catalog # MBBLVEN01), the AmpliTaq Cycle Sequencing Kit (Perkin Elmer Corp.; catalog # N808-0110) and the Taq DNA Sequencing Kit (Boehringer Mannheim). The DNA sequences are detected by fluorescence using the BaseStation Automated DNA Sequencer (Millipore Corp.). For gene walking experiments, fluorescent oligonucleotide primers are synthesized on the Cyclone Plus DNA Synthesizer (Millipore Corp.) or the GeneAssembler DNA Synthesizer (Pharmacia LKB Biotechnology, Inc.) utilizing beta-cyanoethylphosphoramidite chemistry. The following primer sequences are prepared from the published Cambridge sequences of the COX genes for subunits I, II, and III, with fluorescein (F; FluoreDite fluorescein amidite, Millipore Corps. or FluorePrime fluorescein amidite, Pharmacia LKB Biotechnology, Inc.) being introduced in the last step of automated DNA synthesis: COX I primer1 (5'-AGGCCTAACCCCTGTC-3') (SEQ. ID. NO. 144); COX I primer2 (5'-GTCACAGCCCATG-3') (SEQ. ID. NO. 145); COX I primer3 (5'-CCTGGAGCCTCCGTAG-3') (SEQ. ID. NO. 146); COX I primer4 (5'-CTTCTTCGACCCCG-3') (SEQ. ID. NO. 147); COX I primer5 (5'-CATATTTCACCTCCG-3') (SEQ. ID. NO. 148); COX I primer6 (5'-CCTATCAATAGGAGC-3') (SEQ. ID. NO. 149); COX I primer7 (540 -CATCCTATCATCTGTAGG-3') (SEQ. ID. NO. 150); COX II primer1 (5'-AGGTATTAGAAAAACCA-3') (SEQ. ID. NO. 151); COX II primer2 (5'-TAACTAATACTAACATCT-3') (SEQ. ID. NO. 152); COX II primer3 (5'-TGCGACTCCTTGAC-3') (SEQ. ID. NO. 153); COX III primer1 (5'-GCCTTAATCCAAGCC-3') (SEQ. ID. NO. 154); COX III primer2 (5'-CAATGATGGCGCGATG-3') (SEQ. ID. NO. 155); COX III primer3 (5'-CCGTATTACTCGCATCAGG-3') (SEQ. ID. NO. 156); COX III primer4 (5'-CCGACGGCATCTACGGC-3') (SEQ. ID. NO. 157). Primers are deprotected and purified as described above. DNA concentration is determined by UV absorption at 260 nm.

Sequencing reactions are performed according to manufacturer's instructions except for the following modification: 1) the reactions are terminated and reduced in volume by heating the samples without capping to 94° C. for 5 minutes, after which 4 μl of stop dye (3 mg/ml dextran blue, 95%–99% formamide; as formulated by Millipore Corp.) are added; 2) the temperature cycles performed for the AmpliTaq Cycle Sequencing Kit reactions, the Vent Sequencing kit reactions, and the Taq Sequence Kit consist of one cycle at 95° C. for 10 seconds, 30 cycles at 95° C. for 20 seconds, at 44° C. for seconds and at 72° C. for 20 seconds followed by a reduction in volume by heating without capping to 94° C. for 5 minutes before adding 4 μl of stop dye.

Electrophoresis and gel analysis are performed using the BioImage and BaseStation Software provided by the manufacturer for the BaseStation Automated DNA Sequencer (Millipore Corp.). Sequencing gels are prepared according to the manufacturer's specifications. An average of ten different clones from each individual is sequenced. The resulting COX sequences are aligned and compared with published Cambridge sequences. Mutations in the derived sequence are noted and confirmed by resequencing the variant region.

As an alternative procedure for sequencing the COX genes, plasmid DNA containing the COX gene inserts obtained as described in Example I is isolated using the Plasmid Quik™ Plasmid Purification Kit with Midi Columns (Qiagen, Chatsworth, Calif.) Plasmid DNA is purified from 35 ml bacterial cultures. The isolated DNA is resuspended in 100 μl TE buffer. DNA concentrations are determined by OD(260) absorption.

As an alternative method, sequencing reactions using double stranded plasmid DNA are performed using the Prism™ Ready Reaction DyeDeoxy™ Terminator Cycle Sequencing Kit (Applied Biosystems, Inc., Foster City, Calif.), The DNA sequences are detected by fluorescence using the ABI 373A Automated DNA Sequencer (Applied Biosystems, Inc., Foster City, Calif.). For gene walking experiments, oligonucleotide primers are synthesized on the ABI 394 DNA/RNA Synthesizer (Applied Biosystems, Inc., Foster City, Calif.) using standard beta-cyanoethylphosphoramidite chemistry. The following primer sequences are prepared from the published Cambridge sequences of the COX genes for subunits I, II, and III:

```
COX1    primer11      (5'-TGCTTCACTCAGCC-3')              (SEQ. ID. NO. 158);
COX1    primer1SF     (5'-AGGCCTAACCCCTGTA-3')            (SEQ. ID. NO. 159);
COX1    primer11X     (5'-AGTCCAATGCTTCACTCA-3')          (SEQ. ID. NO. 160);
COX1    primer12      (5'-GCTATAGTGGAGGC-3')              (SEQ. ID. NO. 161);
COX1    primer12A     (5'-CTCCTACTCCTGCTCGCA-3')          (SEQ. ID. NO. 162);
COX1    primer12X     (5'-TCCTGCTCGCATCTGCTA-3')          (SEQ. ID. NO. 163);
COX1    primer12XX    (5'-CTCCTACTCCTGCTCGCA-3')          (SEQ. ID. NO. 164);
COX1    primer13      (5'-CCTACCAGGATTCG-3')              (SEQ. ID. NO. 165);
COX1    primer13A     (5'-CCTACCAGGCTTCGGAA-3')           (SEQ. ID. NO. 166);
COX1    primer13X     (5'-TCCTACCAGGCTTCGGAA-3')          (SEQ. ID. NO. 167);
COX1    primer14      (5'-CCTATCAATAGGAGC-3')             (SEQ. ID. NO. 168);
COX1    primer14XX    (5'-GTCCTATCAATAGGAGCTGTA-3')       (SEQ. ID. NO. 169);
COX1    primer1lC     (5'-GTAGAGTGTGCAACC-3')             (SEQ. ID. NO. 170);
COX1    primer1lCN    (5'-GTCTACGGAGGCTCC-3')             (SEQ. ID. NO. 171);
COX1    primer1lCX    (5'-AGGTCTACGGAGGCTCCA-3')          (SEQ. ID. NO. 172);
COX1    primer1lCXX   (5'-AGGAGACACCTGCTAGGTGTA-3')       (SEQ. ID. NO. 173);
COX1    primer12C     (5'-CCATACCTATGTATCC-3')            (SEQ. ID. NO. 174);
COX1    primer12CA    (5'-TCACACGATAAACCCTAGGAA-3')       (SEQ. ID. NO. 175);
COX1    primer12CX    (5'-GACCATACCTATGTATCCAA-3')        (SEQ. ID. NO. 176);
COX1    primer13C     (5'-CCTCCTATGATGGC-3')              (SEQ. ID. NO. 177);
COX1    primer13CN    (5'-GTGTAGCCTGAGAATAGG-3')          (SEQ. ID. NO. 178);
COX1    primer13CXX   (5'-GTCTAGGGTGTAGCCTGAGAA-3')       (SEQ. ID. NO. 179);
COX1    primer14C     (5'-GGGTTCGATTCCTTCC-3')            (SEQ. ID. NO. 180);
COX1    primer14CN    (5'-TGGATTGAAACCAGC-3')             (SEQ. ID. NO. 181);
COX1    primer14CX    (5'-GTTGGCTTGAAACCAGCTT-3')         (SEQ. ID. NO. 182);
COX2    primer21      (5'-TCATAACTTTGTCGTC-3')            (SEQ. ID. NO. 183);
COX2    primer21N     (5'-CATTTCATAACTTTGTCGTC-3')        (SEQ. ID. NO. 184);
COX2    primer21NA    (5'-AGGTATTAGAAAAACCA-3')           (SEQ. ID. NO. 185);
COX2    primer21NB    (5'-AAGGTATTAGAAAAACC-3')           (SEQ. ID. NO. 186);
COX2    primer21X     (5'-TTCATAACTTTGTCGTCAA-3')         (SEQ. ID. NO. 187);
COX2    primer2FSF    (5'-AAGGTATTAGAAAAACC-3')           (SEQ. ID. NO. 188);
COX2    primer2SFA    (5'-CCATGGCCTCCATGACTT-3')          (SEQ. ID. NO. 189);
COX2    primer22      (5'-TGGTACTGAACCTACG-3')            (SEQ. ID. NO. 190);
COX2    primer22A     (5'-ACAGACGAGGTCAACGAT-3')          (SEQ. ID. NO. 191);
COX2    primer22X     (5'-CATAACAGACGAGGTCAA-3')          (SEQ. ID. NO. 192);
COX2    primer21C     (5'-AGTTGAAGATTAGTCC-3')            (SEQ. ID. NO. 193);
COX2    primer21CN    (5'-TAGGAGTTGAAGATTAGTCC-3')        (SEQ. ID. NO. 194);
COX2    primer21CX    (5'-TGAAGATAAGTCCGCCGTA-3')         (SEQ. ID. NO. 195);
COX2    primer22C     (5'-GTTAATGCTAAGTTAGC-3')           (SEQ. ID. NO. 196);
COX2    primer22CXX   (5'-AAGGTTAATGCTAAGTTAGCTT-3')      (SEQ. ID. NO. 197);
```

```
                        -continued
COX3    primer31    (5'-AAGCCTCTACCTGC-3')          (SEQ. ID. NO. 198);

COX3    primer31N   (5'-CTTAATCCAAGCCTACG-3')       (SEQ. ID. NO. 199);

COX3    primer32    (5'-AACAGGCATCACCC-3')          (SEQ. ID. NO. 200);

COX3    primer32A   (5'-CATCCGTATTACTCGCATCA-3')    (SEQ. ID. NO. 201);

COX3    primer31C   (5'-GATGCGAGTAATACG-3')         (SEQ. ID. NO. 202);

COX3    primer31CX  (5'-GATGCGAGTAATACGGAT-3')      (SEQ. ID. NO. 203);

COX3    primer32C   (5'-AATTGGAAGTTAACGG-3')        (SEQ. ID. NO. 204);

COX3    primer32CX  (5'-AATTGGAAGTTAACGGTA-3')      (SEQ. ID. NO. 205);

COX3    primer32CXX (5'-GTCAAAACTAGTTAATTGGAA-3')   (SEQ. ID. NO. 206);
```

Sequencing reactions are performed according to the manufacturer's instructions. Electrophoresis and sequence analysis are performed using the ABI 373A Data Collection and Analysis Software and the Sequence Navigator Software (ABI, Foster City, Calif.). Sequencing gels are prepared according to the manufacturer's specifications. An average of ten different clones from each individual is sequenced. The resulting COX sequences are aligned and compared with the published Cambridge sequence. Mutations in the derived sequence are noted and confirmed by sequence of the complementary DNA strand.

Mutations in each COX gene for each individual are compiled. Comparisons of mutations between normal and AD patients are made and summarized in Tables I and II.

Example III

Detection of COX Mutations by Hybridization without Prior Amplification

This example illustrates taking test sample blood, blotting the DNA, and detecting by oligonucleotide hybridization in a dot blot format. This example uses two probes to determine the presence of the abnormal mutation at codon 74 of the COX II gene (see Table 1) in mitochondrial DNA of Alzheimer's patients. This example utilizes a dot-blot format for hybridization, however, other known hybridization formats, such as Southern blots, slot blots, "reverse" dot blots, solution hybridization, solid support based sandwich hybridization, bead-based, silicon chip-based and microtiter well-based hybridization formats can also be used.

Sample Preparation Extracts and Blotting of DNA onto Membranes:

Whole blood is taken from the patient. The blood is mixed with an equal volume of 0.5–1 N NaOH, and is incubated at ambient temperature for ten to twenty minutes to lyse cells, degrade proteins, and denature any DNA. The mixture is then blotted directly onto prewashed nylon membranes, in multiple aliquots. The membranes are rinsed in 10× SSC (1.5 M NaCl, 0.15 M Sodium Citrate, pH 7.0) for five minutes to neutralize the membrane, then rinsed for five minutes in 1× SSC. For storage, if any, membranes are air-dried and sealed. In preparation for hybridization, membranes are rinsed in 1× SSC, 1% SDS.

Alternatively, 1–10 mls of whole blood is fractionated by standard methods, and the white cell layer ("buffy coat") is separated The white cells are lysed, digested, and the DNA extracted by conventional methods (organic extraction, non-organic extraction, or solid phase). The DNA is quantitated by UV absorption or fluorescent dye techniques. Standardized amounts of DNA (0.1–5 μg) are denatured in base, and blotted onto membranes. The membranes are then rinsed.

Alternative methods of preparing cellular or mitochondrial DNA, such as isolation of mitochondria by mild cellular lysis and centrifugation, may also be used.

Hybridization and Detection:

For examples of synthesis, labelling, use, and detection of oligonucleotide probes, see "Oligonucleotides and Analogues: A Practical Approach", F. Eckstein, ed., Oxford University Press (1992); and "Synthetic Chemistry of Oligonucleotides and Analogs", S. Agrawal, ed., Humana Press (1993), which are incorporated herein by reference.

In this example two COX II codon 74 probes having the following sequences are used: ATC ATC CTA GTC CTC ATC GCC (SEQ. ID. NO. 14) (wild-type) and ATC ATC CTA ATC CTC ATC GCC (SEQ. ID. NO. 29) (mutant).

For detection and quantitation of the abnormal mutation, membranes containing duplicate samples of DNA are hybridized in parallel; one membrane is hybridized with the wild-type probe, the other with the AD probe. Alternatively, the same membrane can be hybridized sequentially with both probes and the results compared.

For example, the membranes with immobilized DNA are hydrated briefly (10–60 minutes) in 1× SSC, 1% SDS, then prehybridized and blocked in 5× SSC, 1% SDS, 0.5% casein, for 30–60 minutes at hybridization temperature (35–60° C., depending on which probe is used). Fresh hybridization solution containing probe (0.1–10 nM, ideally 2–3 nM) is added to the membrane, followed by hybridization at appropriate temperature for 15–60 minutes. The membrane is washed in 1× SSC, 1% SDS, 1–3 times at 45–60° C. for 5–10 minutes each (depending on probe used), then 1–2 times in 1× SSC at ambient temperature. The hybridized probe is then detected by appropriate means.

The average proportion of AD COX gene to wild-type gene in the same patient can be determined by the ratio of the signal of the AD probe to the normal probe. This is a semiquantitative measure of % heteroplasmy in the AD patient and can be correlated to the severity of the disease.

The above and other probes for alteration and quantitation of wild-type and mutant DNA samples are listed in Tables 4 and 5 hereinabove.

Example IV

Detection of COX Mutations by Hybridization (without Prior Amplification)

A. Slot-blot detection of RNA/DNA with $^{32}$P probes

This example illustrates detection of COX mutations by slot-blot detection of DNA with $^{32}$P probes. The reagents are prepared as follows: 4× BP: 2i (w/v) Bovine serum albumin (BSA), 2% (w/v) polyvinylpyrrolidone (PVP, Mol. Wt.:

40,000) is dissolved in sterile H$_2$O and filtered through 0.22-$\mu$ cellulose acetate membranes (Corning) and stored at −20° C. in 50-ml conical tubes.

DNA is denatured by adding TE to the sample for a final volume of 90 $\mu$l. 10 $\mu$l of 2 N NaOH is then added and the sample vortexed, incubated at 65° C. for 30 minutes, and then put on ice. The sample is neutralized with 100 $\mu$l of 2 M ammonium acetate.

A wet piece of nitrocellulose or nylon is cut to fit the slot-blot apparatus according to the manufacturer's directions; and the denatured samples are loaded The nucleic acids are fixed to the filter by baking at 80° C. under vacuum for 1 hr or exposing to UV light (254 nm). The filter is prehybridized for 10–30 minutes in ~5 mls of 1× BP, 5× SSPE, 1% SDS at the temperature to be used for the hybridization incubation For 15–30-base probes, the range of hybridization temperatures is between 35–60° C. For shorter probes or probes with low G-C content, a lower temperature is used. At least 2×10$^6$ cpm of detection oligonucleotide per ml of hybridization solution is added. The filter is double sealed in Scotchpak™ heat sealable pouches (Kapak Corporation) and incubated for 90 min. The filter is washed 3 times at room temperature with 5-minute washes of 20× SSPE : 3M NaCl, 0.02M EDTA, 0.2 Sodium Phospate, pH 7.4, 1t SDS on a platform shaker. For higher stringency, the filter can be washed once at the hybridization temperature in 1× SSPE, 1% SDS for 1 minute. Visualization is by autoradiography on Kodak XAR film at −70° C. with an intensifying screen. To estimate the amount of target, compare the amount of target detected by visual comparison with hybridization standards of known concentration.

B. Detection of RNA/DNA by slot-blot analysis with alkaline phosphatase-oligonucleotide conjugate probes This example illustrates detection of COX mutations by slot-blot detection of DNA with alkaline phosphatase-oligonucleotide conjugate probes, using either a color reagent or a chemiluminescent reagent. The reagents are prepared as follows:

Color reagent: For the color reagent, the following are mixed together, fresh 0.16 mg/ml 5-bromo-4-chloro-3-indolyl phosphate (BCIP), 0.17 mg/ml nitroblue tetrazolium (NBT) in 100 mM NaCl, 100 mM Tris. HCl 5 mM MgCl$_2$ and 0.1 mM ZnCl$_2$, pH 9.5.

Chemiluminescent reagent: For the chemiluminescent reagent, the following are mixed together, 250 $\mu$M 3-adamantyl 4-methoxy 4-(2-phospho)phenyl dioxetane (AMPPD), (Tropix Inc., Bedford, Mass.) in 100 mM diethanolamine-HCl, 1 mM MgCl$_2$ pH 9.5, or prefomulated dioxetane substrate Lumiphos™ 530 (Lumigen, Inc., Southfield, Mich.).

DNA target (0.01–50 fmol) is immobilized on a nylon membrane as described above. The nylon membrane is incubated in blocking buffer (0.2% I-Block (Tropix, Inc.), 0.5× SSC, 0.1% Tween 20) for 30 min. at room temperature with shaking. The filter is then prehybridized in hybridization solution (5× SSC, 0.5% BSA, 1% SDS) for 30 minutes at the hybridization temperature (37–60° C.) in a sealable bag using 50–100 $\mu$l of hybridization solution per cm of membrane. The solution is removed and briefly washed in warm hybridization buffer. The conjugate probe is then added to give a final concentration of 2–5 nM in fresh hybridization solution and final volume of 50–100 1$\mu$l/cm$^2$ of membrane. After incubating for 30 minutes at the hybridization temperature with agitation, the membrane is transferred to a wash tray containing 1.5 ml of preheated wash-1 solution (1× SSC, 0.1% SDS)/cm$^2$ of membrane and agitated at the wash temperature (usually optimum hybridization temperature minus 10° C.) for 10 minutes. Wash-1 solution is removed and this step is repeated once more. Then wash-2 solution (1× SSC) added and then agitated at the wash temperature for 10 minutes. Wash-2 solution is removed and immediate detection is done by color.

Detection by color is done by immersing the membrane fully in color reagent, and incubating at 20–37° C. until color development is adequate. When color development is adequate, the development is quenched by washing in water.

For chemiluminescent detection, the following wash steps are performed after the hybridization step (see above). Thus, the membrane is washed for 10 min. with wash-1 solution at room temperature, followed by two 3–5 min. washes at 50–60° C. with wash-3 solution (0.5× SSC, 0.1% SDS). The membrane is then washed once with wash-4 solution (1× SSC, 1% Triton X 100) at room temperature for 10 min., followed by a 10 min. wash at room temperature with wash-2 solution. The membrane is then rinsed briefly (~1 min.) with wash-5 solution (50 mM NaHCO$_3$/1 mM MgCl$_2$, pH 9.5).

Detection by chemiluminescence is done by immersing the membrane in luminescent reagent, using 25–50 $\mu$l solution/cm$^2$ of membrane. Kodak XAR-5 film (or equivalent; emission maximum is at 477 nm) is exposed in a light-tight cassette for 1–24 hours, and the film developed.

Example V

Detection of COX Mutations by Amplification and Hybridization

This example illustrates taking a test sample of blood, preparing DNA, amplifying a section of a specific COX gene by polymerase chain reaction (PCR), and detecting the mutation by oligonucleotide hybridization in a dot blot format.

Sample Preparation and Preparing of DNA:

Whole blood is taken from the patient. The blood is lysed, and the DNA prepared for PCR by using procedures described in Example 1.

Amplification of Target COX genes by Polymerase Chain Reaction, and Blotting onto Membranes:

The treated DNA from the test sample is amplified using procedures described in Example 1. After amplification, the DNA is denatured, and blotted directly onto prewashed nylon membranes, in multiple aliquots. The membranes are rinsed in 10× SSC for five minutes to neutralize the membrane, then rinsed for five minutes in 1× SSC. For storage, if any, membranes are air-dried and sealed. In preparation for hybridization, membranes are rinsed in 1× SSC, 1% SDS.

Hybridization and Detection:

Hybridization and detection of the amplified genes are accomplished as detailed in Example III.

Although the invention has been described with reference to the disclosed embodiments, those skilled in the art will readily appreciate that the specific examples provided herein are only illustrative of the invention and not limitative thereof. It should be understood that various modifications can be made without departing from the scope of the invention.

Example VI

Synthesis of Antisense Oligonucleotides

Standard manufacturer protocols for solid phase phosphoramidite-based DNA or RNA synthesis using an ABI DNA synthesizer are employed to prepare antisense oligomers. Phosphoroamidite reagent monomers (T, C, A, G, and U) are used as received from the supplier. Applied BioEystems Division/Perkin Elmer, Foster City, Calif. For routine oligomer synthesis, 1 μmole scale syntheses reactions are carried out utilizing THF/$I_2$/lutidine for oxidation of the phosphoramidite and Beaucage reagent for preparation of the phosphorothioate oligomers. Cleavage from the solid support and deprotection are carried out using ammonium hydroxide under standard conditions. Purification is carried out via reverse phase HPLC and quantification and identification is performed by UV absorption measurements at 260 nm, and mass spectrometry.

Example VII

Inhibition of Mutant Mitochondria in Cell Culture

Antisense phosphorothioate oligomer complementary to the COX gene mutant at codon 193 and thus non-complementary to wild-type COX gene mutant RNA is added to fresh medium containing Lipofectin® Gibco BRL (Gaithersburg, Md.) at a concentration of 10 μg/ml to make final concentrations of 0.1, 0.33, 1, 3.3, and 10 μM. These are incubated for 15 minutes then applied to the cell culture. The culture is allowed to incubate for 24 hours and the cells are harvested and the DNA isolated and sequenced as in previous examples. Quantitative analysis results shows a decrease in mutant COX DNA to a level of less than 1% of total COX.

The antisense phosphorothioate oligomer non-complementary to the COX gene mutant at codon 193 and non-complementary to wild-type COX is added to fresh medium containing lipofectin at a concentration of 10 μg/mL to make final concentrations of 0.1, 0.33, 1, 3.3, and 10 μM these are incubated for 15 minutes then applied to the cell culture. The culture is allowed to incubate for 24 hours and the cells are harvested and the DNA isolated and sequenced as in previous examples. Quantitative analysis results showed no decrease in mutant COX DNA.

Example VIII

Inhibition of Mutant Mitochondria in Vivo

Mice are divided into six groups of 10 animals per group. The animals are housed and fed as per standard protocols. To groups 1 to 4 is administered ICV, antisense phosphorothioate oligonucleotide, prepared as described in Example VI, complementary to mutant COX gene RNA, respectively 0.1, 0.33, 1.0 and 3.3 nmol each In 5 μL. To group 5 is administered ICV 1.0 nmol in 5 μL of phosphorothioate oligonucleotide non-complementary to mutant COX gene RNA and non-complementary to wild-type COX gene RNA. To group 6 is administered ICV vehicle only. Dosing is performed once a day for ten days. The animals are sacrificed and samples of brain tissue collected. This tissue is treated as previously described and the DNA isolated and quantitatively analyzed as in previous examples. Results show a decrease in mutant COX DNA to a level of less than 1% of total COX for the antisense treated group and no decrease for the control group.

Example IX

Agents for the Detection and Selective Destruction of Defective Mitochondria a. Preparation of 10-N-(10-Hydroxy-1-decyl)-3,6-bis (dimethylamino)acridine bromide salt 3,6-bis(dimethylamino)acridine (1.0 millimole) is dissolved in DMF (100 mL) containing 1.1 equivalent of tertiary amine base. To this is added 10-hydroxy-1-bromo decane (1.1 millimole), and the mixture is heated to reflux. When monitoring by TLC shows no remaining 3,6-bis (dimethylamino)acridine, the reaction is cooled and the 10-N-(10-hydroxy-1-decyl)-3,6-bis(dimethylamino) acridine is isolated (0.75 millimoles).

b. Preparation of 10-N-(10-phosphoryl-1-decyl)-3,6-bis (dimethylamino)acridine chloride salt 10-N-(10-Hydroxy-1-decyl)-3,6-bis(dimethylamino) acridine (1.0 millimole) is dissolved in pyridine (100 mL). To this is added 2-(N,N-dimethylamino)-4-nitrophenyl phosphate (1.1 millimole) according to the procedure of Taguchi (*Chem. Pharm. Bull.*, 23:1586 (1975), and the mixture is stirred under a nitrogen atmosphere. When monitoring by TLC showed no remaining 10-N-(10-hydroxy-1-decyl)-3,6-bis(dimethylamino)acridine, the reaction is worked up according to Taguchi and the 10-N-(10-phosphoryl-1-decyl)-3,6-bis(dimethylamino)acridine is isolated (0.75 millimoles).

c. Preparation of 10-N-(10-thiophosphoryl-1-decyl)-3,6-bis (dimethylamino)acridine chloride salt 10-N-(10-hydroxy-1-decyl)-3,6-bis(dimethylamino) acridine (1,0 millimole) is dissolved in DMF (100 mL). To this is added triimidazolyl-1-phosphine sulfide (1.1 millimole) according to the procedure of Eckstein (*Journal of the American Chemical Society*, 92:4718, (1970)) and the mixture stirred under a nitrogen atmosphere. When monitoring by TLC shows no remaining 10-N-(10-Hydroxy-1-decyl)-3,6-bis(dimethylamino)acridine, the reaction is worked up according to Eckstein and the 10-N-(10-thiophosphoryl-1-decyl)-3,6-bis(dimethylamino)acridine is isolated (0.75 millimoles).

d. Preparation of 10-N-(11-undecanoic acid)-3,6-bis (dimethylamino)acridine bromide salt 3,6-Bis(dimethylamino)acridine (1.0 millimole) is dissolved in DMF (100 mL). To this is added 11-bromo undecanoic acid (1.1 millimole) and the mixture is heated to reflux. When monitoring by TLC shows no remaining 3,6-bis(dimethylamino)acridine, the reaction is cooled and the 10-N-(11-undecanoic acid)-3,6-bis(dimethylamino) acridine is isolated (0.75 millimoles).

e. Preparation of 10-N-(11-undecyl-2,4-dinitrophenyl urethane)-3,6-bis(dimethylamino)acridine bromide salt 10-N-(11-Undecanoic acid)-3,6-bis(dimethylamino) acridine (1.0 millimole) is dissolved in THF (100 mL). To this is added 2,4-dinitrophenol (1.1 millimole) and diphenylphosphoryl azide (1.1 millimole), and the mixture is stirred while heating to 70° C. When monitoring by TLC shows no remaining 10-N-(11-undecanoic acid)-3,6-bis (dimethylamino)-acridine, the reaction is cooled and the 10-N-(11-undecyl-2,4-dinitrophenyl urethane)-3,6-bis (dimethylamino)acridine is isolated (0.75 millimoles)

f. Preparation of 10-N-(11-undecan-1-oic acid 2,4-dinitrophenyl ester)-3,6-bis(dimethylamino)acridine bromide salt 10-N-(11-undecanoic acid)-3,6-bis(dimethylamino) acridine (1.0 millimole) is dissolved in DMF (100 mL). To this is added 2,4-dinitrophenol (1.1 millimole), dicyclohexylcarbodimide (1.1 millimole) and hydroxybenztriazole (1.1 millimole), and the mixture is stirred. When monitoring by TLC shows no remaining 10-N-(11-undecanoic acid)-3,6-bis(dimethylamino)-acridine, the reaction is cooled and the 10-N-(11-undecan-1-oic acid 2,4-dintrophenyl ester)-3,6-bis(dimethylamino)acridine is isolated (0.75 millimoles).

g. Preparation of N'-(2-hydroxyethyl)-JC-1

According to the procedure of Yamamoto et al. *Bulletin of the Chemical Society of Japan*, 46:1509–11 (1973)), 2-methyl-5,6-dichloro-N-ethyl-N'-(2-hydroxyethyl) benzimidazole is heated with aniline and ethyl orthoformate at 100° C. To this is added acetic anhydride and potassium acetate and heating is continued at 160° C. The reaction is worked up as described in Yamamoto et al. and the product isolated.

h. Preparation of bis N'-(2-phosphoryl-1-ethyl)-JC-1

N'-(2-hydroxyethyl)-JC-1 (1.0 millimole) is dissolved in pyridine (100 mL). To this is added 2-(N,N-dimethylamino)-4-nitrophenyl phosphate (1.1 millimole) according to the procedure of Taguchi (*Chem. Pharm. Bull.*, 23, 1586 (1975), and the mixture is stirred under a nitrogen atmosphere. When monitoring by TLC shows no remaining 10-N-(10-hydroxy-1-decyl)-3,6-bis(dimethylamino)acridine, the reaction is worked up according to Taguchi and bis N'-(2-phosphoryl-1-ethyl) JC-1 was isolated (0.75 millimoles).

We claim:

1. A method for selectively accumulating a mitochondrial disabling or destructive amount of a conjugate molecule in mitochondria having defective cytochrome c oxidase activity comprising:
   (a) providing a conjugate molecule comprising a targeting molecule conjugated to a toxin, wherein said targeting molecule selected accumulates in mitochondria having defective cytochrome c oxidase activity; and
   (b) contacting mitochondria with said conjugate molecule, wherein said mitochondria having defective cytochrome c oxidase activity accumulate a disabling or destructive amount of said conjugate molecule.

2. A method for selectively accumulating a mitochondrial disabling or destructive amount of a conjugate molecule in mitochondria having defective cytochrome c oxidase activity comprising:
   (a) providing a conjugate molecule comprising a targeting molecule conjugated to a toxin, wherein said targeting molecule is a lipophilic cation selected from the group consisting of acridine orange, acridine orange derivatives, JC-1 and JC-1 derivatives; and
   (b) contacting mitochondria with said conjugate molecule, wherein said mitochondria having defective cytochrome c oxidase activity accumulate a disabling or destructive amount of said conjugate molecule.

3. The method of either claim 1 or 2 wherein the conjugate molecule further comprises a linker attaching the targeting molecule and the toxin.

4. The method of claim 3 wherein said linker contains a functional group selected from the group consisting of ester, ether, thioether, phosphorodiester, thiophosphorodiester, carbonate, carbamate, hydrazone, oxime, amino and amide.

5. The method of claim 3 wherein said targeting molecule and linker comprise a 10-N-($R_1$-X)-3,6-bis(dimethylamino) acridine derivative wherein $R_1$ is an aliphatic group containing from 5 to 20 carbons, and X is attached to the terminal carbon of the alkane group and is selected from the group consisting of ester, ether, thioether, phosphorodiester, thiophosphorodiester, carbonate, carbamate, hydrazone, oxime, amino and amide.

6. The method of claim 3 wherein said targets molecule is JC-1 or a JC-1 derivative, and wherein said linker comprises a functional group selected from the group consisting of ester, ether, thioether, phosphorodiester, thiophosphorodiester, carbonate, carbamate, hydrazone, oxime, amino and amide.

7. The method of claim 6 wherein said linker is attached to said JC-1 or JC-1 derivative via substitution of at least one of the four chlorine atoms at the 5, 5', 6 and 6' carbon positions of said JC-1 or JC-1 derivative.

8. The method of claim 6, wherein said linker is attached to said JC-1 or JC-1 derivative via substitution of the terminal carbon hydrogen of at least one of the four ethyl groups at the 1, 1', 3 and 3' positions of said JC-1 or JC-1 derivative.

9. The method of claim 6, wherein said linker is attached to said JC-1 or JC-1 derivative via substitution of one of the olefinic hydrogens of said JC-1 or JC-1 derivative.

10. The method of claim 6, wherein said linker further comprises an alkyl group of 2–20 carbon atoms.

11. A method for selectively accumulating a mitochondrial disabling or destructive amount of a conjugate molecule in mitochondria having defective cytochrome c oxidase activity comprising:
    (a) providing a conjugate molecule comprising a targeting molecule conjugated to a toxin, wherein said targeting molecule is selected from the group consisting of rhodamine 123 and derivatives of rhodamine 123; and
    (b) contacting mitochondria with said conjugate molecule, wherein said mitochondria having defective cytochrome c oxidase activity accumulate a disabling or destructive amount of said conjugate molecule.

12. The method of any of claims 1, 2 or 11, wherein said mitochondria having defective cytochrome c oxidase activity have one or more mutations in one or more cytochrome c oxidase genes.

13. The method of any of claims 1, 2 or 11 wherein said toxin is selected from the group consisting of phosphate, thiophosphate, dinitrophenol, maleimide and antisense oligonucleic acids.

14. The method of claim 11, wherein the conjugate molecule further comprises a linker attaching the targeting molecule and the toxin.

15. A method for selectively accumulating a conjugate molecule in mitochondria displaying increased transmembrane potential comprising:
    (a) providing a conjugate molecule comprising a targeting( molecule conjugated to a toxin, wherein said targeting molecule is JC-1 or a JC-1 derivative; and
    (b) contacting mitochondria with said conjugate molecule.

16. A method for selectively accumulating a conjugate molecule in mitochondria, wherein the accumulation of said conjugate molecule is independent of the transmembrane potential, comprising:
- (a) providing a conjugate molecule comprising a targeting molecule conjugated to a toxin, wherein said targeting molecule is acridine orange or an acridine orange derivative; and
- (b) contacting mitochondria with said conjugate molecule.

17. The method of claim 15 wherein the conjugate molecule further comprises a linker attaching the targeting molecule and the toxin.

18. The method of any of claims 15 or 16 wherein said toxin is selected from the group consisting of phosphate, thiophosphate, dinitrophenol, and maleimide and antisense oligonucleic acids.

19. The method of claim 16 wherein the conjugate molecule further comprises a linker attaching the targeting molecule and the toxin.

20. The method of claim 17 wherein said linker contains a functional group selected from the group consisting of ester, ether, thioether, phosphorodiester, thiophosphorodiester, carbonate, carbamate, hydrazone, oxime, amino and amide.

21. The method of claim 17 wherein said targeting molecule and linker comprise a 10-N-($R_1$-X)-3,6-bis(dimethylamino)acridine derivative wherein $R_1$ is an aliphatic group containing from 5 to 20 carbons, and X is attached to the terminal carbon of the alkane group and is selected from the group consisting of ester, ether, thioether, phosphorodiester, thiophosphorodiester, carbonate, carbamate, hydrazone, oxime, amino and amide.

22. The method of claim 20 wherein said linker is attached to said JC-1 or JC-1 derivative via substitution of at least one of the four chlorine atoms at the 5, 5', 6 and 6' carbon positions of said JC-1 or JC-1 derivative.

23. The method of claim 20 wherein said linker is attached to said JC-1 or JC-1 derivative via substitution of the terminal carbon hydrogen of at least one of the four ethyl groups at the 1, 1', 3 and 3' positions of said JC-1 or JC-1 derivative.

24. The method of claim 20 wherein said linker is attached to said JC-1 or JC-1 derivative via substitution of one of the olefinic hydrogens of said JC-1 or JC-1 derivative.

25. The method of claim 20 wherein said linker further comprises an alkyl group of 2–20 carbon atoms.

26. The method of claim 19 wherein the conjugate molecule further comprises a linker attaching the targeting molecule and the toxin, and wherein said linker contains a functional group selected from the group consisting of ester, ether, thioether, phosphorodiester, thiophosphorodiester, carbonate, carbamate, hydrazone, oxime, amino and amide.

27. The method of claim 19 wherein said targeting molecule and linker comprise a 10-N-($R_1$-X)-3,6-bis(dimethylamino)acridine derivative wherein $R_1$ is an aliphatic group containing from 5 to 20 carbons, and X is attached to the terminal carbon of the alkane group and is selected from the group consisting of ester, ether, thioether, phosphorodiester, thiophosphorodiester, carbonate, carbamate, hydrazone, oxime, amino and amide.

28. The method of claim 14 wherein said linker contains a functional group selected from the group consisting of ester, ether, thioether, phosphorodiester, thiophosphorodiester, carbonate, carbamate, hydrazone, oxime, amino and amide.

29. The method of claim 14 wherein said targeting moleclue and linker comprise a 10-N-($R_1$-X)-3,6-bis(dimethylamino)acridine derivative wherein $R_1$ is an aliphatic group containing from 5 to 20 carbons, and X is attached to the terminal carbon of the alkane group and is selected from the group consisting of ester, ether, thioether, phosphorodiester, thiophosphorodiester, carbonate, carbamate, hydrazone, oxime, amino and amide.

* * * * *

UNITED STATES PATENT AND TRADEMARK OFFICE
CERTIFICATE OF CORRECTION

PATENT NO.    : 6,171,859 B1
DATED         : January 9, 2001
INVENTOR(S)   : Hernstadt et al.

It is certified that error appears in the above-identified patent and that said Letters Patent is hereby corrected as shown below:

<u>Title page,</u>
Item [75], Inventors, "Corinna Hernstadt, San Diego, CA (US); William Davis Parker, Charlottesville, VA (US)" should read -- Inventors: Corinna Herrnstadt, John S. Kiely, Robert E. Davis, Soumitra S. Ghosh, all of San Diego, CA (US); William Davis Parker, Charlottesville, VA, (US) --.

Item [56], References Cited, "Parker, "Nucleotide Sequence of Human Mitochondrial Cytochrome C Oxidase II cDNA," 640: 59-64, 1991." should read -- Parker et al., "Cytochrome Oxidase Deficiency in Alzhmers's Disease," Annals of the New York Academy of Sciences 640: 59-64, 1991. --.

<u>Column 151,</u>
Line 47, "1 or 2 wherein" should read -- 1 or 2, wherein --.
Line 62, "said targets" should read -- said targeting --.

<u>Column 152,</u>
Line 62, "targeting ( molecule" should read -- targeting molecule --.

Signed and Sealed this

Sixth Day of August, 2002

*Attest:*

JAMES E. ROGAN
*Attesting Officer*        *Director of the United States Patent and Trademark Office*